(12) United States Patent
Soyka et al.

(10) Patent No.: US 8,148,517 B2
(45) Date of Patent: Apr. 3, 2012

(54) PHOSPHORYLATED WAXY POTATO STARCH

(75) Inventors: Stephan Soyka, Berlin (DE); Jens Pilling, Dortmund (DE); Claus Frohberg, Kleinmachnow (DE)

(73) Assignee: Bayer Cropscience AG, Monheim Am Rhein (DE)

( * ) Notice: Subject to any disclaimer, the term of this patent is extended or adjusted under 35 U.S.C. 154(b) by 713 days.

(21) Appl. No.: 11/909,926

(22) PCT Filed: Mar. 30, 2006

(86) PCT No.: PCT/EP2006/003027
§ 371 (c)(1),
(2), (4) Date: Nov. 20, 2008

(87) PCT Pub. No.: WO2006/103107
PCT Pub. Date: Oct. 5, 2006

(65) Prior Publication Data
US 2009/0105469 A1    Apr. 23, 2009

Related U.S. Application Data

(60) Provisional application No. 60/669,665, filed on Apr. 8, 2005.

(30) Foreign Application Priority Data

Apr. 1, 2005  (EP) ..................................... 05090085

(51) Int. Cl.
*C08B 30/04* (2006.01)
*C12P 19/04* (2006.01)
*C12P 19/18* (2006.01)

(52) U.S. Cl. ........................... 536/102; 435/97; 435/101
(58) Field of Classification Search .................. 536/102; 435/97, 101
See application file for complete search history.

(56) References Cited

U.S. PATENT DOCUMENTS

| 2,845,368 | A | * | 7/1958 | Fredrickson ..................... 127/38 |
| 4,962,028 | A | | 10/1990 | Bedbrook et al. |
| 5,034,322 | A | | 7/1991 | Rogers et al. |
| 5,639,952 | A | | 6/1997 | Quail et al. |
| 5,656,496 | A | | 8/1997 | Quail et al. |
| 6,083,909 | A | * | 7/2000 | Sommermeyer et al. .... 514/13.4 |
| 6,479,468 | B1 | * | 11/2002 | Hedlund et al. ................ 514/60 |
| 6,596,928 | B1 | * | 7/2003 | Landschutze ................ 800/284 |
| 6,940,001 | B1 | * | 9/2005 | Landschutze ................ 800/284 |
| 2003/0150023 | A1 | * | 8/2003 | Klucinec et al. .............. 800/284 |
| 2006/0253929 | A1 | * | 11/2006 | Frohberg ...................... 800/284 |

FOREIGN PATENT DOCUMENTS

| EP | 0 120 516 | 10/1984 |
| EP | 0 292 435 | 11/1988 |
| EP | 0 321 201 | 6/1989 |
| EP | 0 465 875 | 1/1992 |
| EP | 0 513 849 | 11/1992 |
| WO | WO 91/01373 | 2/1991 |
| WO | WO 92/11376 | 7/1992 |
| WO | WO 92/14827 | 9/1992 |
| WO | WO 93/07279 | 4/1993 |
| WO | WO 95/06128 | 3/1995 |
| WO | WO 95/15972 | 6/1995 |
| WO | WO 97/04112 | 2/1997 |
| WO | WO 97/04113 | 2/1997 |
| WO | WO 98/37213 | 8/1998 |
| WO | WO 98/37214 | 8/1998 |
| WO | WO 99/53050 | 10/1999 |
| WO | WO 00/08184 | 2/2000 |
| WO | WO 00/66745 | 11/2000 |
| WO | WO 01/12782 | 2/2001 |
| WO | WO 01/19975 | 3/2001 |
| WO | WO 2005030942 A1 * | 4/2005 |

OTHER PUBLICATIONS

Definition of derivative, Oxford English Dictionary, http://dictionary.oed.com/, accessed online on May 20, 2010.*
Definition of starch, Oxford English Dictionary, http://www.oed.com/, accessed online on May 26, 2011.*
International Preliminary Report on Patentability issued in International Application No. PCT/EP2006/003027, dated Oct. 3, 2007.
Aarts et al. (1993) *Nature* 363: 715-717.
Abel (1995) *Berlin Free University dissertation*.
Abel et al. (1996) *Plant Journal* 10(6): 981-991.
Ali and Siddiq (1999) *Indian Journal of Genetics* 59(1): 23-28.
Altmann et al. (1992) *Theoretical and Applied Genetics* 84: 371-383.
An et al. (1985) *EMBO Journal* 4: 277-287.
Arntzen (1997) *TIBTECH* 15: 441-447.
Arora et al. (1992) *Annals of Biology* 8(1): 65-69.
Azpiroz-Leehan and Feld (1997) *Trends in Genetics* 13(4): 152-156.
Baba et al. (1991) *Biochem. Biophys. Res. Commun.* 191(1): 87-94.
Bachem et al. (1996) *Plant Journal* 9(5): 745-753.
Bäumlein et al. (1991) *Mol. Gen. Genet.* 225: 459-467.
Becker et al. (1992) *Plant Mol. Bio.* 20: 1195-1197.
Beetham et al. (1999) *PNAS* 96: 8774-8778.
Belzile and Yoder (1992) *Plant Journal* 2(2): 173-179.
Bevan (1984) *Nucleic Acid Research* 12: 8711-8721.
Blennow et al. (2000) *Int. J. of Biological* 27: 211-218.
Bonsal et al. (1992) *Proc. Natl. Acad. Sci. USA* 89: 3654-3658.
Castiglioni et al. (1998) *Genetics* 149: 2039-2056.
Chan et al. (1993) *Plant Mol. Biol.* 22: 491-506.
Cho et al. (1999) *Nature Genetics* 23: 203-207.
Cole-Strauss et al. (1996) *Science* 273: 1386-1389.
Conner and Domisse (1992) *Int. J. Plant Sci.* 153: 550-555.
de Borne et al. (1994) *Mol. Gen. Genet.* 243: 613-621.
de Feyter et al. (1996) *Mol. Gen. Genet.* 250: 329-338.
Deng et al. (1990) *Science in China* 33: 28-34.
Drenkard et al. (2000) *Plant Physiology* 124: 1483-1492.
Dwivedi et al. (2000) *Journal of Medicinal and Aromatic* 22: 460-463.

(Continued)

*Primary Examiner* — Shaojia Anna Jiang
*Assistant Examiner* — Jonathan S Lau
(74) *Attorney, Agent, or Firm* — Hunton & Williams, LLP

(57) ABSTRACT

The invention relates to potato starches having an amylose content of less than 10% by weight, a phosphate content in the C6 position of between 35 and 100 nmol of phosphate per milligram of starch and a content of side chains having a DP of from 12 to 19 which is elevated as compared with that in potato starch from corresponding wild-type potato plants.

30 Claims, 1 Drawing Sheet

OTHER PUBLICATIONS

Ehrenberg and Hussain (1981) *Mutation Research* 86: 1-113.
Fiedler et al. (1993) *Plant Mol. Biol.* 22: 669-679.
Flavell et al. (1995) *Curr. Top. Microbiol. Immunol.* 197: 43-46.
Fraley et al. (1986) *Crit. Rev. Plant Sci.* 4(1): 1-46.
Franken et al. (1997) *Current Opinion in Biotechnology* 8: 411-416.
Frey et al. (1989) *Molecular and General Genetics* 217: 172-177.
Fromm et al. (1990) *Biotechnology* 8: 833-844.
Gielen et al. (1984) *EMBO Journal* 3: 835-846.
Gielen et al. (1989) *EMBO Journal* 8: 23-29.
Gordon-Kamm et al. (1990) *Plant Cell* 2: 603-818.
Greco et al. (2001) *Plant Physiology* 125: 1175-1177.
Gupta and Sharma (1990) *Oryza* 27: 217-219.
R. D. Hall (1999) Methods in Molecular Biology "Plant Cell Culture Protocols" pp. 1-421.
Hanley et al. (2000) *Plant Journal* 22(4): 557-566.
Herrera-Estrella et al. (1983) *Nature* 303: 209-213.
Hiei et al. (1994) *Plant Journal* 6: 271-282.
Hirochika (2001) *Current Opinion in Plant Biology* 4: 118-122.
Hiroyuki et al. (1999) *Plant Journal* 19(5): 605-613.
Hizukuri and Takagi (1984) *Carbohydrate Research* 134: 1-10.
Hoekema (1985) Chapter V: "Non-Oncogenic T-region Derived Plant Vectors in the *Agrobacterium* Binary System."
Höfgen and Willmitzer (1990) *Plant Science* 66: 221-230.
Hoogkamp et al. (2000) *Potato Research* 43: 179-189.
Hovenkamp-Hermelink (1987) *Theoretical and Applied Genetics* 75: 217-221.
Hovenkamp-Hermelink et al. (1988) *Potato Research* 31: 241-246.
Jane, et al. (1996) *Cereal Foods World* 41(11): 827-832.
Jarvis et al. (1994) *Plant Mol. Biol.* 24: 685-687.
Jeon and An (2001) *Plant Science* 161: 211-219.
Jeon and Gynheung (2001) *Plant Science* 161: 211-219.
Jeon et al. (2000) *Plant Journal* 22(6): 561-570.
Jorgensen (1990) *Trends Biotechnol.* 8: 340-344.
Khoshnoodi et al. (1996) *Eur. J. Biochem.* 242(1): 148-155.
Kim et al. (1998) *Gene* 216: 233-243.
Knapp et al. (1988) *Molecular and General Genetics* 213: 285-290.
Konieczny and Ausubel (1993) *Plant Journal* 4: 403-410.
Koprek et al. (2000) *Plant Journal* 24(2): 253-263.
Kossmann et al. (1991) *Mol. Gen. Genet.* 230: 39-44.
Koziel et al. (1993) *Biotechnology* 11: 194-200.
Kren et al. (1997) *Hepatology* 25: 1462-1468.
Krens et al. (1982) *Nature* 296: 72-74.
Krysan et al. (1999) *Plant Cell* 11: 2283-2290.
Kumar and Hirochika (2001) *Trends in Plant Science* 6(3): 127-134.
Larsson et al. (1998) *Plant Mol. Biol.* 37: 505-511.
Leisy et al. (1990) *Plant Mol. Biol.* 14: 41-50.
Lister and Dean (1993) *Plant Journal* 4: 745-750.
Liu et al. (2000) *Biochemical Society Transactions* 28(6): 927-929.
Liu et al. (1999) *Molecular and General Genetics* 262: 413-420.
Lloyd et al. (1999) *Biochemical Journal* 338: 515-521.
Maes et al. (1999) *Trends in Plant Science* 4(3): 90-96.
Marshall et al. (1996) *Plant Cell* 8: 1121-1135.
May et al. (1995) *Bio/Technology* 13: 486-492.
McCallum et al. (2000) *Plant Physiology* 123: 439-442.
McKinney et al. (1995) *Plant Journal* 8(4): 613-622.
Meksem et al. (2001) *Molecular Genetics and Genomics* 265: 207-214.
Mette et al. (2000) *EMBO Journal* 19: 5194-5201.
Meyer et al. (1998) *Molecular and General Genetics* 259: 150-160.
Mórocz et al. (1990) *Theor. Appl. Genet.* 80: 721-726.
Müller (1972) *Biologisches Zentralblatt* 91(1): 31-48.
Nam et al. (1989) *Plant Cell* 1: 699-705.
Nehra et al. (1994) *Plant Journal* 5: 285-297.
Niebel et al. (1995) *Top. Microbiol. Immunol.* 197: 91-103.
Owen (1992) *Bio/Technology* 10: 790-794.
Palauqui and Vaucheret (1995) *Plant Mol. Biol.* 29: 149-159.
Parinov and Sundaresan (2000) *Current Opinion in Biotechnology* 11: 157-161.
Parinov et al. (1999) *Plant Cell* 11: 2263-2270.
Pedersen et al. (1982) *Cell* 29: 1015-1026.
Pietrzak et al. (1986) *Nucleic Acid Research* 14: 5857-5868.
Qi et al. (2001) *Nucleic Acid Research* 29(22): e116.
Quatroccio et al. (1990) *Plant Mol. Biol.* 15: 81-93.
Ramachandran and Sundaresan (2001) *Plant Physiology and Biochemistry* 39: 234-252.
Rao (1977) *Cytologica* 42: 443-450.
Ritala et al. (1994) *Plant Mol. Biol.* 24: 317-325.
Ritchie et al. (1993) *Transgenic Res.* 2: 252-265.
Rocha-Sosa et al. (1989) *EMBO Journal* 8: 23-29.
Safford et al. (1998) *Carbohydrate Polymers* 35: 155-168.
Satoh and Omura (1981) *Japanese Journal of Breeding* 31(3): 316-326.
Scarascia-Mugnozza et al. (1993) *Mutation Breeding Review* 10: 1-28.
Schmidt and Willmitzer (1989) *Molecular and General Genetics* 220: 17-24.
Shashidhara et al. (1990) *Journal of Maharashtra Agricultural* 15(1): 20-23.
Shure et al. (1983) *Cell* 35: 225-233.
Singh et al. (2000) *Biochemical Society Transactions* 28(6): 925-927.
Smith et al. (2000) *Nature* 407: 319-320.
Smith-White and Preiss (1994) *Plant Mol. Biol. Rep.* 12: 67-71.
Spencer et al. (1990) *Theor. Appl. Genet.* 79: 625-631.
Stockhaus et al. (1989) *EMBO Journal* 8: 2445-2451.
Stockhaus et al. (1987) *Proc. Natl. Acad. Sci. USA* 84: 7943-7947.
Svec et al. (1998) *Cereal Research Communications* 26(4): 391-396.
Tabata and Hizukuri (1971) *Starch / Stärke* 23: 267-272.
Takeda, et al. (1984) *Carbohydrate Research* 132: 83-92.
Thompson et al. (1994) *Nucleic Acid Research* 22: 4673-4680.
Thorneycroft et al. (2001) *Journal of Experimental Botany* 52: 1593-1601.
Tissier et al. (1999) *Plant Cell* 11: 1841-1852.
Vasil et al. (1993) *Bio/Technology* 11: 1553-1558.
Vaucheret et al. (1995) *Mol. Gen. Genet.* 248: 311-317.
Visser et al. (1991) *Mol. Gen. Genet.* 225: 289-296.
Wan and Lemaux (1994) *Plant Physiol.* 104: 37-48.
Wang and Waterhouse (2000) *Plant Mol. Biol.* 43: 67-82.
Waterhouse et al. (1998) *Proc. Natl. Acad. Sci. USA* 95: 13959-13964.
Werr et al. (1985) *EMBO Journal* 4: 1373-1380.
Whitelam (1996) *Trends Plant Sci.* 1: 268-272.
Wilmink et al. (1992) *Plant Cell Reports* 11: 76-80.
Yoshihara et al. (1996) *FEBS Letters* 383: 213-218.
Young et al. (2001) *Plant Physiology* 125: 513-518.
Zheng et al. (1993) *Plant Journal* 4: 357-366.

* cited by examiner

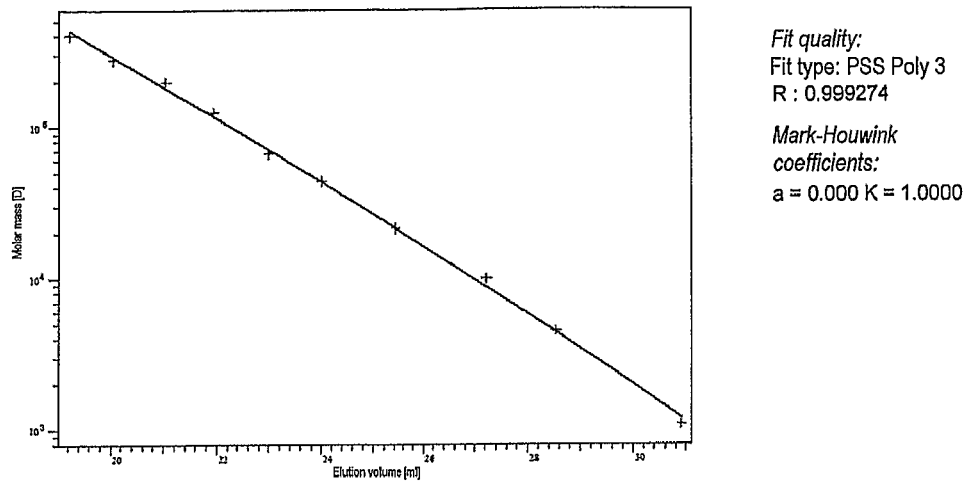
*Fit quality:*
Fit type: PSS Poly 3
R : 0.999274
*Mark-Houwink coefficients:*
a = 0.000 K = 1.0000
| Elution volume [ml] | Molar mass [D] | Sample name | Slope | Deviation [%] |
|---|---|---|---|---|
| 19.22 | 401300 | Dextran T670P | -0.21 | 8.02 |
| 20.05 | 276500 | Dextran T410P | -0.21 | 4.83 |
| 21.03 | 196300 | Dextran T270P | -0.21 | -8.08 |
| 21.93 | 123600 | Dextran T150P | -0.21 | -5.29 |
| 22.98 | 66700 | Dextran T80 | -0.21 | 5.87 |
| 24.00 | 43500 | Dextran T50 | -0.21 | -0.75 |
| 25.43 | 21400 | Dextran T25 | -0.21 | 0.11 |
| 27.22 | 9890 | Dextran T12 | -0.22 | -11.73 |
| 28.55 | 4440 | Dextran T5 | -0.23 | -1.62 |
| 30.92 | 1080 | Dextran T1 | -0.25 | 11.05 |

SEQUENCE LISTING

```
<160> NUMBER OF SEQ ID NOS: 21

<210> SEQ ID NO 1
<211> LENGTH: 4167
<212> TYPE: DNA
<213> ORGANISM: Solanum tuberosum
<220> FEATURE:
<221> NAME/KEY: CDS
<222> LOCATION: (207)..(3899)
<223> OTHER INFORMATION: soluble starch synthase III (SSIII)
<300> PUBLICATION INFORMATION:
<301> AUTHORS: Abel,G.J., Springer,F., Willmitzer,L. and Kossmann,J.
<302> TITLE: Cloning and functional analysis of a cDNA encoding a novel
       139 kDa
<303> JOURNAL: Plant J.
<304> VOLUME: 10
<305> ISSUE: 6
<306> PAGES: 981-991
<307> DATE: 1996
<308> DATABASE ACCESSION NUMBER: X94400
<309> DATABASE ENTRY DATE: 1995-12-22
<313> RELEVANT RESIDUES IN SEQ ID NO: (1)..(4167)
<300> PUBLICATION INFORMATION:
<308> DATABASE ACCESSION NUMBER: EMBL / X94400
<309> DATABASE ENTRY DATE: 1997-04-16
<313> RELEVANT RESIDUES IN SEQ ID NO: (1)..(4167)

<400> SEQUENCE: 1
ttttttaata gattttaaa acccattaa agcaaatacg tatataattg cagcacagat        60
acagagaggg agagagaaag atagtgtgtt gatgaaggag aagagagata tttcacatgg     120
gatgttctat ttgattctgt ggtgaacaag agttttacaa agaacattcc tttttctttt     180
tttcttggtt cttgtgtggg tcagcc atg gat gtt cca ttt cca ctg cat aga     233
                              Met Asp Val Pro Phe Pro Leu His Arg
                               1               5 cca ttg agt tgc aca agt gtc tcc aat gca ata acc cac ctc aag atc      281
Pro Leu Ser Cys Thr Ser Val Ser Asn Ala Ile Thr His Leu Lys Ile
 10              15                  20                  25 aaa cct ttt ctt ggg ttt gtc tct cat gga acc aca agt cta tca gta      329
Lys Pro Phe Leu Gly Phe Val Ser His Gly Thr Thr Ser Leu Ser Val
                 30                  35                  40 caa tct tct tca tgg agg aag gat gga atg gtt act ggg gtt tca ttt      377
Gln Ser Ser Ser Trp Arg Lys Asp Gly Met Val Thr Gly Val Ser Phe
             45                  50                  55 cca ttt tgt gca aat ctc tcg gga aga aga cgg aga aaa gtt tca act      425
Pro Phe Cys Ala Asn Leu Ser Gly Arg Arg Arg Arg Lys Val Ser Thr
         60                  65                  70 act agg agt caa gga tct tca cct aag ggg ttt gtg cca agg aag ccc      473
Thr Arg Ser Gln Gly Ser Ser Pro Lys Gly Phe Val Pro Arg Lys Pro
     75                  80                  85 tca ggg atg agc acg caa aga aag gtt cag aag agc aat ggt gat aaa      521
Ser Gly Met Ser Thr Gln Arg Lys Val Gln Lys Ser Asn Gly Asp Lys
 90                  95                 100                 105
```

| | | | | | | | | | | | | | | | | |
|---|---|---|---|---|---|---|---|---|---|---|---|---|---|---|---|---|
| gaa | agt | caa | agt | act | tca | aca | tct | aaa | gaa | tct | gaa | att | tcc | aac | cag | 569 |
| Glu | Ser | Gln | Ser | Thr | Ser | Thr | Ser | Lys | Glu | Ser | Glu | Ile | Ser | Asn | Gln | |
| | | | 110 | | | | | 115 | | | | | 120 | | | |
| aag | acg | gtt | gaa | gca | aga | gtt | gaa | act | agt | gac | gat | gac | act | aaa | gta | 617 |
| Lys | Thr | Val | Glu | Ala | Arg | Val | Glu | Thr | Ser | Asp | Asp | Asp | Thr | Lys | Val | |
| | | 125 | | | | | 130 | | | | | 135 | | | | |
| gtg | gtg | agg | gac | cac | aag | ttt | ctg | gag | gat | gag | gat | gaa | atc | aat | ggt | 665 |
| Val | Val | Arg | Asp | His | Lys | Phe | Leu | Glu | Asp | Glu | Asp | Glu | Ile | Asn | Gly | |
| | | 140 | | | | 145 | | | | | 150 | | | | | |
| tct | act | aaa | tca | ata | agt | atg | tca | cct | gtt | cgt | gta | tca | tct | caa | ttt | 713 |
| Ser | Thr | Lys | Ser | Ile | Ser | Met | Ser | Pro | Val | Arg | Val | Ser | Ser | Gln | Phe | |
| | 155 | | | | | 160 | | | | | 165 | | | | | |
| gtt | gaa | agt | gaa | gaa | act | ggt | ggt | gat | gac | aag | gat | gct | gta | aag | tta | 761 |
| Val | Glu | Ser | Glu | Glu | Thr | Gly | Gly | Asp | Asp | Lys | Asp | Ala | Val | Lys | Leu | |
| 170 | | | | | 175 | | | | | 180 | | | | | 185 | |
| aac | aaa | tca | aag | aga | tcg | gaa | gag | agt | gat | ttt | cta | att | gat | tct | gta | 809 |
| Asn | Lys | Ser | Lys | Arg | Ser | Glu | Glu | Ser | Asp | Phe | Leu | Ile | Asp | Ser | Val | |
| | | | | 190 | | | | | 195 | | | | | 200 | | |
| ata | aga | gaa | caa | agt | gga | tct | cag | ggg | gaa | act | aat | gcc | agt | agc | aag | 857 |
| Ile | Arg | Glu | Gln | Ser | Gly | Ser | Gln | Gly | Glu | Thr | Asn | Ala | Ser | Ser | Lys | |
| | | | 205 | | | | | 210 | | | | | 215 | | | |
| gga | agc | cat | gct | gtg | ggt | aca | aaa | ctt | tat | gag | ata | ttg | cag | gtg | gat | 905 |
| Gly | Ser | His | Ala | Val | Gly | Thr | Lys | Leu | Tyr | Glu | Ile | Leu | Gln | Val | Asp | |
| | | 220 | | | | | 225 | | | | | 230 | | | | |
| gtt | gag | cca | caa | caa | ttg | aaa | gaa | aat | aat | gct | ggg | aat | gtt | gaa | tac | 953 |
| Val | Glu | Pro | Gln | Gln | Leu | Lys | Glu | Asn | Asn | Ala | Gly | Asn | Val | Glu | Tyr | |
| | 235 | | | | | 240 | | | | | 245 | | | | | |
| aaa | gga | cct | gta | gca | agt | aag | cta | ttg | gaa | att | act | aag | gct | agt | gat | 1001 |
| Lys | Gly | Pro | Val | Ala | Ser | Lys | Leu | Leu | Glu | Ile | Thr | Lys | Ala | Ser | Asp | |
| 250 | | | | | 255 | | | | | 260 | | | | | 265 | |
| gtg | gaa | cac | act | gaa | agc | aat | gag | att | gat | gac | tta | gac | act | aat | agt | 1049 |
| Val | Glu | His | Thr | Glu | Ser | Asn | Glu | Ile | Asp | Asp | Leu | Asp | Thr | Asn | Ser | |
| | | | | 270 | | | | | 275 | | | | | 280 | | |
| ttc | ttt | aaa | tca | gat | tta | att | gaa | gag | gat | gag | cca | tta | gct | gca | gga | 1097 |
| Phe | Phe | Lys | Ser | Asp | Leu | Ile | Glu | Glu | Asp | Glu | Pro | Leu | Ala | Ala | Gly | |
| | | | 285 | | | | | 290 | | | | | 295 | | | |
| aca | gtg | gag | act | gga | gat | tct | tct | cta | aac | tta | aga | ttg | gag | atg | gaa | 1145 |
| Thr | Val | Glu | Thr | Gly | Asp | Ser | Ser | Leu | Asn | Leu | Arg | Leu | Glu | Met | Glu | |
| | | 300 | | | | | 305 | | | | | 310 | | | | |
| gca | aat | cta | cgt | agg | cag | gct | ata | gaa | agg | ctt | gcc | gag | gaa | aat | tta | 1193 |
| Ala | Asn | Leu | Arg | Arg | Gln | Ala | Ile | Glu | Arg | Leu | Ala | Glu | Glu | Asn | Leu | |
| | 315 | | | | | 320 | | | | | 325 | | | | | |
| ttg | caa | ggg | atc | aga | tta | ttt | tgt | ttt | cca | gag | gtt | gta | aaa | cct | gat | 1241 |
| Leu | Gln | Gly | Ile | Arg | Leu | Phe | Cys | Phe | Pro | Glu | Val | Val | Lys | Pro | Asp | |
| 330 | | | | | 335 | | | | | 340 | | | | | 345 | |
| gaa | gat | gtc | gag | ata | ttt | ctt | aac | aga | ggt | ctt | tcc | act | ttg | aag | aat | 1289 |
| Glu | Asp | Val | Glu | Ile | Phe | Leu | Asn | Arg | Gly | Leu | Ser | Thr | Leu | Lys | Asn | |
| | | | | 350 | | | | | 355 | | | | | 360 | | |
| gag | tct | gat | gtc | ttg | att | atg | gga | gct | ttt | aat | gag | tgg | cgc | tat | agg | 1337 |
| Glu | Ser | Asp | Val | Leu | Ile | Met | Gly | Ala | Phe | Asn | Glu | Trp | Arg | Tyr | Arg | |
| | | | 365 | | | | | 370 | | | | | 375 | | | |
| tct | ttt | act | aca | agg | cta | act | gag | act | cat | ctc | aat | gga | gat | tgg | tgg | 1385 |
| Ser | Phe | Thr | Thr | Arg | Leu | Thr | Glu | Thr | His | Leu | Asn | Gly | Asp | Trp | Trp | |
| | | 380 | | | | | 385 | | | | | 390 | | | | |
| tct | tgc | aag | atc | cat | gtt | ccc | aag | gaa | gca | tac | agg | gct | gat | ttt | gtg | 1433 |
| Ser | Cys | Lys | Ile | His | Val | Pro | Lys | Glu | Ala | Tyr | Arg | Ala | Asp | Phe | Val | |
| | 395 | | | | | 400 | | | | | 405 | | | | | |
| ttt | ttt | aat | gga | caa | gat | gtc | tat | gac | aac | aat | gat | gga | aat | gac | ttc | 1481 |
| Phe | Phe | Asn | Gly | Gln | Asp | Val | Tyr | Asp | Asn | Asn | Asp | Gly | Asn | Asp | Phe | |
| 410 | | | | | 415 | | | | | 420 | | | | | 425 | |

-continued

| | | | | | | | | | | | | | | | |
|---|---|---|---|---|---|---|---|---|---|---|---|---|---|---|---|
| agt | ata | act | gtg | aaa | ggt | ggt | atg | caa | atc | att | gac | ttt | gaa | aat | ttc |
| Ser | Ile | Thr | Val | Lys | Gly | Gly | Met | Gln | Ile | Ile | Asp | Phe | Glu | Asn | Phe |
| | | | 430 | | | | | 435 | | | | | 440 | | |

1529

| | | | | | | | | | | | | | | | |
|---|---|---|---|---|---|---|---|---|---|---|---|---|---|---|---|
| ttg | ctt | gag | gag | aaa | tgg | aga | gaa | cag | gag | aaa | ctt | gct | aaa | gaa | caa |
| Leu | Leu | Glu | Glu | Lys | Trp | Arg | Glu | Gln | Glu | Lys | Leu | Ala | Lys | Glu | Gln |
| | | | | 445 | | | | | 450 | | | | | 455 | |

1577

| | | | | | | | | | | | | | | | |
|---|---|---|---|---|---|---|---|---|---|---|---|---|---|---|---|
| gct | gaa | aga | gaa | aga | cta | gcg | gaa | gaa | caa | aga | cga | ata | gaa | gca | gag |
| Ala | Glu | Arg | Glu | Arg | Leu | Ala | Glu | Glu | Gln | Arg | Arg | Ile | Glu | Ala | Glu |
| | | 460 | | | | | 465 | | | | | 470 | | | |

1625

| | | | | | | | | | | | | | | | |
|---|---|---|---|---|---|---|---|---|---|---|---|---|---|---|---|
| aaa | gct | gaa | att | gaa | gct | gac | aga | gca | caa | gca | aag | gaa | gag | gct | gca |
| Lys | Ala | Glu | Ile | Glu | Ala | Asp | Arg | Ala | Gln | Ala | Lys | Glu | Glu | Ala | Ala |
| | 475 | | | | | 480 | | | | | 485 | | | | |

1673

| | | | | | | | | | | | | | | | |
|---|---|---|---|---|---|---|---|---|---|---|---|---|---|---|---|
| aag | aaa | aag | aaa | gta | ttg | cga | gaa | ttg | atg | gta | aaa | gcc | acg | aag | act |
| Lys | Lys | Lys | Lys | Val | Leu | Arg | Glu | Leu | Met | Val | Lys | Ala | Thr | Lys | Thr |
| 490 | | | | | 495 | | | | | 500 | | | | | 505 |

1721

| | | | | | | | | | | | | | | | |
|---|---|---|---|---|---|---|---|---|---|---|---|---|---|---|---|
| cgt | gat | atc | acg | tgg | tac | ata | gag | cca | agt | gaa | ttt | aaa | tgc | gag | gac |
| Arg | Asp | Ile | Thr | Trp | Tyr | Ile | Glu | Pro | Ser | Glu | Phe | Lys | Cys | Glu | Asp |
| | | | 510 | | | | | 515 | | | | | 520 | | |

1769

| | | | | | | | | | | | | | | | |
|---|---|---|---|---|---|---|---|---|---|---|---|---|---|---|---|
| aag | gtc | agg | tta | tac | tat | aac | aaa | agt | tca | ggt | cct | ctc | tcc | cat | gct |
| Lys | Val | Arg | Leu | Tyr | Tyr | Asn | Lys | Ser | Ser | Gly | Pro | Leu | Ser | His | Ala |
| | | | 525 | | | | | 530 | | | | | 535 | | |

1817

| | | | | | | | | | | | | | | | |
|---|---|---|---|---|---|---|---|---|---|---|---|---|---|---|---|
| aag | gac | ttg | tgg | atc | cac | gga | gga | tat | aat | aat | tgg | aag | gat | ggt | ttg |
| Lys | Asp | Leu | Trp | Ile | His | Gly | Gly | Tyr | Asn | Asn | Trp | Lys | Asp | Gly | Leu |
| | | 540 | | | | | 545 | | | | | 550 | | | |

1865

| | | | | | | | | | | | | | | | |
|---|---|---|---|---|---|---|---|---|---|---|---|---|---|---|---|
| tct | att | gtc | aaa | aag | ctt | gtt | aaa | tct | gag | aga | ata | gat | ggt | gat | tgg |
| Ser | Ile | Val | Lys | Lys | Leu | Val | Lys | Ser | Glu | Arg | Ile | Asp | Gly | Asp | Trp |
| | 555 | | | | | 560 | | | | | 565 | | | | |

1913

| | | | | | | | | | | | | | | | |
|---|---|---|---|---|---|---|---|---|---|---|---|---|---|---|---|
| tgg | tat | aca | gag | gtt | gtt | att | cct | gat | cag | gca | ctt | ttc | ttg | gat | tgg |
| Trp | Tyr | Thr | Glu | Val | Val | Ile | Pro | Asp | Gln | Ala | Leu | Phe | Leu | Asp | Trp |
| 570 | | | | | 575 | | | | | 580 | | | | | 585 |

1961

| | | | | | | | | | | | | | | | |
|---|---|---|---|---|---|---|---|---|---|---|---|---|---|---|---|
| gtt | ttt | gct | gat | ggt | cca | ccc | aag | cat | gcc | att | gct | tat | gat | aac | aat |
| Val | Phe | Ala | Asp | Gly | Pro | Pro | Lys | His | Ala | Ile | Ala | Tyr | Asp | Asn | Asn |
| | | | | 590 | | | | | 595 | | | | | 600 | |

2009

| | | | | | | | | | | | | | | | |
|---|---|---|---|---|---|---|---|---|---|---|---|---|---|---|---|
| cac | cgc | caa | gac | ttc | cat | gcc | att | gtc | ccc | aac | cac | att | ccg | gag | gaa |
| His | Arg | Gln | Asp | Phe | His | Ala | Ile | Val | Pro | Asn | His | Ile | Pro | Glu | Glu |
| | | | 605 | | | | | 610 | | | | | 615 | | |

2057

| | | | | | | | | | | | | | | | |
|---|---|---|---|---|---|---|---|---|---|---|---|---|---|---|---|
| tta | tat | tgg | gtt | gag | gaa | gaa | cat | cag | atc | ttt | aag | aca | ctt | cag | gag |
| Leu | Tyr | Trp | Val | Glu | Glu | Glu | His | Gln | Ile | Phe | Lys | Thr | Leu | Gln | Glu |
| | | 620 | | | | | 625 | | | | | 630 | | | |

2105

| | | | | | | | | | | | | | | | |
|---|---|---|---|---|---|---|---|---|---|---|---|---|---|---|---|
| gag | aga | agg | ctt | aga | gaa | gcg | gct | atg | cgt | gct | aag | gtt | gaa | aaa | aca |
| Glu | Arg | Arg | Leu | Arg | Glu | Ala | Ala | Met | Arg | Ala | Lys | Val | Glu | Lys | Thr |
| | 635 | | | | | 640 | | | | | 645 | | | | |

2153

| | | | | | | | | | | | | | | | |
|---|---|---|---|---|---|---|---|---|---|---|---|---|---|---|---|
| gca | ctt | ctg | aaa | act | gaa | aca | aag | gaa | aga | act | atg | aaa | tca | ttt | tta |
| Ala | Leu | Leu | Lys | Thr | Glu | Thr | Lys | Glu | Arg | Thr | Met | Lys | Ser | Phe | Leu |
| 650 | | | | | 655 | | | | | 660 | | | | | 665 |

2201

| | | | | | | | | | | | | | | | |
|---|---|---|---|---|---|---|---|---|---|---|---|---|---|---|---|
| ctg | tct | cag | aag | cat | gta | gta | tat | act | gag | cct | ctt | gat | atc | caa | gct |
| Leu | Ser | Gln | Lys | His | Val | Val | Tyr | Thr | Glu | Pro | Leu | Asp | Ile | Gln | Ala |
| | | | 670 | | | | | 675 | | | | | 680 | | |

2249

| | | | | | | | | | | | | | | | |
|---|---|---|---|---|---|---|---|---|---|---|---|---|---|---|---|
| gga | agc | agc | gtc | aca | gtt | tac | tat | aat | ccc | gcc | aat | aca | gta | ctt | aat |
| Gly | Ser | Ser | Val | Thr | Val | Tyr | Tyr | Asn | Pro | Ala | Asn | Thr | Val | Leu | Asn |
| | | | | 685 | | | | | 690 | | | | | 695 | |

2297

| | | | | | | | | | | | | | | | |
|---|---|---|---|---|---|---|---|---|---|---|---|---|---|---|---|
| ggt | aaa | cct | gaa | att | tgg | ttc | aga | tgt | tca | ttt | aat | cgc | tgg | act | cac |
| Gly | Lys | Pro | Glu | Ile | Trp | Phe | Arg | Cys | Ser | Phe | Asn | Arg | Trp | Thr | His |
| | | | 700 | | | | | 705 | | | | | 710 | | |

2345

| | | | | | | | | | | | | | | | |
|---|---|---|---|---|---|---|---|---|---|---|---|---|---|---|---|
| cgc | ctg | ggt | cca | ttg | cca | cct | cag | aaa | atg | tcg | cct | gct | gaa | aat | ggc |
| Arg | Leu | Gly | Pro | Leu | Pro | Pro | Gln | Lys | Met | Ser | Pro | Ala | Glu | Asn | Gly |
| | 715 | | | | | 720 | | | | | 725 | | | | |

2393

| | | | | | | | | | | | | | | | |
|---|---|---|---|---|---|---|---|---|---|---|---|---|---|---|---|
| acc | cat | gtc | aga | gca | act | gtg | aag | gtt | cca | ttg | gat | gca | tat | atg | atg |
| Thr | His | Val | Arg | Ala | Thr | Val | Lys | Val | Pro | Leu | Asp | Ala | Tyr | Met | Met |
| 730 | | | | | 735 | | | | | 740 | | | | | 745 |

2441

```
gat ttt gta ttt tcc gag aga gaa gat ggt ggg att ttt gac aat aag      2489
Asp Phe Val Phe Ser Glu Arg Glu Asp Gly Gly Ile Phe Asp Asn Lys
            750                 755                 760 agc gga atg gac tat cac ata cct gtg ttt gga gga gtc gct aaa gaa      2537
Ser Gly Met Asp Tyr His Ile Pro Val Phe Gly Gly Val Ala Lys Glu
        765                 770                 775 cct cca atg cat att gtc cat att gct gtc gaa atg gca cca att gca      2585
Pro Pro Met His Ile Val His Ile Ala Val Glu Met Ala Pro Ile Ala
    780                 785                 790 aag gtg gga ggc ctt ggt gat gtt gtt act agt ctt tcc cgt gct gtt      2633
Lys Val Gly Gly Leu Gly Asp Val Val Thr Ser Leu Ser Arg Ala Val
795                 800                 805 caa gat tta aac cat aat gtg gat att atc tta cct aag tat gac tgt      2681
Gln Asp Leu Asn His Asn Val Asp Ile Ile Leu Pro Lys Tyr Asp Cys
810                 815                 820                 825 ttg aag atg aat aat gtg aag gac ttt cgg ttt cac aaa aac tac ttt      2729
Leu Lys Met Asn Asn Val Lys Asp Phe Arg Phe His Lys Asn Tyr Phe
            830                 835                 840 tgg ggt ggg act gaa ata aaa gta tgg ttt gga aag gtg gaa ggt ctc      2777
Trp Gly Gly Thr Glu Ile Lys Val Trp Phe Gly Lys Val Glu Gly Leu
        845                 850                 855 tcg gtc tat ttt ttg gag cct caa aac ggg tta ttt tcg aaa ggg tgc      2825
Ser Val Tyr Phe Leu Glu Pro Gln Asn Gly Leu Phe Ser Lys Gly Cys
    860                 865                 870 gtc tat ggt tgt agc aat gat ggt gaa cga ttt ggt ttc ttc tgt cac      2873
Val Tyr Gly Cys Ser Asn Asp Gly Glu Arg Phe Gly Phe Phe Cys His
875                 880                 885 gcg gct ttg gag ttt ctt ctg caa ggt gga ttt agt ccg gat atc att      2921
Ala Ala Leu Glu Phe Leu Leu Gln Gly Gly Phe Ser Pro Asp Ile Ile
890                 895                 900                 905 cat tgc cat gat tgg tct agt gct cct gtt gct tgg ctc ttt aag gaa      2969
His Cys His Asp Trp Ser Ser Ala Pro Val Ala Trp Leu Phe Lys Glu
            910                 915                 920 caa tat aca cac tat ggt cta agc aaa tct cgt ata gtc ttc acg ata      3017
Gln Tyr Thr His Tyr Gly Leu Ser Lys Ser Arg Ile Val Phe Thr Ile
        925                 930                 935 cat aat ctt gaa ttt ggg gca gat ctc att ggg aga gca atg act aac      3065
His Asn Leu Glu Phe Gly Ala Asp Leu Ile Gly Arg Ala Met Thr Asn
    940                 945                 950 gca gac aaa gct aca aca gtt tca cca act tac tca cag gag gtg tct      3113
Ala Asp Lys Ala Thr Thr Val Ser Pro Thr Tyr Ser Gln Glu Val Ser
955                 960                 965 gga aac cct gta att gcg cct cac ctt cac aag ttc cat ggt ata gtg      3161
Gly Asn Pro Val Ile Ala Pro His Leu His Lys Phe His Gly Ile Val
970                 975                 980                 985 aat ggg att gac cca gat att tgg gat cct tta aac gat aag ttc att      3209
Asn Gly Ile Asp Pro Asp Ile Trp Asp Pro Leu Asn Asp Lys Phe Ile
            990                 995                 1000 ccg att ccg tac  acc tca gaa aac gtt  gtt gaa ggc aaa aca  gca       3254
Pro Ile Pro Tyr Thr Ser Glu Asn Val  Val Glu Gly Lys Thr  Ala
            1005                1010                1015 gcc aag gaa gct  ttg cag cga aaa ctt  gga ctg aaa cag gct  gac       3299
Ala Lys Glu Ala Leu Gln Arg Lys Leu  Gly Leu Lys Gln Ala  Asp
        1020                1025                1030 ctt cct ttg gta  gga att atc acc cgc  tta act cac cag aaa  gga       3344
Leu Pro Leu Val Gly Ile Ile Thr Arg  Leu Thr His Gln Lys  Gly
    1035                1040                1045 atc cac ctc att  aaa cat gct att tgg  cgc acc ttg gaa cgg  aac       3389
Ile His Leu Ile Lys His Ala Ile Trp  Arg Thr Leu Glu Arg  Asn
1050                1055                1060
```

```
gga cag gta gtc ttg ctt ggt tct gct cct gat cct agg gta caa      3434
Gly Gln Val Val Leu Leu Gly Ser Ala Pro Asp Pro Arg Val Gln
            1065                1070                1075 aac gat ttt gtt aat ttg gca aat caa ttg cac tcc aaa tat aat      3479
Asn Asp Phe Val Asn Leu Ala Asn Gln Leu His Ser Lys Tyr Asn
            1080                1085                1090 gac cgc gca cga ctc tgt cta aca tat gac gag cca ctt tct cac      3524
Asp Arg Ala Arg Leu Cys Leu Thr Tyr Asp Glu Pro Leu Ser His
            1095                1100                1105 ctg ata tat gct ggt gct gat ttt att cta gtt cct tca ata ttt      3569
Leu Ile Tyr Ala Gly Ala Asp Phe Ile Leu Val Pro Ser Ile Phe
            1110                1115                1120 gag cca tgt gga cta aca caa ctt acc gct atg aga tat ggt tca      3614
Glu Pro Cys Gly Leu Thr Gln Leu Thr Ala Met Arg Tyr Gly Ser
            1125                1130                1135 att cca gtc gtg cgt aaa act gga gga ctt tat gat act gta ttt      3659
Ile Pro Val Val Arg Lys Thr Gly Gly Leu Tyr Asp Thr Val Phe
            1140                1145                1150 gat gtt gac cat gac aaa gag aga gca caa cag tgt ggt ctt gaa      3704
Asp Val Asp His Asp Lys Glu Arg Ala Gln Gln Cys Gly Leu Glu
            1155                1160                1165 cca aat gga ttc agc ttt gat gga gca gat gct ggc gga gtt gat      3749
Pro Asn Gly Phe Ser Phe Asp Gly Ala Asp Ala Gly Gly Val Asp
            1170                1175                1180 tat gct ctg aat aga gct ctc tct gct tgg tac gat ggt cgg gat      3794
Tyr Ala Leu Asn Arg Ala Leu Ser Ala Trp Tyr Asp Gly Arg Asp
            1185                1190                1195 tgg ttc aac tct tta tgc aag cag gtc atg gaa caa gat tgg tct      3839
Trp Phe Asn Ser Leu Cys Lys Gln Val Met Glu Gln Asp Trp Ser
            1200                1205                1210 tgg aac cga cct gct ctt gat tat ttg gag ctt tac cat gct gct      3884
Trp Asn Arg Pro Ala Leu Asp Tyr Leu Glu Leu Tyr His Ala Ala
            1215                1220                1225 aga aag tta gaa tag ttagtttgtg agatgctagc agaaaaattc acgagatctg   3939
Arg Lys Leu Glu
            1230 caatctgtac aggttcagtg tttgcgtctg gacagctttt ttatttccta tatcaaagta  3999 taaatcaagt ctacactgag atcaatagca gacagtcctc agttcatttc attttttgtg  4059 caacatatga aagagcttag cctctaataa tgtagtcatt gatgattatt tgttttggga  4119 agaaatgaga aatcaaagga tgcaaaatac tctgaaaaaa aaaaaaa             4167

<210> SEQ ID NO 2
<211> LENGTH: 1230
<212> TYPE: PRT
<213> ORGANISM: Solanum tuberosum

<400> SEQUENCE: 2

Met Asp Val Pro Phe Pro Leu His Arg Pro Leu Ser Cys Thr Ser Val
1               5                   10                  15

Ser Asn Ala Ile Thr His Leu Lys Ile Lys Pro Phe Leu Gly Phe Val
            20                  25                  30

Ser His Gly Thr Thr Ser Leu Ser Val Gln Ser Ser Ser Trp Arg Lys
        35                  40                  45

Asp Gly Met Val Thr Gly Val Ser Phe Pro Phe Cys Ala Asn Leu Ser
    50                  55                  60

Gly Arg Arg Arg Lys Val Ser Thr Thr Arg Ser Gln Gly Ser Ser
65                  70                  75                  80
```

-continued

```
Pro Lys Gly Phe Val Pro Arg Lys Pro Ser Gly Met Ser Thr Gln Arg
                85                  90                  95
Lys Val Gln Lys Ser Asn Gly Asp Lys Glu Ser Gln Ser Thr Ser Thr
            100                 105                 110
Ser Lys Glu Ser Glu Ile Ser Asn Gln Lys Thr Val Glu Ala Arg Val
            115                 120                 125
Glu Thr Ser Asp Asp Thr Lys Val Val Arg Asp His Lys Phe
            130                 135                 140
Leu Glu Asp Glu Asp Glu Ile Asn Gly Ser Thr Lys Ser Ile Ser Met
145                 150                 155                 160
Ser Pro Val Arg Val Ser Ser Gln Phe Val Glu Ser Glu Thr Gly
                165                 170                 175
Gly Asp Asp Lys Asp Ala Val Lys Leu Asn Lys Ser Lys Arg Ser Glu
            180                 185                 190
Glu Ser Asp Phe Leu Ile Asp Ser Val Ile Arg Glu Gln Ser Gly Ser
            195                 200                 205
Gln Gly Glu Thr Asn Ala Ser Ser Lys Gly Ser His Ala Val Gly Thr
            210                 215                 220
Lys Leu Tyr Glu Ile Leu Gln Val Asp Val Glu Pro Gln Gln Leu Lys
225                 230                 235                 240
Glu Asn Asn Ala Gly Asn Val Glu Tyr Lys Gly Pro Val Ala Ser Lys
                245                 250                 255
Leu Leu Glu Ile Thr Lys Ala Ser Asp Val Glu His Thr Glu Ser Asn
                260                 265                 270
Glu Ile Asp Asp Leu Asp Thr Asn Ser Phe Phe Lys Ser Asp Leu Ile
            275                 280                 285
Glu Glu Asp Glu Pro Leu Ala Ala Gly Thr Val Glu Thr Gly Asp Ser
            290                 295                 300
Ser Leu Asn Leu Arg Leu Glu Met Glu Ala Asn Leu Arg Arg Gln Ala
305                 310                 315                 320
Ile Glu Arg Leu Ala Glu Glu Asn Leu Leu Gln Gly Ile Arg Leu Phe
                325                 330                 335
Cys Phe Pro Glu Val Val Lys Pro Asp Glu Asp Val Glu Ile Phe Leu
                340                 345                 350
Asn Arg Gly Leu Ser Thr Leu Lys Asn Glu Ser Asp Val Leu Ile Met
            355                 360                 365
Gly Ala Phe Asn Glu Trp Arg Tyr Arg Ser Phe Thr Thr Arg Leu Thr
            370                 375                 380
Glu Thr His Leu Asn Gly Asp Trp Trp Ser Cys Lys Ile His Val Pro
385                 390                 395                 400
Lys Glu Ala Tyr Arg Ala Asp Phe Val Phe Asn Gly Gln Asp Val
                405                 410                 415
Tyr Asp Asn Asn Asp Gly Asn Asp Phe Ser Ile Thr Val Lys Gly Gly
            420                 425                 430
Met Gln Ile Ile Asp Phe Glu Asn Phe Leu Leu Glu Glu Lys Trp Arg
        435                 440                 445
Glu Gln Glu Lys Leu Ala Lys Glu Gln Ala Arg Glu Arg Leu Ala
            450                 455                 460
Glu Glu Gln Arg Arg Ile Glu Ala Glu Lys Ala Glu Ile Glu Ala Asp
465                 470                 475                 480
Arg Ala Gln Ala Lys Glu Glu Ala Ala Lys Lys Lys Val Leu Arg
            485                 490                 495
Glu Leu Met Val Lys Ala Thr Lys Thr Arg Asp Ile Thr Trp Tyr Ile
                500                 505                 510
```

-continued

```
Glu Pro Ser Glu Phe Lys Cys Glu Asp Lys Val Arg Leu Tyr Tyr Asn
            515                 520                 525
Lys Ser Ser Gly Pro Leu Ser His Ala Lys Asp Leu Trp Ile His Gly
        530                 535                 540
Gly Tyr Asn Asn Trp Lys Asp Gly Leu Ser Ile Val Lys Lys Leu Val
545                 550                 555                 560
Lys Ser Glu Arg Ile Asp Gly Asp Trp Trp Tyr Thr Glu Val Val Ile
                565                 570                 575
Pro Asp Gln Ala Leu Phe Leu Asp Trp Val Phe Ala Asp Gly Pro Pro
            580                 585                 590
Lys His Ala Ile Ala Tyr Asp Asn Asn His Arg Gln Asp Phe His Ala
        595                 600                 605
Ile Val Pro Asn His Ile Pro Glu Glu Leu Tyr Trp Val Glu Glu Glu
    610                 615                 620
His Gln Ile Phe Lys Thr Leu Gln Glu Arg Arg Leu Arg Glu Ala
625                 630                 635                 640
Ala Met Arg Ala Lys Val Glu Lys Thr Ala Leu Leu Lys Thr Glu Thr
                645                 650                 655
Lys Glu Arg Thr Met Lys Ser Phe Leu Leu Ser Gln Lys His Val Val
            660                 665                 670
Tyr Thr Glu Pro Leu Asp Ile Gln Ala Gly Ser Ser Val Thr Val Tyr
        675                 680                 685
Tyr Asn Pro Ala Asn Thr Val Leu Asn Gly Lys Pro Glu Ile Trp Phe
    690                 695                 700
Arg Cys Ser Phe Asn Arg Trp Thr His Arg Leu Gly Pro Leu Pro Pro
705                 710                 715                 720
Gln Lys Met Ser Pro Ala Glu Asn Gly Thr His Val Arg Ala Thr Val
                725                 730                 735
Lys Val Pro Leu Asp Ala Tyr Met Met Asp Phe Val Phe Ser Glu Arg
            740                 745                 750
Glu Asp Gly Gly Ile Phe Asp Asn Lys Ser Gly Met Asp Tyr His Ile
        755                 760                 765
Pro Val Phe Gly Gly Val Ala Lys Glu Pro Pro Met His Ile Val His
    770                 775                 780
Ile Ala Val Glu Met Ala Pro Ile Ala Lys Val Gly Gly Leu Gly Asp
785                 790                 795                 800
Val Val Thr Ser Leu Ser Arg Ala Val Gln Asp Leu Asn His Asn Val
                805                 810                 815
Asp Ile Ile Leu Pro Lys Tyr Asp Cys Leu Lys Met Asn Asn Val Lys
            820                 825                 830
Asp Phe Arg Phe His Lys Asn Tyr Phe Trp Gly Gly Thr Glu Ile Lys
        835                 840                 845
Val Trp Phe Gly Lys Val Glu Gly Leu Ser Val Tyr Phe Leu Glu Pro
    850                 855                 860
Gln Asn Gly Leu Phe Ser Lys Gly Cys Val Tyr Gly Cys Ser Asn Asp
865                 870                 875                 880
Gly Glu Arg Phe Gly Phe Phe Cys His Ala Ala Leu Glu Phe Leu Leu
                885                 890                 895
Gln Gly Gly Phe Ser Pro Asp Ile Ile His Cys His Asp Trp Ser Ser
            900                 905                 910
Ala Pro Val Ala Trp Leu Phe Lys Glu Gln Tyr Thr His Tyr Gly Leu
        915                 920                 925
Ser Lys Ser Arg Ile Val Phe Thr Ile His Asn Leu Glu Phe Gly Ala
```

```
                  930             935             940
Asp Leu Ile Gly Arg Ala Met Thr Asn Ala Asp Lys Ala Thr Thr Val
945                 950             955             960

Ser Pro Thr Tyr Ser Gln Glu Val Ser Gly Asn Pro Val Ile Ala Pro
                965             970             975

His Leu His Lys Phe His Gly Ile Val Asn Gly Ile Asp Pro Asp Ile
            980             985             990

Trp Asp Pro Leu Asn Asp Lys Phe Ile Pro Ile Pro Tyr Thr Ser Glu
        995             1000            1005

Asn Val Val Glu Gly Lys Thr Ala Ala Lys Glu Ala Leu Gln Arg
    1010            1015            1020

Lys Leu Gly Leu Lys Gln Ala Asp Leu Pro Leu Val Gly Ile Ile
    1025            1030            1035

Thr Arg Leu Thr His Gln Lys Gly Ile His Leu Ile Lys His Ala
    1040            1045            1050

Ile Trp Arg Thr Leu Glu Arg Asn Gly Gln Val Val Leu Leu Gly
    1055            1060            1065

Ser Ala Pro Asp Pro Arg Val Gln Asn Asp Phe Val Asn Leu Ala
    1070            1075            1080

Asn Gln Leu His Ser Lys Tyr Asn Asp Arg Ala Arg Leu Cys Leu
    1085            1090            1095

Thr Tyr Asp Glu Pro Leu Ser His Leu Ile Tyr Ala Gly Ala Asp
    1100            1105            1110

Phe Ile Leu Val Pro Ser Ile Phe Glu Pro Cys Gly Leu Thr Gln
    1115            1120            1125

Leu Thr Ala Met Arg Tyr Gly Ser Ile Pro Val Val Arg Lys Thr
    1130            1135            1140

Gly Gly Leu Tyr Asp Thr Val Phe Asp Val Asp His Asp Lys Glu
    1145            1150            1155

Arg Ala Gln Gln Cys Gly Leu Glu Pro Asn Gly Phe Ser Phe Asp
    1160            1165            1170

Gly Ala Asp Ala Gly Gly Val Asp Tyr Ala Leu Asn Arg Ala Leu
    1175            1180            1185

Ser Ala Trp Tyr Asp Gly Arg Asp Trp Phe Asn Ser Leu Cys Lys
    1190            1195            1200

Gln Val Met Glu Gln Asp Trp Ser Trp Asn Arg Pro Ala Leu Asp
    1205            1210            1215

Tyr Leu Glu Leu Tyr His Ala Ala Arg Lys Leu Glu
    1220            1225            1230

<210> SEQ ID NO 3
<211> LENGTH: 61
<212> TYPE: PRT
<213> ORGANISM: Solanum tuberosum

<400> SEQUENCE: 3

Arg Ser Phe Thr Thr Arg Leu Thr Glu Thr His Leu Asn Gly Asp Trp
1               5                   10                  15

Trp Ser Cys Lys Ile His Val Pro Lys Glu Ala Tyr Arg Ala Asp Phe
            20                  25                  30

Val Phe Phe Asn Gly Gln Asp Val Tyr Asp Asn Asp Gly Asn Asp
        35                  40                  45

Phe Ser Ile Thr Val Lys Gly Gly Met Gln Ile Ile Asp
    50                  55                  60
```

-continued

```
<210> SEQ ID NO 4
<211> LENGTH: 1641
<212> TYPE: DNA
<213> ORGANISM: Solanum tuberosum

<400> SEQUENCE: 4
atgaagcaca gttcagctat tccgctgtt ttgaccgatg acaattcgac aatggcaccc        60
ctagaggaag atgtcaacac tgaaaatatt ggcctcctaa atttggatcc aactttggaa       120
ccttatctag atcacttcag acacagaatg aagagatatg tggatcagaa aatgctcatt       180
gaaaaatatg agggacccct tgaggaattt gctcaaggtt attaaaaatt tggattcaac       240
agggaagatg gttgcatagt ctatcgtgaa tgggctcctg ctgctcagga agcagaagtt       300
attggcgatt tcaatggtag gaacggttct aaccacatga tggagaagga ccagtttggt       360
gtttggagta ttagaattcc tgatgttgac agtaagccag tcattccaca caactccaga       420
gttaagtttc gtttcaaaca tggtaatgga gtgtgggtag atcgtatccc tgcttggata       480
aagtatgcca ctgcagacgc cacaaagttt gcagcaccat gatggtgt ctactgggac         540 ccaccacctt cagaaaggta ccacttcaaa taccctcgcc ctcccaaacc ccgagcccca       600
cgaatctacg aagcacatgt cggcatgagc agctctgagc acgtgtaaa ttcgtatcgt        660 gagtttgcag atgatgtttt acctcggatt aaggcaaata actataatac tgtccagttg       720
atggccataa tggaacattc ttactatgga tcatttggat atcatgttac aaactttttt       780
gctgtgagca atagatatgg aaacccggag gacctaaagt atctgataga taaagcacat       840
agcttgggtt tacaggttct ggtggatgta gttcacagtc atgcaagcaa taatgtcact       900
gatggcctca atggctttga tattggccaa ggttctcaag aatcctactt tcatgctgga       960
gagcgagggt accataagtt gtgggatagc aggctgttca actatgccaa ttgggaggtt      1020
cttcgtttcc ttctttccaa cttgaggtgg tggctagaag agtataactt tgacggattt      1080
cgatttgatg gaataacttc tatgctgtat gttcatcatg aatcaatat gggatttaca       1140 ggaaactata atgagtattt cagcgaggct acagatgttg atgctgtggt ctatttaatg      1200
ttggccaata atctgattca aagattttc ccagacgcaa ctgttattgc cgaagatgtt       1260
tctggtatgc cgggccttag ccggcctgtt tctgagggag gaattggttt tgattaccgc      1320
ctggcaatgg caatcccaga taagtggata gattatttaa agaataagaa tgatgaagat      1380
tggtccatga aggaagtaac atcgagtttg acaaatagga gatatacaga gaagtgtata      1440
gcatatgcgg agagccatga tcagtctatt gtcggtgaca agaccattgc atttctccta      1500
atgaacaaag agatgtattc tggcatgtct tgcttgacag atgcttctcc tgttgttgat      1560
gcaggaattg cgcttgacaa gatgatccat tttttcaca atggccttgg gaggagaggg      1620
gtacctcaat ttcatgggta a                                                1641

<210> SEQ ID NO 5
<211> LENGTH: 546
<212> TYPE: PRT
<213> ORGANISM: Solanum tuberosum
<300> PUBLICATION INFORMATION:
<308> DATABASE ACCESSION NUMBER: Swiss Prot / P30924
<309> DATABASE ENTRY DATE: 1993-07-26

<400> SEQUENCE: 5

Met Lys His Ser Ser Ala Ile Ser Ala Val Leu Thr Asp Asp Asn Ser
1               5                   10                  15

Thr Met Ala Pro Leu Glu Glu Asp Val Asn Thr Glu Asn Ile Gly Leu
            20                  25                  30
```

```
Leu Asn Leu Asp Pro Thr Leu Glu Pro Tyr Leu Asp His Phe Arg His
         35                  40                  45

Arg Met Lys Arg Tyr Val Asp Gln Lys Met Leu Ile Glu Lys Tyr Glu
 50                  55                  60

Gly Pro Leu Glu Glu Phe Ala Gln Gly Tyr Leu Lys Phe Gly Phe Asn
 65                  70                  75                  80

Arg Glu Asp Gly Cys Ile Val Tyr Arg Glu Trp Ala Pro Ala Ala Gln
                 85                  90                  95

Glu Ala Glu Val Ile Gly Asp Phe Asn Gly Arg Asn Gly Ser Asn His
            100                 105                 110

Met Met Glu Lys Asp Gln Phe Gly Val Trp Ser Ile Arg Ile Pro Asp
        115                 120                 125

Val Asp Ser Lys Pro Val Ile Pro His Asn Ser Arg Val Lys Phe Arg
130                 135                 140

Phe Lys His Gly Asn Gly Val Trp Val Asp Arg Ile Pro Ala Trp Ile
145                 150                 155                 160

Lys Tyr Ala Thr Ala Asp Ala Thr Lys Phe Ala Ala Pro Tyr Asp Gly
                165                 170                 175

Val Tyr Trp Asp Pro Pro Ser Glu Arg Tyr His Phe Lys Tyr Pro
            180                 185                 190

Arg Pro Pro Lys Pro Arg Ala Pro Arg Ile Tyr Glu Ala His Val Gly
        195                 200                 205

Met Ser Ser Glu Pro Arg Val Asn Ser Tyr Arg Glu Phe Ala Asp
210                 215                 220

Asp Val Leu Pro Arg Ile Lys Ala Asn Asn Tyr Asn Thr Val Gln Leu
225                 230                 235                 240

Met Ala Ile Met Glu His Ser Tyr Tyr Gly Ser Phe Gly Tyr His Val
                245                 250                 255

Thr Asn Phe Phe Ala Val Ser Asn Arg Tyr Gly Asn Pro Glu Asp Leu
            260                 265                 270

Lys Tyr Leu Ile Asp Lys Ala His Ser Leu Gly Leu Gln Val Leu Val
        275                 280                 285

Asp Val Val His Ser His Ala Ser Asn Asn Val Thr Asp Gly Leu Asn
290                 295                 300

Gly Phe Asp Ile Gly Gln Gly Ser Gln Glu Ser Tyr Phe His Ala Gly
305                 310                 315                 320

Glu Arg Gly Tyr His Lys Leu Trp Asp Ser Arg Leu Phe Asn Tyr Ala
                325                 330                 335

Asn Trp Glu Val Leu Arg Phe Leu Leu Ser Asn Leu Arg Trp Trp Leu
            340                 345                 350

Glu Glu Tyr Asn Phe Asp Gly Phe Arg Phe Asp Gly Ile Thr Ser Met
        355                 360                 365

Leu Tyr Val His His Gly Ile Asn Met Gly Phe Thr Gly Asn Tyr Asn
370                 375                 380

Glu Tyr Phe Ser Glu Ala Thr Asp Val Asp Ala Val Val Tyr Leu Met
385                 390                 395                 400

Leu Ala Asn Asn Leu Ile His Lys Ile Phe Pro Asp Ala Thr Val Ile
                405                 410                 415

Ala Glu Asp Val Ser Gly Met Pro Gly Leu Ser Arg Pro Val Ser Glu
            420                 425                 430

Gly Gly Ile Gly Phe Asp Tyr Arg Leu Ala Met Ala Ile Pro Asp Lys
        435                 440                 445

Trp Ile Asp Tyr Leu Lys Asn Lys Asn Asp Glu Asp Trp Ser Met Lys
450                 455                 460
```

```
Glu Val Thr Ser Ser Leu Thr Asn Arg Arg Tyr Thr Glu Lys Cys Ile
465                 470                 475                 480

Ala Tyr Ala Glu Ser His Asp Gln Ser Ile Val Gly Asp Lys Thr Ile
            485                 490                 495

Ala Phe Leu Leu Met Asn Lys Glu Met Tyr Ser Gly Met Ser Cys Leu
                500                 505                 510

Thr Asp Ala Ser Pro Val Val Asp Ala Gly Ile Ala Leu Asp Lys Met
            515                 520                 525

Ile His Phe Phe His Asn Gly Leu Gly Arg Arg Gly Val Pro Gln Phe
        530                 535                 540

His Gly
545

<210> SEQ ID NO 6
<211> LENGTH: 1824
<212> TYPE: DNA
<213> ORGANISM: Solanum tuberosum

<400> SEQUENCE: 6
atggcaagca tcacagcttc acaccacttt gtgtcaagaa gccaaacttc actagacacc      60
aaatcaacct tgtcacagat aggactcagg aaccatactc tgactcacaa tggtttaagg     120
gctgttaaca agcttgatgg gctccaatca agaactaata ctaaggtaac acccaagatg     180
gcatccagaa ctgagaccaa gagacctgga tgctcagcta ccattgtttg tggaaaggga     240
atgaacttga tctttgtggg tactgaggtt ggtccttgga gcaaaactgg tggactaggt     300
gatgttcttg gtggactacc accagccctt gcagcccgcg acatcgggt aatgacaata     360 tccccccgtt atgaccaata caagatgct tgggatacta gcgttgcggt tgaggtcaaa     420
gttggagaca gcattgaaat tgttcgtttc tttcactgct ataaacgtgg ggttgatcgt     480
gtttttgttg accacccaat gttcttggag aaagtttggg gcaaaactgg ttcaaaaatc     540
tatggcccca agctggact agattatctg acaatgaac ttaggttcag cttgttgtgt      600
caagcagccc tagaggcacc taaagttttg aatttgaaca gtagcaacta cttctcagga     660
ccatatggag aggatgttct cttcattgcc aatgattggc acacagctct cattccttgc     720
tacttgaagt caatgtacca gtccagagga atctatttga tgccaaggt cgctttctgc      780 atccataaca ttgcctacca aggccgattt tctttctctg acttccctct tctcaatctt     840
cctgatgaat tcaggggttc ttttgatttc attgatggat atgagaagcc tgttaagggt     900
aggaaaatca actggatgaa ggctgggata ttagaatcac atagggtggt tacagtgagc     960
ccatactatg cccaagaact tgtctctgct gttgacaagg tgttgaatt ggacagtgtc     1020 cttcgtaaga cttgcataac tgggattgtg aatggcatgg atacacaaga gtggaaccca    1080
gcgactgaca aatacacaga tgtcaaatac gatataacca ctgtcatgga cgcaaaacct    1140
ttactaaagg aggctcttca agcagcagtt ggcttgcctg ttgacaagaa gatcccttg     1200 attggcttca tcggcagact tgaggagcag aaaggttcag atattcttgt tgctgcaatt    1260
cacaagttca tcggattgga tgttcaaatt gtagtccttg aactggcaa aaaggagttt    1320 gagcaggaga ttgaacagct cgaagtgttg taccctaaca agctaaagg agtggcaaaa    1380 ttcaatgtcc ctttggctca catgatcact gctggtgctg atttatgtt ggttccaagc    1440 agatttgaac cttgtggtct cattcagtta catgctatgc gatatggaac agtgccaatc    1500
tgtgcatcga ctggtggact tgttgacact gtgaaagaag gctatactgg attccatatg    1560
ggagccttca atgttgaatg cgatgttgtt gacccagctg atgtgcttaa gatagtaaca    1620
```

```
acagttgcta gagctcttgc agtctatggc accctcgcat tgctgagat gataaaaaat    1680 tgcatgtcag aggaactctc ctggaaggaa cctgccaaga aatgggagac attgctattg    1740
ggcttaggag cttctggcag tgaacccggt gttgaagggg aagaaatcgc tccacttgcc    1800
aaggaaaatg tagccactcc ctaa                                            1824
```

<210> SEQ ID NO 7
<211> LENGTH: 607
<212> TYPE: PRT
<213> ORGANISM: Solanum tuberosum

<400> SEQUENCE: 7

```
Met Ala Ser Ile Thr Ala Ser His His Phe Val Ser Arg Ser Gln Thr
1               5                   10                  15

Ser Leu Asp Thr Lys Ser Thr Leu Ser Gln Ile Gly Leu Arg Asn His
            20                  25                  30

Thr Leu Thr His Asn Gly Leu Arg Ala Val Asn Lys Leu Asp Gly Leu
        35                  40                  45

Gln Ser Arg Thr Asn Thr Lys Val Thr Pro Lys Met Ala Ser Arg Thr
    50                  55                  60

Glu Thr Lys Arg Pro Gly Cys Ser Ala Thr Ile Val Cys Gly Lys Gly
65                  70                  75                  80

Met Asn Leu Ile Phe Val Gly Thr Glu Val Gly Pro Trp Ser Lys Thr
                85                  90                  95

Gly Gly Leu Gly Asp Val Leu Gly Gly Leu Pro Pro Ala Leu Ala Ala
            100                 105                 110

Arg Gly His Arg Val Met Thr Ile Ser Pro Arg Tyr Asp Gln Tyr Lys
        115                 120                 125

Asp Ala Trp Asp Thr Ser Val Ala Val Glu Val Lys Val Gly Asp Ser
    130                 135                 140

Ile Glu Ile Val Arg Phe Phe His Cys Tyr Lys Arg Gly Val Asp Arg
145                 150                 155                 160

Val Phe Val Asp His Pro Met Phe Leu Glu Lys Val Trp Gly Lys Thr
                165                 170                 175

Gly Ser Lys Ile Tyr Gly Pro Lys Ala Gly Leu Asp Tyr Leu Asp Asn
            180                 185                 190

Glu Leu Arg Phe Ser Leu Leu Cys Gln Ala Ala Leu Glu Ala Pro Lys
        195                 200                 205

Val Leu Asn Leu Asn Ser Asn Tyr Phe Ser Gly Pro Tyr Gly Glu
    210                 215                 220

Asp Val Leu Phe Ile Ala Asn Asp Trp His Thr Ala Leu Ile Pro Cys
225                 230                 235                 240

Tyr Leu Lys Ser Met Tyr Gln Ser Arg Gly Ile Tyr Leu Asn Ala Lys
                245                 250                 255

Val Ala Phe Cys Ile His Asn Ile Ala Tyr Gln Gly Arg Phe Ser Phe
            260                 265                 270

Ser Asp Phe Pro Leu Leu Asn Leu Pro Asp Glu Phe Arg Gly Ser Phe
        275                 280                 285

Asp Phe Ile Asp Gly Tyr Glu Lys Pro Val Lys Gly Arg Lys Ile Asn
    290                 295                 300

Trp Met Lys Ala Gly Ile Leu Glu Ser His Arg Val Val Thr Val Ser
305                 310                 315                 320

Pro Tyr Tyr Ala Gln Glu Leu Val Ser Ala Val Asp Lys Gly Val Glu
                325                 330                 335
```

Leu Asp Ser Val Leu Arg Lys Thr Cys Ile Thr Gly Ile Val Asn Gly
                340                 345                 350

Met Asp Thr Gln Glu Trp Asn Pro Ala Thr Asp Lys Tyr Thr Asp Val
                355                 360                 365

Lys Tyr Asp Ile Thr Thr Val Met Asp Ala Lys Pro Leu Leu Lys Glu
            370                 375                 380

Ala Leu Gln Ala Ala Val Gly Leu Pro Val Asp Lys Lys Ile Pro Leu
385                 390                 395                 400

Ile Gly Phe Ile Gly Arg Leu Glu Glu Gln Lys Gly Ser Asp Ile Leu
                405                 410                 415

Val Ala Ala Ile His Lys Phe Ile Gly Leu Asp Val Gln Ile Val Val
                420                 425                 430

Leu Gly Thr Gly Lys Lys Glu Phe Glu Gln Glu Ile Glu Gln Leu Glu
            435                 440                 445

Val Leu Tyr Pro Asn Lys Ala Lys Gly Val Ala Lys Phe Asn Val Pro
450                 455                 460

Leu Ala His Met Ile Thr Ala Gly Ala Asp Phe Met Leu Val Pro Ser
465                 470                 475                 480

Arg Phe Glu Pro Cys Gly Leu Ile Gln Leu His Ala Met Arg Tyr Gly
                485                 490                 495

Thr Val Pro Ile Cys Ala Ser Thr Gly Gly Leu Val Asp Thr Val Lys
                500                 505                 510

Glu Gly Tyr Thr Gly Phe His Met Gly Ala Phe Asn Val Glu Cys Asp
            515                 520                 525

Val Val Asp Pro Ala Asp Val Leu Lys Ile Val Thr Thr Val Ala Arg
530                 535                 540

Ala Leu Ala Val Tyr Gly Thr Leu Ala Phe Ala Glu Met Ile Lys Asn
545                 550                 555                 560

Cys Met Ser Glu Glu Leu Ser Trp Lys Glu Pro Ala Lys Lys Trp Glu
                565                 570                 575

Thr Leu Leu Leu Gly Leu Gly Ala Ser Gly Ser Glu Pro Gly Val Glu
            580                 585                 590

Gly Glu Glu Ile Ala Pro Leu Ala Lys Glu Asn Val Ala Thr Pro
            595                 600                 605

<210> SEQ ID NO 8
<211> LENGTH: 31
<212> TYPE: DNA
<213> ORGANISM: Artificial sequence
<220> FEATURE:
<223> OTHER INFORMATION: Oligonucleotide

<400> SEQUENCE: 8
gatgggtacc agcacttcta cttggcagag g                                    31

<210> SEQ ID NO 9
<211> LENGTH: 1004
<212> TYPE: DNA
<213> ORGANISM: Solanum tuberosum

<400> SEQUENCE: 9
tcaaactagt cacaaccagt ccatttctgg aggtcgttcc ttcgcagaaa tactgattgg     60
taactccttg gggaaatcct ccatatcaca agagtcatta cttagaggct gctcgttaca    120
caagatgatc agattaatta catctacaat tggtggtcat gcatacctca acttcatggg    180
caatgaattt ggtcacccaa agagagtaga gtttccaatg tcaagcaaca atttctcctt    240
ttcactggct aaccgtcgct gggatctatt ggaagatgtt gtacattatc aattgttctc    300

-continued

```
atttgataag ggtatgatgg acttggataa aaatgggaga attttgtcca gaggtcttgc    360
caacattcac catgtcaatg atactaccat ggtgatttct tacttgagag gtcccaatct    420
ctttgtgttc aactttcatc ctgtcaattc atatgaaaga tacattatag gtgtggaaga    480
agctggagag tatcaagtca cattaaatac agatgaaaac aagtatggtg gtagaggact    540
acttggccat gatcagaata ttcaaagaac cattagtaga agagctgatg gaatgagatt    600
ttgcttggaa gtgcctctgc caagtagaag tgctcaggtc tacaagttga cccgaattct    660
aagagcatga tcactctagt aatcaaagtg cctcatatga tgacacaaaa ggaaaggttc    720
tacattgccc ttacactgat caatattgac acctttccga ggtgagtttc tgtgattctt    780
gagcagactg ttggctagtc aattatcatg aacttttgcc ttcagcatcc ggatagtcgc    840
ttctcctgtg caatgagggc atggacgaat ttttttttgg cttgtcatgg gggtcataag    900
catccgccag attaagattt cacaggcctc gagtaaaacc atcacttact taaggatac     960 acaaacacac caacggggtg caggctctga taccttctaa agtg                    1004
```

<210> SEQ ID NO 10
<211> LENGTH: 2096
<212> TYPE: DNA
<213> ORGANISM: Solanum tuberosum

<400> SEQUENCE: 10

```
aacaatgctc tctctgtcgg attcaattcg aatttcttca ccattgagcg attctcgtct     60
tagttttcta tctcaaaccg gaagcagaac cagtcgccag cttaaatttg ttcgcagccg    120
ccgggctcga gtttcgaggt gtagatgctc agcaacggag caaccgccac cgcaacgacg    180
gaagcaacga ccggagaagt acaaacagtc ggaggaaggg aaaggaatcg atcctgttgg    240
atttctcagc aaatacggca ttactcataa agcgtttgct caatttcttc gtgaaagata    300
taaatcattg aaggacttga aggatgaaat attgactcgt catttcagtc tcaaggagat    360
gtctactggg tatgaattaa tgggtatgca tcgcaacata caacatcgag tggatttctt    420
ggaatgggct ccaggtgctc gctactgtgc tctgattggt gacttcaatg ggtggtcaac    480
aactggtaac tgtgccagag agggtcattt tggtcatgac gattatgggt attggtttat    540
tattcttgaa gataaaattac gtgaaggaga agaacctgat aaattgtatt ttcaacagta    600
caattatgcg gaggactatg gtaaaggtga cacgggtatt accgtcgagg aaatctttaa    660
aaaagcaaat gatgagtatt gggaacctgg agaagatcgc ttcattaaat cacgttatga    720
ggtggcagca aagttatatg aggaaatgtt cggaccaaat ggacctcaaa cagaagagga    780
actagaagca atgcctgatg cagctacacg atacaaaact tggaaagagc aacaaaaaga    840
ggatccggca agcaatttgc catcgtatga tgtggtagat agtggaaaag aatatgatat    900
ttacaatatt ataggtgatc ctgaatcgtt taagaaattt cgtatgaaac agcctcctat    960
tgcttactgg ttagaaacta aaaagggaag gaaaggctgg ttacagaaat atatgcctgc   1020
tttacctcat ggaagcaaat acagggtgta ttttaacaca ccaaatgggc tcttgaacg    1080 agttcctgcg tgggccaatt ttgtcattcc agatgcaggc gggatggcat tagcagtcca   1140
ttgggaacca cctcctgaat atgcttataa atggaaacac aagctaccag tcaagcctaa   1200
gtccttgcgc atatatgaat gtcatgttgg catctctggc caggaaccaa agtttttcatc   1260 tttcaatgat tttattagca aggtccttcc gcatgtaaaa gaagctggat acaatgcaat   1320
acaaattatt ggagttgttg agcacaagga ttatttcact gttggatata gagtgaccaa   1380 ttttttatgct gttagtagcc gttatggcac accggatgac ttcaagcgct tggttgatga   1440
```

```
agcacatggg cttggactgc ttgtcttttt ggagattgtg cactcttatg cagcagcaga    1500
tgaaatggtt gggttatctc tttttgatgg agcaaatgat tgctatttcc acactggtaa    1560
acgtggacac cacaaattct ggggcacacg gatgttcaaa tatggagatc ttgatgttct    1620
gcactttctt ctttcaaatc tgaactggtg ggtggaggag tatcatgtcg atggcttcca    1680
ttttcattcg ctctcgtcca tgttgtatac gcataatgga tttgcttcat ttactggtga    1740
catggatgaa tactgtaacc aatatgttga caaggaggcc ttattgtacc tcatattagc    1800
aaatgaagta ttacatgctc ttcatcctaa tgtgatcacg attgctgagg atgcaactct    1860
gtatcctgga ctctgcgatc caacatctca aggtggactg ggctttgatt attttgccaa    1920
tctttctgcc tcagagatgt ggcttgcatt acttgaaaat actcctgatc atgaatggtg    1980
catgagtaag attgttagca cattagtggg cgatagacaa aatactgata aaatgctttt    2040
gtatgcagaa aatcacaacc agtccatttc tggaggtcgt tccttcgcag aaatac        2096
```

<210> SEQ ID NO 11
<211> LENGTH: 3204
<212> TYPE: DNA
<213> ORGANISM: Solanum tuberosum
<220> FEATURE:
<221> NAME/KEY: CDS
<222> LOCATION: (99)..(2804)
<223> OTHER INFORMATION: Solanum tuberosum (cv Desiree) protein

<400> SEQUENCE: 11

```
gaattgtaat acgactcact atagggcgaa ttgggccctc tagatgcatg ctcgagcggc     60
cgccagtgtg atggatatct gcagaattcg cttaaca atg ctc tct ctg tcg gat    116
                                          Met Leu Ser Leu Ser Asp
                                          1               5 tca att cga att tct tca cca ttg agc gat tct cgt ctt agt ttt cta     164
Ser Ile Arg Ile Ser Ser Pro Leu Ser Asp Ser Arg Leu Ser Phe Leu
        10                  15                  20 tct caa acc gga agc aga acc agt cgc cag ctt aaa ttt gtt cgc agc     212
Ser Gln Thr Gly Ser Arg Thr Ser Arg Gln Leu Lys Phe Val Arg Ser
    25                  30                  35 cgc cgg gct cga gtt tcg agg tgt aga tgc tca gca acg gag caa ccg     260
Arg Arg Ala Arg Val Ser Arg Cys Arg Cys Ser Ala Thr Glu Gln Pro
40                  45                  50 cca ccg caa cga cgg aag caa cga ccg gag aag tac aaa cag tcg gag     308
Pro Pro Gln Arg Arg Lys Gln Arg Pro Glu Lys Tyr Lys Gln Ser Glu
55                  60                  65                  70 gaa gag aaa gga atc gat cct gtt gga ttt ctc agc aaa tac ggc att     356
Glu Glu Lys Gly Ile Asp Pro Val Gly Phe Leu Ser Lys Tyr Gly Ile
                75                  80                  85 act cat aaa gcg ttt gct caa ttt ctt cgt gaa aga tat aaa tca ttg     404
Thr His Lys Ala Phe Ala Gln Phe Leu Arg Glu Arg Tyr Lys Ser Leu
            90                  95                  100 aag gac ttg aag gat gaa ata ttg act cgt cat ttc agt ctc aag gag     452
Lys Asp Leu Lys Asp Glu Ile Leu Thr Arg His Phe Ser Leu Lys Glu
        105                 110                 115 atg tct act ggg tat gaa tta atg ggt atg cat cgc aac ata caa cat     500
Met Ser Thr Gly Tyr Glu Leu Met Gly Met His Arg Asn Ile Gln His
    120                 125                 130 cga gtg gat ttc ttg gaa tgg gct cca ggt gct cgc tac tgt gct ctg     548
Arg Val Asp Phe Leu Glu Trp Ala Pro Gly Ala Arg Tyr Cys Ala Leu
135                 140                 145                 150 att ggt gac ttc aat ggg tgg tca aca act ggt aac tgt gcc aga gag     596
Ile Gly Asp Phe Asn Gly Trp Ser Thr Thr Gly Asn Cys Ala Arg Glu
                155                 160                 165
```

```
ggt cat ttt ggt cat gac gat tat ggg tat tgg ttt att att ctt gaa    644
Gly His Phe Gly His Asp Asp Tyr Gly Tyr Trp Phe Ile Ile Leu Glu
        170                 175                 180 gat aaa tta cgt gaa gga gaa gaa cct gat aaa ttg tat ttt caa cag    692
Asp Lys Leu Arg Glu Gly Glu Glu Pro Asp Lys Leu Tyr Phe Gln Gln
            185                 190                 195 tac aat tat gcg gag gac tat gat aaa ggt gac acg ggt att acc gtc    740
Tyr Asn Tyr Ala Glu Asp Tyr Asp Lys Gly Asp Thr Gly Ile Thr Val
200                 205                 210 gag gaa atc ttt aaa aaa gca aat gat gag tat tgg gaa cct gga gaa    788
Glu Glu Ile Phe Lys Lys Ala Asn Asp Glu Tyr Trp Glu Pro Gly Glu
215                 220                 225                 230 gat cgc ttc att aaa tca cgt tat gag gtg gca gca aag tta tat gag    836
Asp Arg Phe Ile Lys Ser Arg Tyr Glu Val Ala Ala Lys Leu Tyr Glu
                235                 240                 245 gaa atg ttc gga cca aat gga cct caa aca gaa gag gaa cta gaa gca    884
Glu Met Phe Gly Pro Asn Gly Pro Gln Thr Glu Glu Glu Leu Glu Ala
            250                 255                 260 atg cct gat gca gct aca cga tac aaa act tgg aaa gag caa caa aaa    932
Met Pro Asp Ala Ala Thr Arg Tyr Lys Thr Trp Lys Glu Gln Gln Lys
        265                 270                 275 aag gat ccg gca agc aat ttg cca tcg tat gat gtg gta gat agt gga    980
Lys Asp Pro Ala Ser Asn Leu Pro Ser Tyr Asp Val Val Asp Ser Gly
    280                 285                 290 aaa gaa tat gat att tac aat att ata ggt gat cct gaa tcg ttt aag   1028
Lys Glu Tyr Asp Ile Tyr Asn Ile Ile Gly Asp Pro Glu Ser Phe Lys
295                 300                 305                 310 aaa ttt cgt atg aaa cag cct cct att gct tac tgg tta gaa act aaa   1076
Lys Phe Arg Met Lys Gln Pro Pro Ile Ala Tyr Trp Leu Glu Thr Lys
                315                 320                 325 aag gga agg aaa ggc tgg tta cag aaa tat atg cct gct tta cct cat   1124
Lys Gly Arg Lys Gly Trp Leu Gln Lys Tyr Met Pro Ala Leu Pro His
            330                 335                 340 gga agc aaa cac agg gtg tat ttt aac aca cca aat ggg cct ctt gaa   1172
Gly Ser Lys His Arg Val Tyr Phe Asn Thr Pro Asn Gly Pro Leu Glu
        345                 350                 355 cga gtt cct gcg tgg gcc aat ttt gtc att cca gat gca gac ggg atg   1220
Arg Val Pro Ala Trp Ala Asn Phe Val Ile Pro Asp Ala Asp Gly Met
    360                 365                 370 gca tta gca gtc cat tgg gaa cca cct cct gaa tat gct tat aaa tgg   1268
Ala Leu Ala Val His Trp Glu Pro Pro Pro Glu Tyr Ala Tyr Lys Trp
375                 380                 385                 390 aaa cac aag cta cca gtc aag cct aag tcc ttg cgc ata tat gaa tgt   1316
Lys His Lys Leu Pro Val Lys Pro Lys Ser Leu Arg Ile Tyr Glu Cys
                395                 400                 405 cat gtt ggc atc tct ggc cag gaa cca aaa gtt tca tct ttc aat gat   1364
His Val Gly Ile Ser Gly Gln Glu Pro Lys Val Ser Ser Phe Asn Asp
            410                 415                 420 ttt att agc aag gtc ctt ccg cat gta aaa gaa gct gga tac aat gca   1412
Phe Ile Ser Lys Val Leu Pro His Val Lys Glu Ala Gly Tyr Asn Ala
        425                 430                 435 acg caa att att gga gtt gtt gag cac aag gat tat ttc act gtt gga   1460
Thr Gln Ile Ile Gly Val Val Glu His Lys Asp Tyr Phe Thr Val Gly
    440                 445                 450 tat aga gtg acc aat ttt tat gct gtt agt agc cgt tat ggc aca ccg   1508
Tyr Arg Val Thr Asn Phe Tyr Ala Val Ser Ser Arg Tyr Gly Thr Pro
455                 460                 465                 470 gat gac ttc aag cgc ttg gtt gat gaa gca cat ggg ctt gga ctg ctt   1556
Asp Asp Phe Lys Arg Leu Val Asp Glu Ala His Gly Leu Gly Leu Leu
                475                 480                 485
```

```
gtc ttt ttg gag att gtg cac tcc tat gca gca gca gat gaa atg gtt      1604
Val Phe Leu Glu Ile Val His Ser Tyr Ala Ala Ala Asp Glu Met Val
        490                 495                 500 ggg tta tct ctt ttt gat gga gca aat gat tgc tat ttc cac act ggt      1652
Gly Leu Ser Leu Phe Asp Gly Ala Asn Asp Cys Tyr Phe His Thr Gly
            505                 510                 515 aaa cgt gga cac cac aaa ttc tgg ggc aca cgg atg ttc aaa tat gga      1700
Lys Arg Gly His His Lys Phe Trp Gly Thr Arg Met Phe Lys Tyr Gly
520                 525                 530 gat cct gat gtt ctg cac ttt ctt ctt tca aat ctg aac tgg tgg gtg      1748
Asp Pro Asp Val Leu His Phe Leu Leu Ser Asn Leu Asn Trp Trp Val
535                 540                 545                 550 gag gag tat cat gtc gat ggc ttc cat ttt cat tcg ctc tcg tcc atg      1796
Glu Glu Tyr His Val Asp Gly Phe His Phe His Ser Leu Ser Ser Met
                555                 560                 565 ttg tat acg cat aat gga ttt gct tca ttt act ggt gac atg gat gaa      1844
Leu Tyr Thr His Asn Gly Phe Ala Ser Phe Thr Gly Asp Met Asp Glu
            570                 575                 580 tac tgt aac caa tat gtt gac aag gag gcc tta ttg tac ctc ata tta      1892
Tyr Cys Asn Gln Tyr Val Asp Lys Glu Ala Leu Leu Tyr Leu Ile Leu
        585                 590                 595 gca aat gaa gta tta cat gct ctt cat cct aat gtg atc acg att gct      1940
Ala Asn Glu Val Leu His Ala Leu His Pro Asn Val Ile Thr Ile Ala
600                 605                 610 gtg gat gca act ctg tat cct gga ctc tgc gat cca aca tct caa ggt      1988
Val Asp Ala Thr Leu Tyr Pro Gly Leu Cys Asp Pro Thr Ser Gln Gly
615                 620                 625                 630 gga ctg ggc ttt gat tat ttt gcc aat ctt tct gcc tca gag atg tgg      2036
Gly Leu Gly Phe Asp Tyr Phe Ala Asn Leu Ser Ala Ser Glu Met Trp
                635                 640                 645 ctt gca tta ctt gaa aat act cct gat cat gaa tgg tgc atg agt aag      2084
Leu Ala Leu Leu Glu Asn Thr Pro Asp His Glu Trp Cys Met Ser Lys
            650                 655                 660 att gtt agc aca tta gtg ggc gat aga caa aat act gat aaa atg ctt      2132
Ile Val Ser Thr Leu Val Gly Asp Arg Gln Asn Thr Asp Lys Met Leu
        665                 670                 675 ttg tat gca gaa aat cac aac cag tcc att tct gga ggt cgt tcc ttc      2180
Leu Tyr Ala Glu Asn His Asn Gln Ser Ile Ser Gly Gly Arg Ser Phe
680                 685                 690 gca gaa ata ctg att ggt aac tcc ttg ggg aaa tct tcc ata tca caa      2228
Ala Glu Ile Leu Ile Gly Asn Ser Leu Gly Lys Ser Ser Ile Ser Gln
695                 700                 705                 710 gag tca tta ctt aga ggc tgc tcg tta cac aag atg atc aga tta att      2276
Glu Ser Leu Leu Arg Gly Cys Ser Leu His Lys Met Ile Arg Leu Ile
                715                 720                 725 aca tct aca att ggt ggt cat gca tac ctc aac ttc atg ggc aat gaa      2324
Thr Ser Thr Ile Gly Gly His Ala Tyr Leu Asn Phe Met Gly Asn Glu
            730                 735                 740 ttt ggt cac cca aag aga gta gag ttt cca atg tca agc aac aat ttc      2372
Phe Gly His Pro Lys Arg Val Glu Phe Pro Met Ser Ser Asn Asn Phe
        745                 750                 755 tcc ttt tca ctg gct aac cgt cgc tgg gat cta ttg gaa gat gtt gta      2420
Ser Phe Ser Leu Ala Asn Arg Arg Trp Asp Leu Leu Glu Asp Val Val
760                 765                 770 cat tat caa tta ttc tca ttt gat aag gat atg atg gac ttg gat aaa      2468
His Tyr Gln Leu Phe Ser Phe Asp Lys Asp Met Met Asp Leu Asp Lys
775                 780                 785                 790 aat ggg aga att ttg tcc aga ggt ctt gcc aac att cac cat gtc aat      2516
Asn Gly Arg Ile Leu Ser Arg Gly Leu Ala Asn Ile His His Val Asn
                795                 800                 805
```

```
gat act acc atg gtg att tct tac ttg aga ggt ccc aat ctc ttt gtg    2564
Asp Thr Thr Met Val Ile Ser Tyr Leu Arg Gly Pro Asn Leu Phe Val
        810                 815                 820 ttc aac ttt cat cct gtc aat tca tat gaa aga tac att ata ggt gtg    2612
Phe Asn Phe His Pro Val Asn Ser Tyr Glu Arg Tyr Ile Ile Gly Val
    825                 830                 835 gaa gaa gct gga gag tat caa gtc aca tta aat aca gat gaa aac aag    2660
Glu Glu Ala Gly Glu Tyr Gln Val Thr Leu Asn Thr Asp Glu Asn Lys
840                 845                 850 tat ggt ggt aga gga cta ctt ggc cat gat cag aat act caa aga acc    2708
Tyr Gly Gly Arg Gly Leu Leu Gly His Asp Gln Asn Thr Gln Arg Thr
855                 860                 865                 870 att agt aga aga gct gat gga atg aga ttt tgc ttg gaa gta cct ctg    2756
Ile Ser Arg Arg Ala Asp Gly Met Arg Phe Cys Leu Glu Val Pro Leu
            875                 880                 885 cca agt aga agt gct cag gtc tac aag ttg acc cga att cta aga gca    2804
Pro Ser Arg Ser Ala Gln Val Tyr Lys Leu Thr Arg Ile Leu Arg Ala
        890                 895                 900 tgatcactct agcaatcaaa gtgcctcata tgatcacaca aaagggaagg ttctacattg    2864
cccttatact gaccaatatt gtggcctttc cgaggtgagt ttctgtgatt cttgagcaca    2924
ggctgttggc tagtcagtta tcatgaactt ttgccttcag catctggata agcgcttctc    2984
ctgtgcaatg agggcatgga cgaaattttt ttggttcgtc atgggagtca aaagcatctg    3044
ccagattaag atttcacagg cctcgagtaa aaccatcact tacttaggat acacaaacac    3104
atcaacgggg tgcaggctct gataccttct aaagtgaagc cgaattccag cacactggcg    3164
gccgttacta gtggatccga gctcggtacc aagcttggcg                          3204
```

<210> SEQ ID NO 12
<211> LENGTH: 902
<212> TYPE: PRT
<213> ORGANISM: Solanum tuberosum

<400> SEQUENCE: 12

```
Met Leu Ser Leu Ser Asp Ser Ile Arg Ile Ser Ser Pro Leu Ser Asp
1               5                   10                  15

Ser Arg Leu Ser Phe Leu Ser Gln Thr Gly Ser Arg Thr Ser Arg Gln
            20                  25                  30

Leu Lys Phe Val Arg Ser Arg Ala Arg Val Ser Arg Cys Arg Cys
        35                  40                  45

Ser Ala Thr Glu Gln Pro Pro Gln Arg Arg Lys Gln Arg Pro Glu
    50                  55                  60

Lys Tyr Lys Gln Ser Glu Glu Lys Gly Ile Asp Pro Val Gly Phe
65                  70                  75                  80

Leu Ser Lys Tyr Gly Ile Thr His Lys Ala Phe Ala Gln Phe Leu Arg
                85                  90                  95

Glu Arg Tyr Lys Ser Leu Lys Asp Leu Lys Asp Glu Ile Leu Thr Arg
            100                 105                 110

His Phe Ser Leu Lys Glu Met Ser Thr Gly Tyr Glu Leu Met Gly Met
        115                 120                 125

His Arg Asn Ile Gln His Arg Val Asp Phe Leu Glu Trp Ala Pro Gly
    130                 135                 140

Ala Arg Tyr Cys Ala Leu Ile Gly Asp Phe Asn Gly Trp Ser Thr Thr
145                 150                 155                 160

Gly Asn Cys Ala Arg Glu Gly His Phe Gly His Asp Asp Tyr Gly Tyr
                165                 170                 175
```

-continued

```
Trp Phe Ile Ile Leu Glu Asp Lys Leu Arg Glu Gly Glu Glu Pro Asp
            180                 185                 190
Lys Leu Tyr Phe Gln Gln Tyr Asn Tyr Ala Glu Asp Tyr Asp Lys Gly
        195                 200                 205
Asp Thr Gly Ile Thr Val Glu Glu Ile Phe Lys Lys Ala Asn Asp Glu
    210                 215                 220
Tyr Trp Glu Pro Gly Glu Asp Arg Phe Ile Lys Ser Arg Tyr Glu Val
225                 230                 235                 240
Ala Ala Lys Leu Tyr Glu Glu Met Phe Gly Pro Asn Gly Pro Gln Thr
                245                 250                 255
Glu Glu Glu Leu Glu Ala Met Pro Asp Ala Ala Thr Arg Tyr Lys Thr
            260                 265                 270
Trp Lys Glu Gln Gln Lys Lys Asp Pro Ala Ser Asn Leu Pro Ser Tyr
        275                 280                 285
Asp Val Val Asp Ser Gly Lys Glu Tyr Asp Ile Tyr Asn Ile Ile Gly
    290                 295                 300
Asp Pro Glu Ser Phe Lys Lys Phe Arg Met Lys Gln Pro Pro Ile Ala
305                 310                 315                 320
Tyr Trp Leu Glu Thr Lys Lys Gly Arg Lys Gly Trp Leu Gln Lys Tyr
                325                 330                 335
Met Pro Ala Leu Pro His Gly Ser Lys His Arg Val Tyr Phe Asn Thr
            340                 345                 350
Pro Asn Gly Pro Leu Glu Arg Val Pro Ala Trp Ala Asn Phe Val Ile
        355                 360                 365
Pro Asp Ala Asp Gly Met Ala Leu Ala Val His Trp Glu Pro Pro Pro
    370                 375                 380
Glu Tyr Ala Tyr Lys Trp Lys His Lys Leu Pro Val Lys Pro Lys Ser
385                 390                 395                 400
Leu Arg Ile Tyr Glu Cys His Val Gly Ile Ser Gly Gln Glu Pro Lys
                405                 410                 415
Val Ser Ser Phe Asn Asp Phe Ile Ser Lys Val Leu Pro His Val Lys
            420                 425                 430
Glu Ala Gly Tyr Asn Ala Thr Gln Ile Ile Gly Val Val Glu His Lys
        435                 440                 445
Asp Tyr Phe Thr Val Gly Tyr Arg Val Thr Asn Phe Tyr Ala Val Ser
    450                 455                 460
Ser Arg Tyr Gly Thr Pro Asp Asp Phe Lys Arg Leu Val Asp Glu Ala
465                 470                 475                 480
His Gly Leu Gly Leu Leu Val Phe Leu Glu Ile Val His Ser Tyr Ala
                485                 490                 495
Ala Ala Asp Glu Met Val Gly Leu Ser Leu Phe Asp Gly Ala Asn Asp
            500                 505                 510
Cys Tyr Phe His Thr Gly Lys Arg Gly His His Lys Phe Trp Gly Thr
        515                 520                 525
Arg Met Phe Lys Tyr Gly Asp Pro Asp Val Leu His Phe Leu Leu Ser
    530                 535                 540
Asn Leu Asn Trp Trp Val Glu Glu Tyr His Val Asp Gly Phe His Phe
545                 550                 555                 560
His Ser Leu Ser Ser Met Leu Tyr Thr His Asn Gly Phe Ala Ser Phe
                565                 570                 575
Thr Gly Asp Met Asp Glu Tyr Cys Asn Gln Tyr Val Asp Lys Glu Ala
            580                 585                 590
Leu Leu Tyr Leu Ile Leu Ala Asn Glu Val Leu His Ala Leu His Pro
        595                 600                 605
```

```
Asn Val Ile Thr Ile Ala Val Asp Ala Thr Leu Tyr Pro Gly Leu Cys
    610                 615                 620

Asp Pro Thr Ser Gln Gly Gly Leu Gly Phe Asp Tyr Phe Ala Asn Leu
625                 630                 635                 640

Ser Ala Ser Glu Met Trp Leu Ala Leu Leu Glu Asn Thr Pro Asp His
                645                 650                 655

Glu Trp Cys Met Ser Lys Ile Val Ser Thr Leu Val Gly Asp Arg Gln
            660                 665                 670

Asn Thr Asp Lys Met Leu Leu Tyr Ala Glu Asn His Asn Gln Ser Ile
        675                 680                 685

Ser Gly Gly Arg Ser Phe Ala Glu Ile Leu Ile Gly Asn Ser Leu Gly
    690                 695                 700

Lys Ser Ser Ile Ser Gln Glu Ser Leu Leu Arg Gly Cys Ser Leu His
705                 710                 715                 720

Lys Met Ile Arg Leu Ile Thr Ser Thr Ile Gly Gly His Ala Tyr Leu
                725                 730                 735

Asn Phe Met Gly Asn Glu Phe Gly His Pro Lys Arg Val Glu Phe Pro
            740                 745                 750

Met Ser Ser Asn Asn Phe Ser Phe Ser Leu Ala Asn Arg Arg Trp Asp
        755                 760                 765

Leu Leu Glu Asp Val Val His Tyr Gln Leu Phe Ser Phe Asp Lys Asp
    770                 775                 780

Met Met Asp Leu Asp Lys Asn Gly Arg Ile Leu Ser Arg Gly Leu Ala
785                 790                 795                 800

Asn Ile His His Val Asn Asp Thr Thr Met Val Ile Ser Tyr Leu Arg
                805                 810                 815

Gly Pro Asn Leu Phe Val Phe Asn Phe His Pro Val Asn Ser Tyr Glu
            820                 825                 830

Arg Tyr Ile Ile Gly Val Glu Glu Ala Gly Glu Tyr Gln Val Thr Leu
        835                 840                 845

Asn Thr Asp Glu Asn Lys Tyr Gly Gly Arg Gly Leu Leu Gly His Asp
    850                 855                 860

Gln Asn Thr Gln Arg Thr Ile Ser Arg Arg Ala Asp Gly Met Arg Phe
865                 870                 875                 880

Cys Leu Glu Val Pro Leu Pro Ser Arg Ser Ala Gln Val Tyr Lys Leu
                885                 890                 895

Thr Arg Ile Leu Arg Ala
            900

<210> SEQ ID NO 13
<211> LENGTH: 3047
<212> TYPE: DNA
<213> ORGANISM: Solanum tuberosum
<220> FEATURE:
<221> NAME/KEY: CDS
<222> LOCATION: (5)..(2710)
<223> OTHER INFORMATION: Solanum tuberosum (cv Desiree) protein

<400> SEQUENCE: 13 aaca atg ctc tct ctg tcg gat tca att cga att tct tca cca ttg agc      49
     Met Leu Ser Leu Ser Asp Ser Ile Arg Ile Ser Ser Pro Leu Ser
     1               5                   10                  15 gat tct cgt ctt agt ttt cta tct caa acc gga agc aga acc agt cgc      97
Asp Ser Arg Leu Ser Phe Leu Ser Gln Thr Gly Ser Arg Thr Ser Arg
                20                  25                  30 cag ctt aaa ttt gtt cgc agc cgc cgg gct cga gtt tcg agg tgt aga     145
Gln Leu Lys Phe Val Arg Ser Arg Arg Ala Arg Val Ser Arg Cys Arg
```

```
                           35                  40                  45
tgc tca gca acg gag caa ccg cca ccg caa cga cgg aag caa cga ccg       193
Cys Ser Ala Thr Glu Gln Pro Pro Pro Gln Arg Arg Lys Gln Arg Pro
         50                  55                  60 gag aag tac aaa cag tcg gag gaa ggg aaa gga atc gat cct gtt gga       241
Glu Lys Tyr Lys Gln Ser Glu Glu Gly Lys Gly Ile Asp Pro Val Gly
 65                  70                  75 ttt ctc agc aaa tac ggc att act cat aaa gcg ttt gct caa ttt ctt       289
Phe Leu Ser Lys Tyr Gly Ile Thr His Lys Ala Phe Ala Gln Phe Leu
 80                  85                  90                  95 cgt gaa aga tat aaa tca ttg aag gac ttg aag gat gaa ata ttg act       337
Arg Glu Arg Tyr Lys Ser Leu Lys Asp Leu Lys Asp Glu Ile Leu Thr
             100                 105                 110 cgt cat ttc agt ctc aag gag atg tct act ggg tat gaa tta atg ggt       385
Arg His Phe Ser Leu Lys Glu Met Ser Thr Gly Tyr Glu Leu Met Gly
             115                 120                 125 atg cat cgc aac ata caa cat cga gtg gat ttc ttg gaa tgg gct cca       433
Met His Arg Asn Ile Gln His Arg Val Asp Phe Leu Glu Trp Ala Pro
             130                 135                 140 ggt gct cgc tac tgt gct ctg att ggt gac ttc aat ggg tgg tca aca       481
Gly Ala Arg Tyr Cys Ala Leu Ile Gly Asp Phe Asn Gly Trp Ser Thr
     145                 150                 155 act ggt aac tgt gcc aga gag ggt cat ttt ggt cat gac gat tat ggg       529
Thr Gly Asn Cys Ala Arg Glu Gly His Phe Gly His Asp Asp Tyr Gly
160                 165                 170                 175 tat tgg ttt att att ctt gaa gat aaa tta cgt gaa gga gaa gaa cct       577
Tyr Trp Phe Ile Ile Leu Glu Asp Lys Leu Arg Glu Gly Glu Glu Pro
                 180                 185                 190 gat aaa ttg tat ttt caa cag tac aat tat gcg gag gac tat ggt aaa       625
Asp Lys Leu Tyr Phe Gln Gln Tyr Asn Tyr Ala Glu Asp Tyr Gly Lys
                 195                 200                 205 ggt gac acg ggt att acc gtc gag gaa atc ttt aaa aaa gca aat gat       673
Gly Asp Thr Gly Ile Thr Val Glu Glu Ile Phe Lys Lys Ala Asn Asp
     210                 215                 220 gag tat tgg gaa cct gga gaa gat cgc ttc att aaa tca cgt tat gag       721
Glu Tyr Trp Glu Pro Gly Glu Asp Arg Phe Ile Lys Ser Arg Tyr Glu
 225                 230                 235 gtg gca gca aag tta tat gag gaa atg ttc gga cca aat gga cct caa       769
Val Ala Ala Lys Leu Tyr Glu Glu Met Phe Gly Pro Asn Gly Pro Gln
240                 245                 250                 255 aca gaa gag gaa cta gaa gca atg cct gat gca gct aca cga tac aaa       817
Thr Glu Glu Glu Leu Glu Ala Met Pro Asp Ala Ala Thr Arg Tyr Lys
                 260                 265                 270 act tgg aaa gag caa caa aaa gag gat ccg gca agc aat ttg cca tcg       865
Thr Trp Lys Glu Gln Gln Lys Glu Asp Pro Ala Ser Asn Leu Pro Ser
                 275                 280                 285 tat gat gtg gta gat agt gga aaa gaa tat gat att tac aat att ata       913
Tyr Asp Val Val Asp Ser Gly Lys Glu Tyr Asp Ile Tyr Asn Ile Ile
     290                 295                 300 ggt gat cct gaa tcg ttt aag aaa ttt cgt atg aaa cag cct cct att       961
Gly Asp Pro Glu Ser Phe Lys Lys Phe Arg Met Lys Gln Pro Pro Ile
 305                 310                 315 gct tac tgg tta gaa act aaa aag gga agg aaa ggc tgg tta cag aaa      1009
Ala Tyr Trp Leu Glu Thr Lys Lys Gly Arg Lys Gly Trp Leu Gln Lys
320                 325                 330                 335 tat atg cct gct tta cct cat gga agc aaa tac agg gtg tat ttt aac      1057
Tyr Met Pro Ala Leu Pro His Gly Ser Lys Tyr Arg Val Tyr Phe Asn
                 340                 345                 350 aca cca aat ggg cct ctt gaa cga gtt cct gcg tgg gcc aat ttt gtc      1105
Thr Pro Asn Gly Pro Leu Glu Arg Val Pro Ala Trp Ala Asn Phe Val
```

|  |  |  |  |  |  |  |  |  |  |  |  |  |  |  |  |
|---|---|---|---|---|---|---|---|---|---|---|---|---|---|---|---|
|  |  |  |  | 355 |  |  |  | 360 |  |  |  | 365 |  |  |  |
| att | cca | gat | gca | ggc | ggg | atg | gca | tta | gca | gtc | cat | tgg | gaa | cca | cct | 1153 |
| Ile | Pro | Asp | Ala | Gly | Gly | Met | Ala | Leu | Ala | Val | His | Trp | Glu | Pro | Pro |  |
|  |  | 370 |  |  |  | 375 |  |  |  | 380 |  |  |  |  |  |  |
| cct | gaa | tat | gct | tat | aaa | tgg | aaa | cac | aag | cta | cca | gtc | aag | cct | aag | 1201 |
| Pro | Glu | Tyr | Ala | Tyr | Lys | Trp | Lys | His | Lys | Leu | Pro | Val | Lys | Pro | Lys |  |
| 385 |  |  |  |  | 390 |  |  |  |  | 395 |  |  |  |  |  |  |
| tcc | ttg | cgc | ata | tat | gaa | tgt | cat | gtt | ggc | atc | tct | ggc | cag | gaa | cca | 1249 |
| Ser | Leu | Arg | Ile | Tyr | Glu | Cys | His | Val | Gly | Ile | Ser | Gly | Gln | Glu | Pro |  |
| 400 |  |  |  |  | 405 |  |  |  |  | 410 |  |  |  |  | 415 |  |
| aaa | gtt | tca | tct | ttc | aat | gat | ttt | att | agc | aag | gtc | ctt | ccg | cat | gta | 1297 |
| Lys | Val | Ser | Ser | Phe | Asn | Asp | Phe | Ile | Ser | Lys | Val | Leu | Pro | His | Val |  |
|  |  |  |  | 420 |  |  |  |  | 425 |  |  |  |  | 430 |  |  |
| aaa | gaa | gct | gga | tac | aat | gca | ata | caa | att | att | gga | gtt | gtt | gag | cac | 1345 |
| Lys | Glu | Ala | Gly | Tyr | Asn | Ala | Ile | Gln | Ile | Ile | Gly | Val | Val | Glu | His |  |
|  |  |  | 435 |  |  |  |  | 440 |  |  |  |  | 445 |  |  |  |
| aag | gat | tat | ttc | act | gtt | gga | tat | aga | gtg | acc | aat | ttt | tat | gct | gtt | 1393 |
| Lys | Asp | Tyr | Phe | Thr | Val | Gly | Tyr | Arg | Val | Thr | Asn | Phe | Tyr | Ala | Val |  |
|  |  |  | 450 |  |  |  |  | 455 |  |  |  |  | 460 |  |  |  |
| agt | agc | cgt | tat | ggc | aca | ccg | gat | gac | ttc | aag | cgc | ttg | gtt | gat | gaa | 1441 |
| Ser | Ser | Arg | Tyr | Gly | Thr | Pro | Asp | Asp | Phe | Lys | Arg | Leu | Val | Asp | Glu |  |
| 465 |  |  |  |  | 470 |  |  |  |  | 475 |  |  |  |  |  |  |
| gca | cat | ggg | ctt | gga | ctg | ctt | gtc | ttt | ttg | gag | att | gtg | cac | tct | tat | 1489 |
| Ala | His | Gly | Leu | Gly | Leu | Leu | Val | Phe | Leu | Glu | Ile | Val | His | Ser | Tyr |  |
| 480 |  |  |  |  | 485 |  |  |  |  | 490 |  |  |  |  | 495 |  |
| gca | gca | gca | gat | gaa | atg | gtt | ggg | tta | tct | ctt | ttt | gat | gga | gca | aat | 1537 |
| Ala | Ala | Ala | Asp | Glu | Met | Val | Gly | Leu | Ser | Leu | Phe | Asp | Gly | Ala | Asn |  |
|  |  |  |  | 500 |  |  |  |  | 505 |  |  |  |  | 510 |  |  |
| gat | tgc | tat | ttc | cac | act | ggt | aaa | cgt | gga | cac | cac | aaa | ttc | tgg | ggc | 1585 |
| Asp | Cys | Tyr | Phe | His | Thr | Gly | Lys | Arg | Gly | His | His | Lys | Phe | Trp | Gly |  |
|  |  |  | 515 |  |  |  |  | 520 |  |  |  |  | 525 |  |  |  |
| aca | cgg | atg | ttc | aaa | tat | gga | gat | ctt | gat | gtt | ctg | cac | ttt | ctt | ctt | 1633 |
| Thr | Arg | Met | Phe | Lys | Tyr | Gly | Asp | Leu | Asp | Val | Leu | His | Phe | Leu | Leu |  |
|  |  | 530 |  |  |  |  | 535 |  |  |  |  | 540 |  |  |  |  |
| tca | aat | ctg | aac | tgg | tgg | gtg | gag | gag | tat | cat | gtc | gat | ggc | ttc | cat | 1681 |
| Ser | Asn | Leu | Asn | Trp | Trp | Val | Glu | Glu | Tyr | His | Val | Asp | Gly | Phe | His |  |
| 545 |  |  |  |  | 550 |  |  |  |  | 555 |  |  |  |  |  |  |
| ttt | cat | tcg | ctc | tcg | tcc | atg | ttg | tat | acg | cat | aat | gga | ttt | gct | tca | 1729 |
| Phe | His | Ser | Leu | Ser | Ser | Met | Leu | Tyr | Thr | His | Asn | Gly | Phe | Ala | Ser |  |
| 560 |  |  |  |  | 565 |  |  |  |  | 570 |  |  |  |  | 575 |  |
| ttt | act | ggt | gac | atg | gat | gaa | tac | tgt | aac | caa | tat | gtt | gac | aag | gag | 1777 |
| Phe | Thr | Gly | Asp | Met | Asp | Glu | Tyr | Cys | Asn | Gln | Tyr | Val | Asp | Lys | Glu |  |
|  |  |  |  | 580 |  |  |  |  | 585 |  |  |  |  | 590 |  |  |
| gcc | tta | ttg | tac | ctc | ata | tta | gca | aat | gaa | gta | tta | cat | gct | ctt | cat | 1825 |
| Ala | Leu | Leu | Tyr | Leu | Ile | Leu | Ala | Asn | Glu | Val | Leu | His | Ala | Leu | His |  |
|  |  |  |  | 595 |  |  |  |  | 600 |  |  |  |  | 605 |  |  |
| cct | aat | gtg | atc | acg | att | gct | gag | gat | gca | act | ctg | tat | cct | gga | ctc | 1873 |
| Pro | Asn | Val | Ile | Thr | Ile | Ala | Glu | Asp | Ala | Thr | Leu | Tyr | Pro | Gly | Leu |  |
|  |  | 610 |  |  |  |  | 615 |  |  |  |  | 620 |  |  |  |  |
| tgc | gat | cca | aca | tct | caa | ggt | gga | ctg | ggc | ttt | gat | tat | ttt | gcc | aat | 1921 |
| Cys | Asp | Pro | Thr | Ser | Gln | Gly | Gly | Leu | Gly | Phe | Asp | Tyr | Phe | Ala | Asn |  |
| 625 |  |  |  |  | 630 |  |  |  |  | 635 |  |  |  |  |  |  |
| ctt | tct | gcc | tca | gag | atg | tgg | ctt | gca | tta | ctt | gaa | aat | act | cct | gat | 1969 |
| Leu | Ser | Ala | Ser | Glu | Met | Trp | Leu | Ala | Leu | Leu | Glu | Asn | Thr | Pro | Asp |  |
| 640 |  |  |  |  | 645 |  |  |  |  | 650 |  |  |  |  | 655 |  |
| cat | gaa | tgg | tgc | atg | agt | aag | att | gtt | agc | aca | tta | gtg | ggc | gat | aga | 2017 |
| His | Glu | Trp | Cys | Met | Ser | Lys | Ile | Val | Ser | Thr | Leu | Val | Gly | Asp | Arg |  |
|  |  |  |  | 660 |  |  |  |  | 665 |  |  |  |  | 670 |  |  |
| caa | aat | act | gat | aaa | atg | ctt | ttg | tat | gca | gaa | aat | cac | aac | cag | tcc | 2065 |
| Gln | Asn | Thr | Asp | Lys | Met | Leu | Leu | Tyr | Ala | Glu | Asn | His | Asn | Gln | Ser |  |

```
                    675                 680                 685
att tct gga ggt cgt tcc ttc gca gaa ata ctg att ggt aac tcc ttg      2113
Ile Ser Gly Gly Arg Ser Phe Ala Glu Ile Leu Ile Gly Asn Ser Leu
            690                 695                 700 ggg aaa tcc tcc ata tca caa gag tca tta ctt aga ggc tgc tcg tta      2161
Gly Lys Ser Ser Ile Ser Gln Glu Ser Leu Leu Arg Gly Cys Ser Leu
        705                 710                 715 cac aag atg atc aga tta att aca tct aca att ggt ggt cat gca tac      2209
His Lys Met Ile Arg Leu Ile Thr Ser Thr Ile Gly Gly His Ala Tyr
720                 725                 730                 735 ctc aac ttc atg ggc aat gaa ttt ggt cac cca aag aga gta gag ttt      2257
Leu Asn Phe Met Gly Asn Glu Phe Gly His Pro Lys Arg Val Glu Phe
                740                 745                 750 cca atg tca agc aac aat ttc tcc ttt tca ctg gct aac cgt cgc tgg      2305
Pro Met Ser Ser Asn Asn Phe Ser Phe Ser Leu Ala Asn Arg Arg Trp
            755                 760                 765 gat cta ttg gaa gat gtt gta cat tat caa ttg ttc tca ttt gat aag      2353
Asp Leu Leu Glu Asp Val Val His Tyr Gln Leu Phe Ser Phe Asp Lys
        770                 775                 780 ggt atg atg gac ttg gat aaa aat ggg aga att ttg tcc aga ggt ctt      2401
Gly Met Met Asp Leu Asp Lys Asn Gly Arg Ile Leu Ser Arg Gly Leu
785                 790                 795 gcc aac att cac cat gtc aat gat act acc atg gtg att tct tac ttg      2449
Ala Asn Ile His His Val Asn Asp Thr Thr Met Val Ile Ser Tyr Leu
800                 805                 810                 815 aga ggt ccc aat ctc ttt gtg ttc aac ttt cat cct gtc aat tca tat      2497
Arg Gly Pro Asn Leu Phe Val Phe Asn Phe His Pro Val Asn Ser Tyr
                820                 825                 830 gaa aga tac att ata ggt gtg gaa gaa gct gga gag tat caa gtc aca      2545
Glu Arg Tyr Ile Ile Gly Val Glu Glu Ala Gly Glu Tyr Gln Val Thr
            835                 840                 845 tta aat aca gat gaa aac aag tat ggt ggt aga gga cta ctt ggc cat      2593
Leu Asn Thr Asp Glu Asn Lys Tyr Gly Gly Arg Gly Leu Leu Gly His
        850                 855                 860 gat cag aat att caa aga acc att agt aga aga gct gat gga atg aga      2641
Asp Gln Asn Ile Gln Arg Thr Ile Ser Arg Arg Ala Asp Gly Met Arg
865                 870                 875 ttt tgc ttg gaa gtg cct ctg cca agt aga agt gct cag gtc tac aag      2689
Phe Cys Leu Glu Val Pro Leu Pro Ser Arg Ser Ala Gln Val Tyr Lys
880                 885                 890                 895 ttg acc cga att cta aga gca tgatcactct agtaatcaaa gtgcctcata         2740
Leu Thr Arg Ile Leu Arg Ala
                900 tgatgacaca aaaggaaagg ttctacattg cccttacact gatcaatatt gacacctttc    2800 cgaggtgagt ttctgtgatt cttgagcaga ctgttggcta gtcaattatc atgaactttt    2860 gccttcagca tccggatagt cgcttctcct gtgcaatgag ggcatggacg aattttttttt   2920 tggcttgtca tggggtcat aagcatccgc cagattaaga tttcacaggc ctcgagtaaa     2980 accatcactt actttaagga tacacaaaca caccaacggg gtgcaggctc tgataccttc    3040 taaagtg                                                              3047

<210> SEQ ID NO 14
<211> LENGTH: 902
<212> TYPE: PRT
<213> ORGANISM: Solanum tuberosum

<400> SEQUENCE: 14

Met Leu Ser Leu Ser Asp Ser Ile Arg Ile Ser Ser Pro Leu Ser Asp
1               5                   10                  15
```

-continued

```
Ser Arg Leu Ser Phe Leu Ser Gln Thr Gly Ser Arg Thr Ser Arg Gln
            20                  25                  30
Leu Lys Phe Val Arg Ser Arg Ala Arg Val Ser Arg Cys Arg Cys
        35                  40                  45
Ser Ala Thr Glu Gln Pro Pro Gln Arg Arg Lys Gln Arg Pro Glu
50                  55                  60
Lys Tyr Lys Gln Ser Glu Glu Gly Lys Gly Ile Asp Pro Val Gly Phe
65                  70                  75                  80
Leu Ser Lys Tyr Gly Ile Thr His Lys Ala Phe Ala Gln Phe Leu Arg
                85                  90                  95
Glu Arg Tyr Lys Ser Leu Lys Asp Leu Lys Asp Glu Ile Leu Thr Arg
                100                 105                 110
His Phe Ser Leu Lys Glu Met Ser Thr Gly Tyr Glu Leu Met Gly Met
            115                 120                 125
His Arg Asn Ile Gln His Arg Val Asp Phe Leu Glu Trp Ala Pro Gly
        130                 135                 140
Ala Arg Tyr Cys Ala Leu Ile Gly Asp Phe Asn Gly Trp Ser Thr Thr
145                 150                 155                 160
Gly Asn Cys Ala Arg Glu Gly His Phe Gly His Asp Asp Tyr Gly Tyr
                165                 170                 175
Trp Phe Ile Ile Leu Glu Asp Lys Leu Arg Glu Gly Glu Pro Asp
                180                 185                 190
Lys Leu Tyr Phe Gln Gln Tyr Asn Tyr Ala Glu Asp Tyr Gly Lys Gly
            195                 200                 205
Asp Thr Gly Ile Thr Val Glu Glu Ile Phe Lys Lys Ala Asn Asp Glu
        210                 215                 220
Tyr Trp Glu Pro Gly Glu Asp Arg Phe Ile Lys Ser Arg Tyr Glu Val
225                 230                 235                 240
Ala Ala Lys Leu Tyr Glu Glu Met Phe Gly Pro Asn Gly Pro Gln Thr
                245                 250                 255
Glu Glu Glu Leu Glu Ala Met Pro Asp Ala Ala Thr Arg Tyr Lys Thr
                260                 265                 270
Trp Lys Glu Gln Gln Lys Glu Asp Pro Ala Ser Asn Leu Pro Ser Tyr
            275                 280                 285
Asp Val Val Asp Ser Gly Lys Glu Tyr Asp Ile Tyr Asn Ile Ile Gly
        290                 295                 300
Asp Pro Glu Ser Phe Lys Lys Phe Arg Met Lys Gln Pro Pro Ile Ala
305                 310                 315                 320
Tyr Trp Leu Glu Thr Lys Lys Gly Arg Lys Gly Trp Leu Gln Lys Tyr
                325                 330                 335
Met Pro Ala Leu Pro His Gly Ser Lys Tyr Arg Val Tyr Phe Asn Thr
                340                 345                 350
Pro Asn Gly Pro Leu Glu Arg Val Pro Ala Trp Ala Asn Phe Val Ile
            355                 360                 365
Pro Asp Ala Gly Gly Met Ala Leu Ala Val His Trp Glu Pro Pro Pro
        370                 375                 380
Glu Tyr Ala Tyr Lys Trp Lys His Lys Leu Pro Val Lys Pro Lys Ser
385                 390                 395                 400
Leu Arg Ile Tyr Glu Cys His Val Gly Ile Ser Gly Gln Glu Pro Lys
                405                 410                 415
Val Ser Ser Phe Asn Asp Phe Ile Ser Lys Val Leu Pro His Val Lys
                420                 425                 430
Glu Ala Gly Tyr Asn Ala Ile Gln Ile Ile Gly Val Val Glu His Lys
```

```
                435                 440                 445
Asp Tyr Phe Thr Val Gly Tyr Arg Val Thr Asn Phe Tyr Ala Val Ser
450                 455                 460

Ser Arg Tyr Gly Thr Pro Asp Phe Lys Arg Leu Val Asp Glu Ala
465                 470                 475             480

His Gly Leu Gly Leu Leu Val Phe Leu Glu Ile Val His Ser Tyr Ala
                485                 490                 495

Ala Ala Asp Glu Met Val Gly Leu Ser Leu Phe Asp Gly Ala Asn Asp
            500                 505                 510

Cys Tyr Phe His Thr Gly Lys Arg Gly His His Lys Phe Trp Gly Thr
                515                 520                 525

Arg Met Phe Lys Tyr Gly Asp Leu Asp Val Leu His Phe Leu Leu Ser
530                 535                 540

Asn Leu Asn Trp Trp Val Glu Glu Tyr His Val Asp Gly Phe His Phe
545                 550                 555                 560

His Ser Leu Ser Ser Met Leu Tyr Thr His Asn Gly Phe Ala Ser Phe
                565                 570                 575

Thr Gly Asp Met Asp Glu Tyr Cys Asn Gln Tyr Val Asp Lys Glu Ala
                580                 585                 590

Leu Leu Tyr Leu Ile Leu Ala Asn Glu Val Leu His Ala Leu His Pro
            595                 600                 605

Asn Val Ile Thr Ile Ala Glu Asp Ala Thr Leu Tyr Pro Gly Leu Cys
610                 615                 620

Asp Pro Thr Ser Gln Gly Gly Leu Gly Phe Asp Tyr Phe Ala Asn Leu
625                 630                 635                 640

Ser Ala Ser Glu Met Trp Leu Ala Leu Leu Glu Asn Thr Pro Asp His
                645                 650                 655

Glu Trp Cys Met Ser Lys Ile Val Ser Thr Leu Val Gly Asp Arg Gln
                660                 665                 670

Asn Thr Asp Lys Met Leu Leu Tyr Ala Glu Asn His Asn Gln Ser Ile
            675                 680                 685

Ser Gly Gly Arg Ser Phe Ala Glu Ile Leu Ile Gly Asn Ser Leu Gly
690                 695                 700

Lys Ser Ser Ile Ser Gln Glu Ser Leu Leu Arg Gly Cys Ser Leu His
705                 710                 715                 720

Lys Met Ile Arg Leu Ile Thr Ser Thr Ile Gly Gly His Ala Tyr Leu
                725                 730                 735

Asn Phe Met Gly Asn Glu Phe His Pro Lys Arg Val Glu Phe Pro
            740                 745                 750

Met Ser Ser Asn Asn Phe Ser Phe Ser Leu Ala Asn Arg Arg Trp Asp
            755                 760                 765

Leu Leu Glu Asp Val Val His Tyr Gln Leu Phe Ser Phe Asp Lys Gly
770                 775                 780

Met Met Asp Leu Asp Lys Asn Gly Arg Ile Leu Ser Arg Gly Leu Ala
785                 790                 795             800

Asn Ile His His Val Asn Asp Thr Thr Met Val Ile Ser Tyr Leu Arg
                805                 810                 815

Gly Pro Asn Leu Phe Val Phe Asn Phe His Pro Val Asn Ser Tyr Glu
            820                 825                 830

Arg Tyr Ile Ile Gly Val Glu Glu Ala Gly Glu Tyr Gln Val Thr Leu
                835                 840                 845

Asn Thr Asp Glu Asn Lys Tyr Gly Gly Arg Gly Leu Leu Gly His Asp
850                 855                 860
```

```
Gln Asn Ile Gln Arg Thr Ile Ser Arg Arg Ala Asp Gly Met Arg Phe
865                 870                 875                 880

Cys Leu Glu Val Pro Leu Pro Ser Arg Ser Ala Gln Val Tyr Lys Leu
                885                 890                 895

Thr Arg Ile Leu Arg Ala
            900

<210> SEQ ID NO 15
<211> LENGTH: 30
<212> TYPE: DNA
<213> ORGANISM: Artificial sequence
<220> FEATURE:
<223> OTHER INFORMATION: Oligonucleotide

<400> SEQUENCE: 15
tcaagtcgac cacaaccagt ccatttctgg                                    30

<210> SEQ ID NO 16
<211> LENGTH: 30
<212> TYPE: DNA
<213> ORGANISM: Artificial sequence
<220> FEATURE:
<223> OTHER INFORMATION: Oligonucleotide

<400> SEQUENCE: 16
tcaaactagt cacaaccagt ccatttctgg                                    30

<210> SEQ ID NO 17
<211> LENGTH: 21
<212> TYPE: DNA
<213> ORGANISM: Artificial sequence
<220> FEATURE:
<223> OTHER INFORMATION: Oligonucleotide

<400> SEQUENCE: 17
cactttagaa ggtatcagag c                                             21

<210> SEQ ID NO 18
<211> LENGTH: 22
<212> TYPE: DNA
<213> ORGANISM: Artificial sequence
<220> FEATURE:
<223> OTHER INFORMATION: Oligonucleotide

<400> SEQUENCE: 18
gtatttctgc gaaggaacga cc                                            22

<210> SEQ ID NO 19
<211> LENGTH: 20
<212> TYPE: DNA
<213> ORGANISM: Artificial sequence
<220> FEATURE:
<223> OTHER INFORMATION: Oligonucleotide

<400> SEQUENCE: 19
aacaatgctc tctctgtcgg                                               20

<210> SEQ ID NO 20
<211> LENGTH: 30
<212> TYPE: DNA
<213> ORGANISM: Artificial sequence
<220> FEATURE:
<223> OTHER INFORMATION: Oligonucleotide

<400> SEQUENCE: 20
gcttgtcgac gggagaattt tgtccagagg                                    30
```

```
<210> SEQ ID NO 21
<211> LENGTH: 31
<212> TYPE: DNA
<213> ORGANISM: Artificial sequence
<220> FEATURE:
<223> OTHER INFORMATION: Oligonucleotide

<400> SEQUENCE: 21
gatcgtcgac agcacttcta cttggcagag g                              31
```

PHOSPHORYLATED WAXY POTATO STARCH

CROSS-REFERENCE TO RELATED APPLICATIONS

This application is the U.S. National Stage filing of International Application No. PCT/EP2006/003027, filed Mar. 30, 2006, which claims benefit of European Patent Application No. 05090085.1, filed Apr. 1, 2005, and U.S. Provisional Patent Application No. 60/669,665, filed Apr. 8, 2005, the disclosures of each of which are hereby incorporated by reference.

BACKGROUND OF THE INVENTION (i) Field of the Invention

The present invention relates to potato starches having an amylose content of less than 10% by weight, a phosphate content in the C6 position of between 35 and 100 nmol of phosphate per milligram of starch and an increased content of side chains having a DP of from 12 to 19 as compared with the potato starch from corresponding wild-type potato plants.

(ii) Description of the Related Art

In view of the increasing importance which is currently being attached to plant components as renewable sources of raw material, one of the tasks of biotechnological research is to endeavor to adapt these plant raw materials to the requirements of the processing industry. In addition to this, it is necessary to achieve a great diversity of substances in order to enable renewable raw materials to be used in as many areas of employment as possible.

While the polysaccharide starch is composed of chemically uniform basic units, i.e. the glucose molecules, it is a complex mixture of different molecular forms which exhibit differences with regard to the degree of polymerization and branching and consequently differ greatly from each other in their physicochemical properties. A distinction is made between amylose starch, an essentially unbranched polymer composed of alpha-1,4-glycosidically linked glucose units, and amylopectin starch, a branched polymer in which the branches are formed as a result of the appearance of additional alpha-1,6-glycosidic linkages. Another important difference between amylose and amylopectin lies in their molecular weights. While amylose, depending on the origin of the starch, has a molecular weight of $5 \times 10^5$-$10^6$ Da, the molecular weight of amylopectin is between $10^7$ and $10^8$ Da. The two macromolecules can be differentiated by their molecular weight and their different physicochemical properties, something which can most readily be visualized by their different iodine-binding properties.

Amylose was regarded for a long time as being a linear polymer which consisted of alpha-1,4-glycosidically linked alpha-D-glucose monomers. However, more recent studies have demonstrated the presence of a small proportion of alpha-1,6-glycosidic branching points (approx. 0.1%) (Hizukuri and Takagi, Carbohydr. Res. 134 (1984), 1-10; Takeda et al., Carbohydr. Res. 132, (1984), 83-92).

Amylopectin constitutes a complex mixture composed of glucose chains which are branched differently. Amylopectin is more strongly branched than amylose. Side chains are linked by way of $\alpha$-1,6-glycosidic bonds to the main chain, which is composed of $\alpha$-1,4-glycosidically linked $\alpha$-D-glucose monomers. According to textbook data (Voet and Voet, Biochemistry, John Wiley & Sons, 1990), the $\alpha$-1,6 branches occur every 24 to 30 glucose residues on average. This corresponds to a degree of branching of approx. 3%-4%. The data with regard to the degree of branching are variable and depend on the origin (e.g. plant species, plant variety, etc.) of the given starch. In typical plants which are used for industrial starch production, e.g. corn, wheat or potato, approx. 20%-30% of the synthesized starch is composed of amylose starch and approx. 70%-80% is composed of amylopectin starch.

The functional properties, such as the solubility, the retrogradation behavior, the ability to bind water, the film-forming properties, the viscosity, the pasting properties, the freeze/thaw stability, the acid stability, the gel strength and the starch grain size of starches are influenced, inter alia, by the amylose/amylopectin ratio, the molecular weight, the pattern of side chain distribution of the amylopectin, the content of ions, the content of lipid and protein, the mean starch grain size, the starch grain morphology, etc. The functional properties of starch are also influenced by the content of phosphate, in the starch. In this connection, a distinction is made between phosphate which is covalently bonded in the form of monoesters to the glucose molecules of the starch (termed starch phosphate below) and phosphate in the form of phospholipids which are associated with the starch.

The content of starch phosphate varies in dependence on the plant type. Thus, for example, certain corn mutants synthesize a starch having an elevated content of starch phosphate (waxy corn 0.002% and high-amylose corn 0.013%) whereas conventional corn types only exhibit traces of starch phosphate. Small quantities of starch phosphate are also found in wheat (0.001%) whereas it has not been possible to detect any starch phosphate in oats and sorghum. Relatively large quantities of starch phosphate have thus far been detected in tuber or root storage starch, for example tapioca (0.008%), sweet potato (0.011%), arrowroot (0.021%) or potato (0.089%).

The percentage values of the starch phosphate content which have been cited above in each case relate to the dry weight of the starch and were determined by Jane et al. (1996, Cereal Foods World 41 (11), 827-832). Starch phosphate can be present in the form of monoesters at the C2, C3 or C6 position in the polymerized glucose monomers (Takeda and Hizukuri, 1971, Starch/Stärke 23, 267-272). In general, from about 30% to 40% of the covalently bound starch phosphate groups are located in the C3 position, and from about 60% to 70% are located in the C6 position, in the glucose monomers (Blennow et al., 2000, Int. J. of Biological Macromolecules 27, 211-218).

Potato amylopectin starches, i.e. starches having an amylopectin content of more than 90% and an amylose content of less than 10%, can be obtained from potato plants in which the activity of the starch granule-bound starch synthase GBSSI ("Granule-Bound Starch Synthase I") is reduced (Shure et al., 1983, Cell 35, 225-233; Hovenkamp-Hermelink et al., 1987, Theoretical and Applied Genetics 75, 217-221; Visser et al., 1991, Mol. Gen. Genet. 225, 289-296). GBSSI is involved in the formation of amylose. Inhibition of the GBSSI activity leads to the synthesis of starch which is almost exclusively composed of amylopectin. The corresponding GBSSI gene in maize is known under the name "waxy". Amylopectin starches are also termed waxy starches.

Plants in which the activity of soluble starch synthase III (SSIII) is reduced have also been described (Abel et al., 1996, The Plant Journal 10(6), 981-991; Lloyd et al., 1999, Biochemical Journal 338, 515-521). As compared with starch which is isolated from corresponding wild-type plants, starch from these plants exhibits a relative shift of the amylopectin side chains from relatively long chains to short chains (Lloyd et al., 1999, Biochemical Journal 338, 515-521), an increased content of phosphate, no change in the amylose content (Abel et al., 1996, The Plant Journal 10(6), 9891-9991) and a reduced final viscosity in the RVA analysis (Abel, 1995, Berlin Free University dissertation).

Plants in which the activity of branching enzyme I (BEI) is reduced have also been described (Kossmann et al., 1991, Mol. Gen. Genet. 230, 39-44; Safford et al., 1998, Carbohydrate Polymers 35, 155-168; WO 92/14827). Safford et al. (1998, see above) report that corresponding potatoes produce a starch which has a slightly altered amylose/amylopectin ratio. Nor does the degree of branching of the amylopectin differ significantly from that of a starch which is isolated from wild-type potatoes. However, the starch-bound phosphate content is slightly increased.

WO 01/19975 describes plants in which the GBSSI and the SSII and/or SSIII activities are reduced. As compared with starch from wild-type potatoes, starch from potatoes having reduced activities of GBSSI, SSII and SSIII exhibit a lower amylose content, altered swellability and pasting properties and higher freeze/thaw stability.

WO 01/12782 describes plants in which both the GBSSI activity and the BEI activity are reduced. Starch from these potato plants exhibits a reduced amylose content as compared with potato starch from wild-type plants and an elevated phosphate content and/or a reduced pasting temperature in the RVA analysis as compared with potato starch from plants having the waxy phenotype.

WO 00/08184 describes, inter alia, plants in which both the SSIII activity and the BEI activity are reduced. Starch from these plants exhibits a markedly elevated phosphate content as compared with starch from wild-type plants.

SUMMARY OF THE INVENTION

The present invention is based on the object of making available potato amylopectin starches having novel properties, novel plant cells and/or plants which produce the starches, as well as means and methods for generating said plant cells and/or plants.

This object is achieved by the provision of the embodiments which are described in the patent claims.

The present invention relates to potato starches which have an amylose content, as measured by the method of Hovenkamp-Hermelink et al. (1988, Potato Research 31, 241-246), of less than 10% by weight and a phosphate content in the C6 position of between 35 and 100 nmol of phosphate per mg of starch (dry weight), and an elevated content of side chains having a DP of from 12 to 19 as compared with potato starch derived from corresponding wild-type potato plants.

The present invention furthermore relates to potato starches which have an amylose content, as measured by the method ("General methods") of Hovenkamp-Hermelink et al. (1988, Potato Research 31, 241-246), of less than 10% by weight, a phosphate content in the C6 position of between 35 and 100 nmol of phosphate per mg of starch (dry weight) and a total phosphate content to phosphate content in the C6 position ratio of 1.10-1.60.

The present invention furthermore relates to potato starches which have an amylose content, as measured by the method ("General methods") of Hovenkamp-Hermelink et al. (1988, Potato Research 31, 241-246), of less than 10% by weight, a phosphate content in the C6 position of between 35 and 100 nmol of phosphate per mg of starch (dry weight) and a shear stability of 58% to 80%, in particular of 60% to 78%, preferably of 66% to 77%, particularly preferably of 67% to 75%.

The present invention furthermore relates to potato starches which have an amylose content, as measured by the method ("General methods") of Hovenkamp-Hermelink et al. (1988, Potato Research 31, 241-246), of less than 10% by weight and a peak viscosity determined by the Rotovisko method of 332 SKT to 500 SKT, in particular of 345 SKT-450 SKT, preferably of 360 SKT to 420 SKT and particularly preferably of 370 SKT to 400 SKT.

The present invention furthermore relates to potato starches which have an amylose content, as measured by the method ("General methods") of Hovenkamp-Hermelink et al. (1988, Potato Research 31, 241-246), of less than 10% by weight, a phosphate content in the C6 position of between 35 and 100 nmol of phosphate per mg of starch (dry weight) and a peak viscosity determined by the Rotovisko method of 332 SKT to 500 SKT, in particular of 345 SKT-450 SKT, preferably of 360 SKT to 420 SKT and particularly preferably of 370 SKT to 400 SKT.

DETAILED DESCRIPTION OF THE INVENTION

In connection with the present invention, the amylose content is determined using the method of Hovenkamp-Hermelink et al. (1988, Potato Research 31, 241-246), which is described below for potato starch. This method can also be applied to starches which are isolated from other plant species. Methods for isolating starches are known to the skilled person and are described in detail below in the "General methods" section.

In connection with the present invention, the term "phosphate content in the C6 position" is to be understood as meaning the content of phosphate groups which are covalently bonded to carbon atom position 6 in the glucose monomers in the starch. In principle, the C2, C3 and C6 positions in the glucose units can be phosphorylated in the starch in vivo. In connection with the present invention, the phosphate content in the C6 position (=C6-P content) is determined by way of a glucose-6-phosphate determination using the opticoenzymic test which is described below ("General methods: determining the phosphate content in the C6 position").

In connection with the present invention, the term "total phosphate content" is to be understood as meaning the quantity of starch phosphate which is in total covalently bonded to glucose molecules in the starch. In connection with the present invention, the total phosphate content is determined using the method which is described below ("General methods: determining the total phosphate content").

In connection with the present invention, the term "elevated content of side chains having a DP of from 12 to 19" means an increase in the proportion of side chains in the starch having a DP (=degree of polymerization) of from 12 to 19 to 125%-200%, preferably to 130%-180%, and particularly preferably to 140%-160%, as compared with the proportion of side chains having a DP of from 12 to 19 in potato starch which is isolated from corresponding wild-type potato plants (100%).

In connection with the present invention, the side chain distribution in the starch is determined as described below in the section entitled "General methods: using gel permeation chromatography to analyze the side chain distribution in total starch".

In connection with the present invention, the term "wild-type potato plant cell" means that the cells are potato plant cells which were used as the starting material for producing the plant cells according to the invention, i.e. their genetic information corresponds, apart from the genetic modification which has been introduced, to that of a plant cell according to the invention.

In connection with the present invention, the term "wild-type potato plant" means that the plants are plants which were used as the starting material for producing the plants according to the invention which are described below, i.e. their genetic information corresponds, apart from the genetic modification which has been introduced, to that of a plant according to the invention.

In connection with the present invention, the term "corresponding" means that, when comparing several objects, the objects in question, which are being compared with each other, were maintained under identical conditions. In connection with the present invention, the term "corresponding" means, with regard to wild-type plant cells or wild-type plants, in particular, that the plant cells or plants which are being compared with each other were grown under identical culture conditions and that they are of the same (culture) age.

In a preferred embodiment of the invention, the potato starches according to the invention have an amylose content, as measured using the method of Hovenkamp-Hermelink et al. (1988, Potato Research 31, 241-246), of less than 5% by weight, particularly preferably of less than 3% by weight.

In another preferred embodiment of the invention, the potato starch according to the invention has an elevated phosphate content in the C6 position of 40-85 nmol of C6-P per mg of starch, particularly preferably of 45-70 nmol of C6-P per mg of starch, very particularly preferably of 50-65 nmol of C6-P per mg of starch.

In another preferred embodiment of the invention, the potato starch according to the invention exhibits an elevated phosphate content as compared with that in potato starch derived from corresponding wild-type potato plants. In connection with the present invention, the term "elevated phosphate content" means that the phosphate content in the C6 position in the starch according to the invention is elevated, in particular elevated by 415%-520%, preferably by 430%-500%, and particularly preferably by 440%-490%, as compared with that in starch which is derived from corresponding wild-type plant cells or plants.

In another embodiment of the invention, the potato starch according to the invention exhibits an "elevated content of side chains having a DP of <12". In connection with the present invention, this means an increase in the proportion of the sum of side chains in the starch having a DP (degree of polymerization) of less than 12 to 130%-170%, preferably to 140%-160%, and particularly preferably to 145%-155%, as compared with the proportion of side chains having a DP of less than 12 (100%) in potato starch which is derived from corresponding wild-type potato plants.

In another embodiment of the invention, the potato starch according to the invention exhibits an "elevated content of side chains having a DP of 20-25". In connection with the present invention, this means an increase in the proportion of the sum of side chains in the starch having a DP (=degree of polymerization) of 20-25 to 132%-160%, preferably to 136%-150%, and particularly preferably to 139%-148%, as compared with the proportion of side chains having a DP of 20-25 (100%) in potato starch which is derived from corresponding wild-type potato plants.

In another embodiment of the invention, the potato starch according to the invention exhibits a "reduced content of side chains having a DP of 63-123". In connection with the present invention, this means a reduction in the proportion of the sum of side chains in the starch having a DP (=degree of polymerization) of 63-123 to 50%-95%, preferably to 65%-90%, and particularly preferably to 73%-85%, as compared with the proportion of side chains having a DP of 63-123 (100%) in potato starch which is derived from corresponding wild-type potato plants.

In another embodiment of the invention, the potato starches according to the invention exhibit a "reduced content of side chains having a DP of >123". In connection with the present invention, this means a reduction in the proportion of the sum of side chains in the starch having a DP (=degree of polymerization) of greater than 123 to 0.1%-3.8%, preferably to 0.3%-3.0%, and particularly preferably to 0.5%-2.5%, as compared with the proportion of side chains having a DP greater than 123 (100%) in potato starch which is derived from corresponding wild-type potato plants.

In another preferred embodiment of the invention, the potato starches according to the invention exhibit a total phosphate content to phosphate content in the C6 position ratio of 1.20-1.50, particularly preferably of 1.30-1.40.

In another embodiment of the invention, the potato starches according to the invention exhibit high freeze/thaw stability.

In connection with the present invention, the term "high freeze/thaw stability" means a freeze/thaw stability of at least 60%, in particular of at least 70%, preferably of at least 80%, and particularly preferably of at least 95%. In connection with the present invention, the freeze/thaw stability is determined using the method which is described below ("General methods").

In another embodiment of the invention, the potato starches according to the invention exhibit a high degree of heat stability.

In connection with the present invention, the term "high degree of heat stability" means a heat stability of at least 30%, in particular of at least 40%, and preferably of at least 50%. In connection with the present invention, the heat stability is determined using the method which is described below ("General methods").

In another embodiment of the invention, the potato starches according to the invention exhibit a high degree of shear stability.

In connection with the present invention, the term "high degree of shear stability" means a shear stability of 58% to 80%, in particular of 60% to 78%, preferably of 66% to 77%, particularly preferably of 67% to 75%. In connection with the present invention, the shear stability is determined using the method which is described below ("General methods: Method k).

In another embodiment of the invention, the potato starches according to the invention exhibit a viscosity behavior (e.g. pasting temperature, final viscosity) which is altered as compared with that of potato starch which is derived from corresponding wild-type potato plants. In connection with the present invention, the viscosity properties are determined using the RVA or the Rotovisko method which is described below ("General methods").

In another embodiment of the invention, the potato starches according to the invention exhibit an increased peak viscosity determined by the Rotovisko method ("General methods: Method I").

In connection with the present invention, the term "increased peak viscosity determined by the Rotovisko method" means an increase of the peak viscosity by 23% to 70%, in particular by 27% to 60%, preferably by 35% to 55%, particularly preferably by 40% to 50% compared with the peak viscosity of potato starch which is derived from corresponding wild-type potato plants (100%).

In another embodiment of the invention, the potato starches according to the invention exhibit a peak viscosity determined by the Rotovisko method of 332 SKT to 500 SKT, in particular of 345 SKT-450 SKT, preferably of 360 SKT to 420 SKT and particularly preferably of 370 SKT to 400 SKT.

In another embodiment of the invention, the potato starches according to the invention exhibit a DSC peak temperature which is altered as compared with that of potato starch which is derived from corresponding wild-type potato plants. In connection with the present invention, the DSC peak temperature is determined using the method which is described below ("General methods").

In another embodiment of the invention, the potato starches according to the invention exhibit a gel strength which is reduced as compared with that of potato starch which is derived from corresponding wild-type potato plants. In connection with the present invention, the gel strength is determined using the method which is described below ("General methods").

In another embodiment of the invention, the potato starches according to the invention exhibit a gel strength of 1.0 g to 10.0 g, in particular of 3.5 g to 7.5 g, preferably of 3.7 g to 6.5 g and particularly preferably of 4.0 g to 6.0 g.

The potato starches according to the invention are preferably native potato starches. In connection with the present invention, the term "native starch" means that methods known to the skilled person are used to extract the starch from plants or starch-storing parts of plants without the extracted starch being chemically modified following the extraction.

Furthermore, the present invention relates to a method for the manufacture of the (potato) starch according to the invention, including the step of extracting the starch from a plant cell according to the invention or from a plant according to the invention, from propagation material according to the invention of such a plant and/or from harvestable plant parts according to the invention of such a plant, preferably from starch-storing parts according to the invention of such a plant. Preferably, such a method also includes the step of harvesting the cultivated plants or plant parts and/or the propagation material of these plants before the extraction of the starch and, further, particularly preferably the step of cultivating plants according to the invention before harvesting.

The skilled person is familiar with methods for isolating starch from plants or from starch-storing parts of plants. Methods for extracting the starch from different starch-storing plants have also been described, e.g. in Starch: Chemistry and Technology (eds.: Whistler, BeMiller and Paschall (1994), 2nd edition, Academic Press Inc. London Ltd., ISBN 0-12-746270-8; see, e.g. Chapter XII, pages 412-468; corn and sorghum starches: preparation; by Watson; Chapter XIII, pages 469-479: tapioca, arrowroot and sago starches: preparation; by Corbishley and Miller; Chapter XIV, pages 479-490: potato starch: preparation and uses; by Mitch; Chapter XV, pages 491 to 506: wheat starch: preparation, modification and uses; by Knight and Oson; and Chapter XVI, pages 507 to 528: rice starch: preparation and uses; by Rohmer and Klem; corn starch: Eckhoff et al., Cereal Chem. 73 (1996), 54-57, as a rule corn starch is extracted on an industrial scale using what is termed "wet milling".

The present invention also relates to potato starches according to the invention which possess one or more of the above-described properties. That is, this invention description discloses any combination of the following starch properties: amylose content or amylose/amylopectin ratio, phosphate content, side chain distribution, freeze/thaw stability and heat stability. Any combinations of two, three, four, five, six, seven, eight, nine and all the properties are to be regarded as being disclosed.

The starches according to the invention exhibit properties which appear to make them particularly suitable for being used in processes in which a pronounced ability to swell, a high degree of freeze/thaw stability and/or a high charge density are advantageous. These requirements apply, for example, to thickeners in the foodstuffs industry, especially when these thickeners are frozen for storage or processing and/or a particularly high thickening efficiency is desirable.

Because of their unusually high charge density, which is to be attributed to the covalently bonded phosphate groups, and their low-viscosity thickening, the starches according to the invention are particularly well suited for being used in the paper industry. The high charge density is advantageous since it makes it possible to produce frequently employed amphoteric starches in what is only a one-step derivatization reaction and to a large extent dispense with additional derivatization reactions for introducing negative charges into the starches.

Standard methods, which are known to the skilled person, can be used to chemically and/or physically modify the potato starches according to the invention, preferably native potato starches, after they have been extracted from the potato tubers.

The skilled person knows that the properties of native potato starch can be altered by, e.g., physical (e.g. thermal or mechanical) and/or chemical derivatization and/or breakdown products of the starch (e.g. dextrins) which are obtained by enzymic, acid-hydrolytic or thermal degradation. The starches which are obtained in this connection, and which are to be designated "derivatized potato starches" in connection with the present invention, are particularly suitable for a variety of applications. The native potato starches according to the invention are better suited than are conventional potato starches (derived from wild-type potato plants) for being used as starting substance for preparing the derivatized potato starches because this starting substance exhibits, for example, a higher proportion of reactive functional groups, as a result of the higher content of covalently bonded starch phosphate, is more strongly hydrophilic and is more accessible to chemical agents.

The present invention therefore also relates to derivatized potato starches which contain the, preferably native, potato starches according to the invention and to methods for preparing such a derivatized starch, in which methods potato starch according to the invention, which is preferably native, is subsequently, i.e. after having been extracted from the potato tuber, chemically and/or physically modified, preferably in vitro.

The derivatized starch according to the invention is, in particular, heat-treated starch. The present invention preferably relates to acid-modified starch which has preferably been treated with acid, preferably with hydrochloric acid (at a concentration of up to 1 M) in an aqueous system at temperatures of up to 50° C.

In another embodiment, the present invention relates to derivatized starches which were obtained by subjecting the, preferably native, potato starch according to the invention to a temperature treatment in a dry system, preferably at temperatures of from preferably 120° C. to 140° C.

In another embodiment, the derivatized starches are starch ethers, in particular starch alkyl ethers, O-allyl ethers, hydroxyalkyl ethers, O-carboxymethyl ethers, nitrogen-containing starch ethers, phosphate-containing starch ethers or sulfur-containing starch ethers.

In another embodiment, the derivatized starches are crosslinked starches.

In another embodiment, the derivatized starches are starch graft polymers.

In another embodiment, the derivatized starches are oxidized starches.

In another embodiment, the derivatized starches are starch esters, in particular starch esters which were introduced into the starch using organic acids. The starch esters are particularly preferably phosphate, nitrate, sulfate, xanthate, acetate or citrate starches.

The derivatized starches according to the invention are suitable for a variety of uses in the pharmaceutical industry and in the foodstuffs and/or nonfoodstuffs spheres. Methods for preparing derivatized starches according to the invention are known to the skilled person and are adequately described in the general literature. A review regarding the preparation of derivatized starches can be found, for example, in Orthoefer (in: Corn, Chemistry and Technology, 1987, eds. Watson and Ramstad, Chapter 16, 479-499).

The present invention likewise relates to derivatized starch which can be obtained using the method according to the invention for preparing a derivatized starch.

The present invention furthermore relates to the use of potato starches according to the invention, which are preferably native, for preparing derivatized potato starch.

The potato starches according to the invention are suitable, in native or derivatized form, for a variety of uses in the foodstuffs or nonfoodstuffs sphere.

In principle, the possibilities for using the starch can be divided into two large areas. One of the areas comprises the hydrolysis products of the starch, principally glucose and glucan building blocks, which are obtained using enzymic or chemical methods. They serve as starting compounds for further chemical modifications and processes such as fermentation. In this connection, the simplicity and economical implementation of a hydrolysis process can be of importance for reducing the cost. At present, the process proceeds essentially enzymatically using amyloglucosidase. It will be possible to conceive of saving costs by making less use of enzymes. A change in the structure of the starch, e.g. an increase in the surface of the granule, easier digestibility as a result of a lower degree of branching, or a steric structure which limits accessibility for the enzymes employed, could bring this about.

The other area, in which, because of its polymeric structure, the starch is used as what is termed native starch, divides into two further areas of use:

1. Foodstuffs Industry

Starch is a classical additive for many foodstuffs in which it essentially takes on the function of binding aqueous additives or brings about an increase in viscosity or else an increase in gel formation. Important characteristic features are the flowing and sorption behaviors, the swelling and pasting temperatures, the viscosity and the thickening efficiency, the solubility of the starch, the transparency and paste structure, the heating, shearing and acid stabilities, the tendency to retrogradation, the film-forming ability, the freeze/thaw stability, the digestibility and the ability to form complexes with, for example, inorganic or organic ions.

2. Non-Foodstuffs Industry

In this large area, the starch can be used as an auxiliary for different production processes or as an additive in industrial products. The paper and paperboard industry is to be mentioned, in particular, in connection with using the starch as an auxiliary. In this connection, the starch is first and foremost for retardation (retention of solids), for binding filler and fines particles, as a stabilizer and for dewatering. In addition to this, the favorable properties of the starch are exploited in relation to stiffness, hardness, rattle, feel, shine, glaze, plybond strength and the surfaces.

2.1 Paper and Paperboard Industry

Four areas of application, namely surface, coating, pulp and spraying are to be distinguished within the paper manufacturing process.

The demands placed on the starch with regard to surface treatment are essentially a high degree of brightness, an appropriate viscosity, high viscosity stability, good film formation and low dust formation. When being used in coating, the solids content, an appropriate viscosity, high binding ability and high pigment affinity are of importance. When being used as a pulp additive, rapid, uniform and loss-free dispersion, high mechanical stability and complete retention in the paper web are of importance. When the starch is being used in the spraying area, an appropriate solids content, a high viscosity and a high binding ability are likewise of importance.

2.2 Adhesives Industry

A large area for using the starches is constituted by the adhesives industry, where the possibilities of employment are divided into four constituent areas: use as pure starch glue, use in connection with starch glues which are prepared using special chemicals, use of starch as a substance added to synthetic resins and polymer dispersions, and use of starches as extenders for synthetic adhesives. 90% of the starch-based adhesives are used in the areas constituting corrugated board production, production of paper sacks and bags, production of materials for bonding paper and aluminum, production of cardboard articles, and production of remoistening glue for envelopes, postage stamps, etc.

2.3 Textile Industry and Textile Care Product Industry

The area of textile production and textile care product production represents a large field for using the starches as auxiliaries and additives. The following four areas of use can be distinguished within the textile industry: the use of starch as a sizing material, i.e. as an auxiliary for smoothing and strengthening burring behavior, for protecting against the tractive forces which act during weaving, and for increasing the abrasion resistance in connection with weaving; starch as an agent for textile finishing, especially after quality-impairing pretreatments such as bleaching, dyeing, etc.; starch as a thickener in connection with producing pigment pastes for preventing dye diffusions; and starch as a substance added to warping agents for sewing cottons.

2.4 Building Material Industry

The fourth area of employment is the use of the starches as additives for building materials. An example is the production of gypsum plasterboards in which the starch which is mixed in the gypsum slurry forms a paste with the water, diffuses to the surface of the gypsum panel, where it binds the paperboard to the panel. Other areas of employment are admixing to rendering fibers and mineral fibers. In the case of ready-mixed concrete, starch products are used for delaying setting.

2.5 Soil Stabilization

Another market for the starch presents itself in the case of the production of soil stabilization agents, which are employed for temporarily protecting the soil particles from water in association with earth moving operations. While, according to present day knowledge, the erosion-reducing and incrustation-reducing effects of combination products composed of starch and polymer emulsions are on a level with those of previously employed products, their price is markedly lower than that of these products.

2.6 Use in Plant Protection Products and Fertilizers

One area of employment lies in using the starch in plant protection products for the purpose of modifying the specific properties of the preparations. Thus, the starch can be used for improving the wetting properties of plant protection products and fertilizers, for the metered release of the active compounds, for converting liquid, volatile and/or malodorous active compounds into microcrystalline, stable and formable substances, for mixing incompatible compounds and for extending the duration of action by reducing decomposition.

2.7 The Pharmaceuticals, Medicines and Cosmetics Industry

The area of the pharmaceuticals, medicines and cosmetics industry constitutes another area of employment. In the pharmaceutical industry, the starch can be used as a binder for tablets or for binder dilution in capsules. The starch can also be used as a tablet disintegrant since it absorbs liquid after swallowing and after a short time swells to such an extent that the active compound is released. For reasons of quality, medicinal glidants and wound powders are based on starch. In the sphere of cosmetics, starches are, for example, employed as carriers of powder additives, such as perfumes and salicylic acid. Toothpastes constitute a relatively area for using the starch.

2.8 Addition of Starch to Coal and Briquettes

One area of employment is that of using the starch as a substance which is added to coal and briquettes. A starch additive can be used to agglomerate or briquette coal in a quantitatively high-grade manner, thereby preventing any premature decomposition of the briquettes. The addition of starch is between 4 and 6% in the case of grilling coal and between 0.1 and 0.5% in the case of calorized coal. Starches are also gaining in importance as binders since their addition to coal and briquettes can markedly reduce the release of harmful substances.

2.9 Ore and Coal Slurry Dressing

The starch can also be used as a flocculant in connection with ore and coal slurry dressing.

2.10 Foundry Auxiliary

Another area of use is as a substance which is added to foundry auxiliaries. In a variety of casting processes, there is a need for cores which are produced from sands to which binder has been added. The binder which is nowadays mainly used is bentonite to which modified starches, usually swelling starches, have been added.

The purpose of adding the starch is to increase the flow resistance and to improve binding strength. In addition to this, the swelling starches can exhibit other requirements in relation to production technology, such as dispersible in cold water, rehydratable, readily miscible in sand and high water-binding capacity.

2.11 Use in the Rubber Industry

In the rubber industry, the starch can be used for improving technical and optical quality. The reasons in this connection are the improvement in the surface shine, the improvement in the feel and the appearance (for this, starch is dusted onto the tacky gummed areas of rubbers prior to cold vulcanization) and the improvement in the printability of the rubber.

2.12 Use as a Drilling Auxiliary

Another possible application for the starches according to the invention is in the area of extracting raw materials using drills. Thus, in connection with extracting crude oil, for example, it is necessary to use auxiliaries and/or lubricants which prevent the drill or the drilling gear from overheating.

2.13 Production of Leather Substitutes

Another opportunity for marketing the modified starches is in connection with the production of leather substitutes.

2.14 Starch in Synthetic Polymers

The following areas of application are apparent in the plastics sector: the integration of secondary starch products into the finishing process (starch is only a filler, there is no direct bond between the synthetic polymer and the starch) or alternatively, the integration of secondary starch products into the production of polymers (the starch and the polymer enter into a stable bond).

When compared with other substances such as talc, it is uncompetitive to use the starch simply as a filler. The situation is different when the specific properties of the starch come into play and the property profiles of the final products are markedly altered as a result. An example of this is the use of starch products in the finishing of thermoplastics such as polyethylene. In this connection, the starch and the synthetic polymer are combined, by being coexpressed in a ratio of 1:1, into a "masterbatch", from which various products are produced using granular polyethylene and conventional process technology. The integration of starch into polyethylene films makes it possible to achieve an increase in substance permeability in the case of hollow bodies, an improvement in water vapor permeability, an improvement in antistatic behavior, an improvement in antiblocking behavior and an improvement in printability when using aqueous pigments.

Another possibility is that of using the starch in polyurethane foams. By means of adapting the starch derivatives and optimization with regard to process technology, it is possible to control the reaction between synthetic polymers and the hydroxyl groups of the starches in a selective manner. This results in polyurethane films which are given the following property profiles as a result of starch being used: a reduction in the thermal expansion coefficient, a reduction in the shrinkage behavior, an improvement in the pressure/tension behavior, an increase in water vapor permeability without any change in water uptake, a reduction in flammability and cracking density, no dripping-off of combustible parts, freedom from halogens and diminished aging. Disadvantages which still exist at present are a reduction in compression strength and a reduction in impact strength.

Product development is by now no longer restricted to films. Solid plastic products, such as pots, plates and bowls, having a starch content of more than 50% can also be produced. Furthermore, starch/polymer mixtures are to be judged as being advantageous since they exhibit a very much higher degree of biodegradability.

Furthermore, because of their extreme ability to bind water, starch graft polymers have become exceptionally important. These polymers are products having a starch backbone and a side lattice of a synthetic monomer which is grafted on in accordance with the principle of the free-radical chain mechanism. The starch graft polymers which are nowadays available are characterized by an improved ability to bind and retain up to 1000 g of water per g of starch in association with high viscosity. The areas in which these superabsorbers can be used have expanded greatly in recent years and lie in the hygiene sphere, involving products such as diapers and paddings, and in the agricultural sector, for example in connection with seed pelleting.

Factors which are crucially relevant for using the novel starches are, on the one hand, the structure, water content, protein content, lipid content, fiber content, ash/phosphate content, amylose/amylopectin ratio, molar mass distribution, degree of branching, granule size and shape, and crystallinity, and also, on the other hand, the properties which lead to the following features: flow and sorption behavior, pasting temperature, viscosity, thickening efficiency, solubility, paste structure and transparency, heat, shearing and acid stability, retrogradation tendency, gel formation, freeze/thaw stability, complex formation, iodine binding, film formation, adhesive strength, enzyme stability, digestibility and reactivity.

The potato starch according to the invention, which is preferably native, can be prepared by isolating it from genetically modified potato plants in which the genetic modification leads to a reduction in the GBSSI, SSIII and BEI activities and to a reduction in the expression of the gene specified under SEQ ID NO 11 or SEQ ID NO 13, as compared with the activities of the corresponding wild-type potato plant cells or wild-type potato plants.

The present invention therefore also relates to plant cells and plants which are genetically modified, with the genetic modification leading to a reduction in the GBSSI, SSIII and BEI activities, and to a reduction in the expression of the gene specified under SEQ ID NO 11 or SEQ ID NO 13, as compared with the activities of corresponding wild-type plant cells or wild-type plants.

In connection with the present invention, the term "GBSSI" is to be understood as meaning any enzyme which belongs to the isoform I class of starch granule-bound starch synthases (EC 2.4.1.21).

In connection with the present invention, the term "GBSSI gene" is to be understood as meaning a nucleic acid molecule or polynucleotide (cDNA or DNA) which encodes GBSSI. Polynucleotides encoding GBSSI have been described in the case of a variety of plant species, such as corn (Genbank Acc. Nos. AF079260, AF079261), wheat (Genbank Acc. Nos. AB019622, AB019623, AB019624), rice (Genbank Acc. Nos. AF092443, AF09244, AF031162), barley (Genbank Acc. Nos. X07931, X07932), and potato (Genbank Acc. No. X58453). In one embodiment of the invention, the GBSSI gene exhibits an identity of at least 70%, in particular of at least 80%, of at least 90%, preferably of at least 95%, with the coding region of the nucleotide sequence which is depicted in SEQ ID NO 6. In a particularly preferred embodiment, the GBSSI gene is, in connection with the present invention, a nucleic acid molecule (cDNA or DNA) which encodes potato plant GBSSI; particular preference is given to the GBSSI gene which is specified under SEQ ID NO 6.

In connection with the present invention, the term "SSIII" is to be understood as meaning a particular class of soluble starch synthases (ADP-glucose 1,4-α-D-glucan 4-α-D-glucosyltransferase; EC 2.4.1.21). Soluble starch synthases catalyze a glycosylation reaction in which glucose residues of the substrate ADP-glucose are transferred to α-1,4-linked glucan chains with the formation of an α-1,4 linkage (ADP-glucose+ {(1,4)-α-D-glucosyl}(N)<=>ADP+{(1,4)-α-D-glucosyl} (N+1)).

SSIIIs are described, for example, in Marshall et al. (1996, The Plant Cell 8, 1121-1135), Li et al. (2000, Plant Physiology 123, 613-624), Abel et al. (1996, The Plant Journal 10(6), 981-991) and in WO 00/66745. The structure of SSIIIs frequently exhibits a sequence of particular domains and possesses a signal peptide, for transport into plastids, at its N terminus. There then follow, in the direction of the C terminus, an N-terminal region, an SSIII-specific region and a catalytic domain (Li et al., 2000, Plant Physiology 123, 613-624). Further analyses based on primary sequence comparisons (http://hits.isb-sib.ch/cgi-bin/PFSCAN) have shown that potato-derived SSIII protein exhibits what is termed a carbohydrate binding domain (CBM). This domain (Pfam motif cbm 25=SEQ ID NO 3) comprises amino acids 377 to 437 of the potato SSIII protein sequence depicted in SEQ ID NO 2. In connection with the present invention, an SSIII protein is to be understood as being a protein which exhibits an identity of at least 70%, preferably of at least 80%, particularly preferably of at least 90%, very particularly preferably of at least 95%, with the sequence depicted in SEQ ID NO 2.

In connection with the present invention, the term "SSIII gene" is to be understood as meaning a nucleic acid molecule (DNA or cDNA) which encodes an SSIII protein. Nucleic acid molecules encoding SSIIIs have been described in the case of a variety of plant species, for example the potato (Abel et al., 1996, The Plant Journal 10(6), 981-991). In connection with the present invention, an "SSIII gene" is to be understood as meaning a nucleic acid molecule which exhibits an identity of least 70%, in particular of at least 80%, preferably of at least 90%, very particularly preferably of at least 95%, with the coding region of the sequence depicted in SEQ ID NO 1. In a particularly preferred embodiment, the SSIII gene is, in connection with the present invention, a nucleic acid molecule (cDNA or DNA) which encodes potato plant SSIII; particular preference is given to the potato SSIII gene which is specified under SEQ ID NO 1.

In connection with the present invention, the term "BEI" is to be understood as meaning an isoform I branching enzyme (BE) (α-1,4-glucan: α-1,4-glucan 6-glycosyltransferase; E.C. 2.4.1.18), which catalyzes a trans-glycosylation reaction in which α-1,4-linkages in an α-1,4-glucan donor are hydrolyzed and the α-1,4-glucan chains which are released in this connection are transferred to an α-1,4-glucan acceptor chain and, in association with this, converted into α-1,6 linkages. BEI is preferably derived from potato plants.

In this connection, the designation of the isoforms follows the nomenclature proposed by Smith-White and Preiss (Smith-White and Preiss, 1994, Plant Mol. Biol. Rep. 12, 67-71; Larsson et al., 1998, Plant Mol. Biol. 37, 505-511). This nomenclature is based on all enzymes which exhibit higher homology (identity) at the amino acid level with corn BEI (GenBank Acc. No. D11081; Baba et al., 1991, Biochem. Biophys. Res. Commun. 191 (1), 87-94; Kim et al., 1998, Gene 216, 233-243) than with corn BEII (Genbank Acc. Nos. AF072725, U65948) being designated isoform I branching enzymes or BEIs for short.

In connection with the present invention, the term "BEI gene" is to be understood as meaning a nucleic acid molecule or polynucleotide (cDNA or DNA) which encodes BEI. Polynucleotides encoding BEIs have been described in the case of a variety of plant species, for example in the case of corn (Genbank Acc. Nos. D11081, AF072724), rice (Genbank Acc. No. D11082) and potato. Various forms of the potato BEI gene or potato BEI have, for example, been described by Khoshnoodi et al. (1996, Eur. J. Biochem. 242 (1), 148-155, Genbank Acc. No. Y08786) and by Kossmann et al. (1991, Mol. Gen. Genet. 230, 39-44).

In one embodiment of the invention, the BEI gene exhibits an identity of at least 70%, in particular of at least 80%, of at least 90%, preferably at least 95%, with the coding region of the nucleotide sequence depicted in SEQ ID NO 4. In a particularly preferred embodiment, the BEI gene is, in connection with the present invention, a nucleic acid molecule (cDNA or DNA) which encodes potato plant BEI; particular preference is given to the BEI gene specified under SEQ ID NO 4. In potato plants, the BEI gene is principally expressed in the tubers and hardly at all in the leaves (Larsson et al., 1998, Plant Mol. Biol. 37, 505-511).

In the context of the definitions of the terms "GBSSI gene", "SSIII gene" and/or "BEI gene", the "Genbank Acc" numbers and literature reference citations refer to specific polynucleotide sequences which encode the corresponding enzymes. Embodiments of the present invention in which polynucleotides having the sequences specified in the citations can be used are described below. In this connection, the invention is naturally not restricted to using such precisely described sequences or parts of these sequences. It is also possible, for example, to use polynucleotides which exhibit an identity of at least 80%, preferably at least 90%, particularly preferably of at least 95%, and very particularly preferably of at least 98%, with the sequences which are specified.

Genes which exhibit the nucleotide sequence specified under SEQ ID NO 11 or SEQ ID NO 13, and their corresponding proteins which exhibit the amino acid sequence specified under SEQ ID NO 12 or SEQ ID NO 14, are involved in starch biosynthesis in plants. The amino acid sequences of these proteins exhibit homology with *Arabidopsis thaliana* proteins (GenBank Acc. No: BAB02827), which are described there as being branching enzyme-like proteins. In connection with the present invention, it has been found, surprisingly, that potato plants which exhibit reduced expression of the gene specified under SEQ ID NO 11 or SEQ ID NO 13, and exhibit a reduction in GBSSI, SSIII and BEI activities, produce the, preferably native, potato starches according to the invention. It can be concluded from this that the gene specified under SEQ ID NO 11 or SEQ ID NO 13, or the protein which is encoded by this gene and has the amino acid sequence specified under SEQ ID NO 12 or SEQ ID NO 14, is involved, in potato plants, in the synthesis of the amylopectin side chains or in the phosphorylation of starch.

In connection with the present invention, the term "identity" is to be understood as meaning the number of amino acids/nucleotides which concur with those of other proteins/nucleic acids, expressed as a percentage. The identity is preferably determined using computer programs. If sequences which are being compared with each other are of differing lengths, the identity is to be determined such that the number of amino acids which the shorter sequence has in common with the longer sequence determines the percentage identity. The identity is preferably determined using the ClustalW computer program (Thompson et al., 1994, Nucleic Acids Research 22, 4673-4680), which is known and available to the public. ClustalW is made publicly available by Julie Thompson (Thompson@EMBL-Heidelberg.de) and Toby Gibson (Gibson@EMBL-Heidelberg.de), European Molecular Biology Laboratory, Meyerhofstrasse 1, 69117 Heidelberg, Germany. ClustalW can also be downloaded from a variety of internet sites, including from IGBMC (Institut de Génétique et de Biologie Moléculaire et Cellulaire, B.P. 163, 67404 Illkirch Cedex, France; (ftp://ftp-igbmc.u.-strasbg.fr/pub/) and from EBI (ftp://ftp.ebi.ac.uk/pub/software/) and from all mirrored internet sites belonging to the EBI (European Bioinformatics Institute, Welcome Trust Genome Campus, Hinxton, Cambridge CB10 ISD, UK).

Preference is given to using version 1.8 of the ClustalW computer program for determining the identity between the proteins which are described here and other proteins. The following parameter settings are to be used in this connection: KTUPLE=1, TOPDIAG=5, WINDOW=5, PAIRGAP=3, GAPOPEN=10, GAPEXTEND=0.05, GAPDIST=8, MAXDIV=40, MATRIX=GONNET, ENDGAPS(OFF), NOPGAP, NOHGAP.

Preference is given to using version 1.8 of the ClustalW computer program for determining the identity between the nucleotide sequences of the nucleic acid molecules which are described herein and the nucleotide sequences of other nucleic acid molecules. The following parameter settings are to be used in this connection:
KTUPLE=2, TOPDIAGS=4, PAIRGAP=5, DNAMATRIX: IUB, GAPOPEN=10, GAPEXT=5, MAXDIV=40, TRANSITIONS: unweighed.

One option for finding similar sequences is to carry out sequence database searches. In the searches, one or more sequences are predetermined to be what is termed the query. Statistical computer programs are then used to compare this query sequence with sequences which are contained in the chosen databases. Such database searches (blast searches) are known to the skilled person and can be carried out using the databases provided by different suppliers. If such a database search is carried out using the NCBI (National Center for Biotechnology Information, http://www.ncbi.nim.nih.gov/) database, the standard settings which are predetermined for the given comparison query should then be used. In the case of protein sequence comparisons (blastp), these settings are as follows: Limit entrez=not activated; Filter=low complexity activated; Expect value=10; word size=3; Matrix=BLOSUM62; Gap costs: Existence=11, Extension=1. Such a search also results in the percentage identity between the query sequence and the similar sequences which are found in the databases being presented in addition to other parameters.

In one embodiment of the present invention, the genetic modification of the plant cells according to the invention or of the plants according to the invention is elicited by mutagenesis of one or more genes. The nature of the mutation is immaterial in this regard as long as it leads to a reduction in the GBSSI and/or SSIII and/or BEI activities(-ies) and to a reduction in the expression of the gene specified under SEQ ID NO 11 or SEQ ID NO 13.

In connection with the present invention, the term "mutagenesis" is to be understood as meaning any type of introduced mutations, such as deletions, point mutations (nucleotide substitutions), insertions, inversions, gene conversions or chromosome translocations.

A mutation which leads to a reduction in the GBSSI and/or SSIII and/or BEI activities(-ies) and to a reduction in the expression of the gene specified under SEQ ID NO 11 or SEQ ID NO 13 can arise spontaneously in a plant and the corresponding plants can be selected and propagated using the methods which are described below.

A mutation which leads to a reduction the GBSSI and/or SSIII and/or BEI activities(-ies) and to a reduction in the expression of the gene specified under SEQ ID NO 11 or SEQ ID NO 13 can also be produced by using chemical agents or energy-rich radiation (e.g. x-radiation, neutron radiation, gamma radiation or UV radiation).

Agents which can be used for producing chemically induced mutations, and the mutations which arise in this connection as a result of the action of the corresponding mutagens, are described, for example, by Ehrenberg and Husain (1981, Mutation Research 86, 1-113) and Müller (1972, Biologisches Zentralblatt 91 (1), 31-48). The generation of rice mutants using gamma rays, ethylmethane sulfonate (EMS), N-methyl-N-nitrosourea or sodium azide ($NaN_3$) is described, for example, by Jauhar and Siddiq (1999, Indian Journal of Genetics, 59 (1), 23-28), Rao (1977, Cytologica 42, 443-450), Gupta and Sharma (1990, Oryza 27, 217-219) and Satoh and Omura (1981, Japanese Journal of Breeding 31 (3), 316-326). The generation of wheat mutants using $NaN_3$ or maleic hydrazide is described by Arora et al. (1992, Annals of Biology 8 (1), 65-69). Scarascia-Mugnozza et al. (1993, Mutation Breeding Review 10, 1-28) provide a review of the generation of wheat mutants using different types of energy-rich radiation and chemical agents. Svec et al. (1998, Cereal Research Communications 26 (4), 391-396) describe the use of N-ethyl-N-nitrosourea for generating mutants in triticale. The use of MMS (methylmethanesulfonic acid) and gamma radiation for generating millet mutants has been described by Shashidhara et al. (1990, Journal of Maharashtra Agricultural Universities 15 (1), 20-23).

The production of mutants in plant species which chiefly multiply vegetatively has been described, for example, in the case of potatoes which produce an altered starch (Hovenkamp-Hermelink et al., 1987, see above) and in the case of mint in which the oil yield is increased or the oil quality is altered (Dwivedi et al., 2000, Journal of Medicinal and Aromatic Plant Sciences 22, 460-463).

All these methods are in principle suitable for producing the plant cells according to the invention or the plants according to the invention.

Methods which are known to the skilled person can be used to find mutations in the corresponding genes, in particular in genes which encode GBSSI, SSIII or BEI or genes which exhibit the nucleotide sequence specified under SEQ ID NO 11 or SEQ ID NO 13. In particular, it is possible to make use, for this purpose, of analyses which are based on hybridizations with probes (southern blotting), amplification by means of the polymerase chain reaction (PCR), sequencing of relevant genomic nucleic acid fragments and searching for individual nucleotide substitutions. A method for identifying mutations with the aid of hybridization patterns is, for example, that of searching for restriction fragment length differences (restriction fragment length polymorphisms, RFLPs) (Nam et al., 1989, The Plant Cell 1, 699-705; Leister and Dean, 1993, The Plant Journal 4 (4), 745-750). An example of a PCR-based method is that of analyzing amplified fragment length differences (amplified fragment length polymorphisms, AFLPs) (Castiglioni et al., 1998, Genetics 149, 2039-2056; Meksem et al., 2001, Molecular Genetics and Genomics 265, 207-214; Meyer et al., 1998, Molecular and General Genetics 259, 150-160). It is also possible to use restriction endonuclease-cut amplified fragments (cleaved amplified polymorphic sequences, CAPS) for identifying mutations (Konieczny and Ausubel, 1993, The Plant Journal 4, 403-400; Jarvis et al., 1994, Plant Mol. Biol. 24, 685-687; Bachem et al., 1996, The Plant Journal 9 (5), 745-753). Methods for determining SNPs have been described by, inter alia, Qi et al. (2001, Nucleic Acids Research 29 (22), e116), Drenkard et al. (2000, Plant Physiology 124, 1483-1492) and Cho et al. (1999, Nature Genetics 23, 203-207). Methods which enable many plants to be examined within a short time for the presence of mutations in given genes are particularly suitable. Such a method, i.e. what is termed TILLING (targeting-induced local lesions in genomes) has been described by McCallum et al. (2000, Plant Physiology 123, 439-442).

All these methods are in principle suitable for identifying plant cells according to the invention or the plants according to the invention.

Hoogkamp et al. (2000, Potato Research 43, 179-189) have produced stable monoploid mutants from a potato mutant (amf) which was produced by means of chemical mutagenesis. These plants no longer synthesize any active GBSSI and therefore produce a starch which is amylose-free. The monoploid potato plants which are obtained can be used as the starting material for further mutageneses.

A reduction in the GBSSI and/or SSIII and/or BEI activities(-ies), and a reduction in the expression of the gene specified under SEQ ID NO 11 or SEQ ID No 13, can be achieved by reducing the expression of one or more of the gene(s) which encode(s) GBSSI or SSIII or BEI and which exhibit(s) the nucleotide sequence specified under SEQ ID NO 11 or SEQ ID NO 13 and/or by reducing the quantity of relevant enzyme material in the plant cells and/or by reducing the enzymic activity of the relevant proteins in the plant cells.

The reduction in the expression can, for example, be determined by measuring the quantity of transcripts which encode the relevant enzymes, e.g. by means of Northern blot analysis or RT-PCR. In this connection, a reduction preferably denotes a reduction in the quantity of transcripts by at least 50%, in particular by at least 70%, preferably by at least 85%, and particularly preferably by at least 95%, as compared with the quantity in corresponding wild-type plant cells.

The reduction in the quantity of GBSSI and/or SSIII and/or BEI, which results in a reduction in the relevant enzyme activities(-ies) in the plant cells, can be determined, for example, using immunological methods such as Western blot analysis, ELISA (enzyme-linked immunosorbent assay) or RIA (radioimmune assay). In this connection, a reduction preferably denotes a reduction in the quantity of relevant protein by at least 50%, in particular by at least 70%, preferably by at least 85%, and particularly preferably by at least 95%, as compared with that in corresponding wild-type plant cells.

In another embodiment of the present invention, the genetic modification of the plant cell according to the invention comprises introducing one or more foreign nucleic acid molecules/polynucleotides whose presence and/or expression leads to a reduction in the GBSSI and/or SSIII and/or BEI activities(-ies), and to a reduction in the expression of the gene specified under SEQ ID NO 11 or SEQ ID NO 13, as compared with that/those in corresponding wild-type plant cells. In particular, the term genetic modification is understood as meaning the introduction of homologous and/or heterologous and/or mutagenized foreign nucleic acid molecules/polynucleotides into a plant cell, with said introduction of these molecules leading to a reduction in the GBSSI and/or SSIII and/or BEI activities(-ies) and to a reduction in the expression of the gene which is specified under SEQ ID NO 11 or SEQ ID NO 13. In this way, it is consequently possible to generate transgenic plant cells according to the invention.

In this connection, the term "transgenic" means that the genetic information in the plant cells according to the invention differs from that of corresponding wild-type plant cells as a result of the introduction of a foreign nucleic acid molecule/polynucleotide, or several foreign nucleic acid molecules/polynucleotides, into the cell.

In connection with the present invention, the term "foreign nucleic acid molecule/polynucleotide" or "foreign nucleic acid molecules/polynucleotides" is to be understood as meaning such a molecule which either naturally does not occur in corresponding wild-type plant cells or which does not occur naturally in the specific spatial arrangement in corresponding wild-type plant cells, or which is located at a site in the genome of the plant cell at which it does not naturally occur. Preference is given to the foreign nucleic acid molecule/polynucleotide being a recombinant molecule which is composed of different elements whose combination, or specific spatial arrangement, does not occur naturally in plant cells.

The foreign nucleic acid molecule(s)/polynucleotide(s) which is/are used for the genetic modification can be one integrated nucleic acid construct or several separate nucleic acid constructs, in particular what are termed single, double, triple or quadruple constructs. Thus, the foreign nucleic acid molecule/polynucleotide can, for example, be what is termed a "quadruple construct", which is understood as meaning a single vector for plant transformation, which vector contains the genetic information for inhibiting the expression of one or more endogenous GBSSI genes, for inhibiting the expression of one or more SSIII genes, for inhibiting the expression of one or more BEI genes and for inhibiting the expression of the gene specified under SEQ ID NO 11 or SED ID NO 13, or whose presence or whose expression leads to a reduction in the GBSSI, SSIII and BEI activities and to a reduction in the expression of the gene specified under SEQ ID NO 11 or SEQ ID NO 13.

In another embodiment, the foreign nucleic acid molecule/polynucleotide can be what is termed a "double construct", which is understood as meaning a vector for plant transformation which contains the genetic information for inhibiting the expression of two of the four target genes (GBSSI gene, SSIII gene, BEI gene, gene having the nucleotide sequence specified under SEQ ID NO 11 or SEQ ID NO 13) or whose presence or whose expression leads to a reduction in the activity of two of the four enzymes (GBSSI, SSIII, BEI or protein having the amino acid sequence specified under SEQ ID NO 12 or SEQ ID NO 14). In this exemplary embodiment of the invention, the expression of the third and fourth target genes is inhibited, and/or the activities of the third and fourth enzymes are reduced, using a separate foreign nucleic acid molecule/polynucleotide which contains the appropriate genetic information for inhibiting these two additional target genes.

In another embodiment of the invention, several different foreign nucleic acid molecules/polynucleotides, rather than a quadruple construct, are introduced into the genome of the plant cell, with one of these foreign nucleic acid molecules being, for example, a DNA molecule which, for example, constitutes a cosuppression construct which brings about a reduction in the expression of one or more endogenous GBSSI genes and leads to the inhibition of the expression of the gene specified under SEQ ID NO 11 or SEQ ID NO 13, and another foreign nucleic acid molecule being a DNA molecule which, for example, encodes an antisense RNA which beings about a reduction in the expression of one or more endogenous SSIII and/or BEI genes. In principle, however, the use of any combination of antisense, cosuppression, ribozyme and double-stranded RNA constructs or in-vivo mutagenesis which leads to a simultaneous reduction in the expression of endogenous genes which encode BGSSI, SSIII and BEI or which exhibit the nucleotide sequence specified under SEQ ID NO 11 or SEQ ID NO 13, or which leads to a simultaneous reduction in the GBSSI, SSIII or BEI activities and to inhibition of the expression of the gene specified under SEQ ID NO 11 or SEQ ID NO 13, is also suitable when constructing the foreign nucleic acid molecules.

In this connection, the foreign nucleic acid molecules can either be inserted into the genome of the plant cell simultaneously (cotransformation) or consecutively, that is chronologically one after the other (supertransformation).

The foreign nucleic acid molecules/polynucleotides can also be introduced into different individual plants belonging to a species. In this connection, it is possible to generate plants in which the activities(-ies) of one enzyme (e.g. GBSSI or SSIII or BEI) or of two enzymes (e.g. GBSSI and SSIII or GBSSI and BEI or SSIII and BEI) or of three enzymes is/are reduced. Subsequent crossing can then be used to generate plants in which the activities of all three enzymes (GBSSI, SSIII and BEI) are reduced and the expression of the gene specified under SEQ ID NO 11 or SEQ ID NO 13 is reduced.

It is furthermore possible, for the purpose of introducing a foreign nucleic acid molecule/polynucleotide, or for the purpose of producing the plant cells according to the invention or the plants according to the invention, to use a mutant instead of a wild-type plant cell or wild-type plant, with the mutant being distinguished by the fact that it already exhibits a reduced activity of one or more enzymes (GBSSI, SSIII, BEI and protein having the amino acid sequence specified under SEQ ID NO 12 or SEQ ID NO 14). The mutants can be either spontaneously arising mutants or else mutants which have been generated by the selective use of mutagens. Possibilities for generating such mutants have been described above.

The plant cells according to the invention can also be produced by using what is termed insertion mutagenesis (review article: Thorneycroft et al., 2001, Journal of Experimental Botany 52 (361), 1593-1601). "Insertion mutagenesis" is to be understood, in particular, as being the insertion of transposons or of what is termed transfer DNA (T-DNA) into a gene which encodes GBSSI and/or SSIII and/or BEI and/or has the nucleotide sequence specified under SEQ ID NO 11 or SEQ NO 13.

The transposons can be either those which naturally occur in a wild-type plant cell (endogenous transposons) or those which do not naturally occur in said cell but which are introduced into the cell using genetic methods such as transformation of the cell (heterologous transposons). The skilled person is familiar with using transposons to change the expression of genes. Ramachandran and Sundaresan (2001, Plant Physiology and Biochemistry 39, 234-252) have provided a review regarding the use of endogenous and heterologous transposons as tools in plant biotechnology. The possibility of identifying mutants in which specific genes have been inactivated by transposon insertion mutagenesis is described in a review by Maes et al. (1999, Trends in Plant Science 4 (3), 90-96). The use of endogenous transposons to generate rice mutants has been described by Hirochika (2001, Current Opinion in Plant Biology 4, 118-122). The use of endogenous retrotransposons to identify corn genes is described, for example, by Hanley et al. (2000, The Plant Journal 22 (4), 557-566). Kumar and Hirochika (2001, Trends in Plant Science 6 (3), 127-134) describe the possibility of using retrotransposons to produce mutants, and also describe methods for identifying mutants. The activities of heterologous transposons in different species have been described both in the case of dicotyledonous plants and in the case of monocotyledonous plants: e.g. in the case of rice (Greco et al., 2001, Plant Physiology 125, 1175-1177; Liu et al., 1999, Molecular and General Genetics 262, 413-420; Hiroyuki et al., 1999, The Plant Journal 19 (5), 605-613; Jeon and Gynheung, 2001, Plant Science 161, 211-219), barley (Koprek et al., 2000, The Plant Journal 24 (2), 253-263), *Arabidopsis thaliana* (Aarts et al., 1993, Nature 363, 715-717; Schmidt and Willmitzer, 1989, Molecular and General Genetics 220, 17-24; Altmann et al., 1992, Theoretical and Applied Genetics 84, 371-383; Tissier et al., 1999, The Plant Cell 11, 1841-1852), tomato (Belzile and Yoder, 1992, The Plant Journal 2 (2), 173-179) and potato (Frey et al., 1989, Molecular and General Genetics 217, 172-177; Knapp et al., 1988, Molecular and General Genetics 213, 285-290).

In principle, the plant cells according to the invention and the plants according to the invention can be produced using either homologous or heterologous transposons, with the use of homologous transposons also having to be understood as meaning the transposons which are already naturally present in the plant genome.

T-DNA insertion mutagenesis is based on specific segments (T-DNA) of *Agrobacterium* Ti plasmids being able to integrate into the genome of plant cells. The site for the integration into the plant chromosome is not fixed; rather, integration can take place at any arbitrary site. If the T-DNA integrates into a segment of the chromosome which constitutes a gene function, the integration can then lead to a change in the expression of the gene and consequently also to a change in the activity of a protein which is encoded by the gene in question. In particular, integration of a T-DNA into the coding region of a gene frequently results in the relevant cell either no longer being able to synthesize the corresponding protein at all or else no longer being able to synthesize it in an active form. The use of T-DNA insertions for generating mutants has been described, for example, in the case of *Arabidopsis thaliana* (Krysan et al., 1999, The Plant Cell 11, 2283-2290; Atipiroz-Leehan and Feldmann, 1997, Trends in Genetics 13 (4), 152-156; Parinov and Sundaresan, 2000, Current Opinion in Biotechnology 11, 157-161) and rice (Jeon and An, 2001, Plant Science 161, 211-219; Jeon et al., 2000, The Plant Journal 22 (6), 561-570). Methods for identifying mutants which have been generated using T-DNA insertion mutagenesis have been described, inter alia, by Young et al. (2001, Plant Physiology 125, 513-518), Parinov et al. (1999, The Plant Cell 11, 2263-2270), Thorneycroft et al. (2001, Journal of Experimental Botany 52, 1593-1601) and McKinney et al. (1995, The Plant Journal 8 (4), 613-622).

T-DNA mutagenesis is in principle suitable for generating the plant cells according to the invention and the plants according to the invention.

In another embodiment of the present invention, the presence and/or the expression of one or more foreign nucleic acid molecules/polynucleotides leads to the expression of endogenous genes which encode GBSSI and/or SSIII and/or BEI, and/or which exhibit the nucleotide sequence specified under SEQ ID NO 11 or SEQ ID NO 13, being inhibited.

This can be achieved by means of a variety of methods which are known to a skilled person. These methods include, for example, expressing a corresponding antisense RNA or a double-stranded RNA construct, providing molecules or vectors which mediate a cosuppression effect, expressing an appropriately constructed ribozyme which specifically cleaves transcripts which encode GBSSI or SSIII or BEI, or what is termed "in-vivo mutagenesis". Furthermore, a reduction in the GBSSI and/or SSIII and/or BEI activities(-ies) and/or a reduction in the expression of the gene specified under SEQ ID NO 11 or SEQ ID NO 13 in the plant cells can also be elicited by simultaneously expressing sense and antisense RNA molecules of the respective target gene to be repressed, preferably of the GBSSI and/or SSIII and/or BEI gene and/or of the gene having the nucleotide sequence which is specified under SEQ ID NO 11 or SEQ ID NO 13. The skilled person is familiar with these methods.

In addition to this, it is known that, in planta, the formation of double-stranded RNA molecules of promoter sequences can lead in trans to methylation and transcriptional inactivation of homologous copies of this promoter (Mette et al., 2000, EMBO J. 19, 5194-5201).

In order to employ antisense or cosuppression technology for inhibiting gene expression, it is possible, for example, to use a DNA molecule which comprises the entire sequence encoding GBSSI and/or SSIII and/or BEI and/or the nucleotide sequence which is specified under SEQ ID NO 11 or SEQ ID NO 13, including any flanking sequences which may possibly be present, or else use DNA molecules which only comprise parts of the coding sequence, with these parts having to be sufficiently long to bring about an antisense effect or cosuppression effect in the cells. In general, sequences having a minimum length of 15 bp, preferably having a minimum length of 20-30 bp, particularly preferably having a length of 100-500 bp, in particular sequences having a length of more than 500 bp, are suitable for exerting very efficient antisense or cosuppression inhibition.

The use of polynucleotide sequences which have a high degree of identity with the sequences which occur endogenously in the plant cell and which encode GBSSI or SSIII or BEI, or which are depicted under SEQ ID NO 11 or SEQ ID NO 13, is also suitable for antisense or cosuppression approaches. The minimum identity should be greater than approx. 65%. The use of sequences having identifies of at least 90%, in particular of between 95 and 100%, is to be preferred.

It is furthermore also possible to conceive of using introns, i.e. noncoding regions of genes which encode GBSSI or SSII or BEI or which exhibit the nucleotide sequence depicted under SEQ ID NO 11 or SEQ ID NO 13, for achieving an antisense or cosuppression effect.

The use of intron sequences for inhibiting the expression of genes which encode starch biosynthesis proteins has been described in WO 97/04112, WO 97/04113, WO 98/37213 and WO 98/37214.

The skilled person knows how he can achieve an antisense or cosuppression effect. The method of cosuppression inhibition has been described, for example, by Jorgensen (1990, Trends Biotechnol. 8, 340-344), Niebel et al. (1995, Top. Microbiol. Immunol. 197, 91-103), Flavell et al. (1995, Curr. Top. Microbiol. Immunol. 197, 43-46), Palauqui and Vaucheret (1995, Plant Mol. Biol. 29, 149-159), Vaucheret et al. (1995, Mol. Gen. Genet. 248, 311-317) and de Borne et al. (1994, Mol. Gen. Genet. 243, 613-621).

Expression of ribozymes for the purpose of reducing the activity of particular enzymes in cells is also known to the skilled person and is described, for example, in EP-B1 0321201. The expression of ribozymes in plant cells has been described, for example, by Feyter et al. (1996, Mol. Gen. Genet. 250, 329-338).

Furthermore, a reduction in the GBSSI and/or SSIII and/or BEI activities(-ies) and/or a reduction in the expression of the gene depicted under SEQ ID NO 11 or SEQ ID NO 13 in the plant cells can also be achieved by what is termed "in-vivo mutagenesis", in which transformation of cells is used to introduce a hybrid RNA-DNA oligonucleotide ("chimeroplast") into cells (Kipp et al., poster session at the 5th International Congress of Plant Molecular Biology, 21-27 Sep. 1997, Singapore; R. A. Dixon and C. J. Arntzen, meeting report relating to Metabolic Engineering in Transgenic Plants, Keystone Symposia, Copper Mountain, Colo., USA, 1997, TIBTECH 15, 441-447; WO 95/15972; Kren et al., 1997, Hepatology 25, 1462-1468; Cole-Strauss et al., 1996, Science 273, 1386-1389 and Beetham et al., 1999, PNAS 96, 8774-8778).

While a part of the DNA component of the RNA-DNA oligonucleotide is homologous with a polynucleotide sequence in an endogenous GBSSI and/or SSIII and/or BEI gene and/or a gene depicted under SEQ ID NO 11 or SEQ ID NO 13, it exhibits a mutation as compared with the polynucleotide sequence of an endogenous GBSSI or SSIII or BEI gene or contains a heterologous region which is surrounded by the homolgous regions. As a result of base pairing of the homologous regions of the RNA-DNA oligonucleotide and of the endogenous polynucleotide, followed by homologous recombination, the mutation or heterologous region contained in the DNA component of the RNA-DNA oligonucleotide can be transferred into the genome of a plant cell. This leads to a reduction in the activities(-ies) of GBSSI and/or SSIII and/or BEI and/or to a reduction in the expression of the gene which is specified under SEQ ID NO 11 or SEQ ID NO 13.

In addition, a reduction in the GBSSI and/or SSIII and/or BEI activities(-ies) in the plant cells can also be elicited by simultaneously expressing sense and antisense RNA molecules of the respective target gene to be repressed, preferably of the GBSSI and/or SSIII and/or BEI gene and/or of the gene which is specified in SEQ ID NO 11 or SEQ ID NO 13.

This can be achieved, for example, by using chimeric constructs which contain inverted repeats of the respective target gene or parts of the target gene. In this connection, the chimeric constructs encode sense and antisense RNA molecules of the respective target gene. In planta, sense and antisense RNA are synthesized simultaneously as one RNA molecule, with sense and antisense RNA being separated from each other by a spacer and being able to form a double-stranded RNA molecule (RNAi technology).

It has been shown that introducing inverted-repeaT-DNA constructs into the genome of plants is a very efficient method for repressing the genes which correspond to the inverted-repeaT-DNA constructs (Waterhouse et al., 1998, Proc. Natl. Acad. Sci. USA 95, 13959-13964; Wang and Waterhouse, 2000, Plant Mol. Biol. 43, 67-82; Singh et al., 2000, Biochemical Society Transactions 28 (6), 925-927; Liu et al., 2000, Biochemical Society Transactions 28 (6), 927-929; Smith et al., 2000, Nature 407, 319-320; WO 99/53050). Sense and antisense sequences of the target gene or the target genes can also be expressed separately from each other using identical or different promoters (Nap et al., 6th International Congress of Plant Molecular Biology, 18-24 Jun. 2000, Quebec, poster S7-27, lecture session S7).

It is consequently also possible to reduce the GBSSI and/or SSIII and/or BEI activities(-ies), and to reduce the expression of the gene specified under SEQ ID NO 11 or SEQ ID NO 13, in the plant cells by producing double-stranded RNA molecules of GBSSI or SSIII or BEI genes or genes having the nucleotide sequence which is depicted under SEQ ID NO 11 or SEQ ID NO 13. For this, preference is given to introducing inverted repeats of DNA molecules which are derived from GBSSI or SSIII or BEI genes, or genes having the nucleotide sequence depicted under SEQ ID NO 11 or SEQ ID NO 13, or cDNAs, into the genome of plants, with the DNA molecules which are to be transcribed being under the control of a promoter which regulates the expression of said DNA molecules.

In addition to this, it is known that, in plants, forming double-stranded RNA molecules of promoter DNA molecules can lead in trans to methylation and transcriptional inactivation of homolgous copies of these promoters, which will be termed target promoters in that which follows (Mette et al., 2000, EMBO J. 19, 5194-5201).

It is consequently possible to use inactivation of the target promoter to reduce the expression of a particular target gene (e.g. GBSSI, SSIII or BEI gene; gene having the nucleotide sequence depicted under SEQ ID NO 11 or SEQ ID NO 13) which is naturally under the control of this target promoter.

That is, in this case, the DNA molecules which comprise the target promoters of the genes (target genes) to be repressed are not, in contrast to the original function of promoters in plants, being used as elements for regulating the expression of genes or cDNAs but, instead, themselves being used as transcribable DNA molecules.

In order to generate the double-stranded target promoter RNA molecules in planta, where the molecules can be present as RNA hairpin molecules, preference is given to using constructs which contain inverted repeats of the target promoter DNA molecules, with the target promoter DNA molecules being under the control of a promoter which regulates the expression of said target promoter DNA molecules. These constructs are then introduced into the genome of plants. The expression of the inverted repeats of said target promoter DNA molecules leads, in planta, to the formation of double-stranded target promoter RNA molecules (Mette et al., EMBO J. 19, 5194-5201). These molecules can inactivate the target promoter.

Reduction of the GBSSI and/or SSIII and/or BEI activities (-ies), and inhibition of the expression of the gene specified under SEQ ID NO 11 or SEQ ID NO 13, in the plant cells can consequently also be achieved by generating double-stranded RNA molecules of promoter sequences of GBSSI or SSIII or BEI genes or of genes having the nucleotide sequence depicted under SEQ ID NO 11 or SEQ ID NO 13. For this, preference is given to introducing inverted repeats of promoter DNA molecules of GBSSI and/or SSIII and/or BEI promoters into the genome of plants, with the target promoter DNA molecules (GBSSI, SSIII or BEI promoter) to be transcribed being under the control of a promoter which regulates the expression of said target promoter DNA molecules.

The skilled person also knows that he can reduce the GBSSI and/or SSIII and/or BEI activities(-ies), and inhibit the expression of the gene specified under SEQ ID NO 11 or SEQ ID NO 13, by expressing nonfunctional derivatives, in particular transdominant mutants, of the enzymes and/or by expressing antagonists/inhibitors of the enzymes.

Antagonists/inhibitors of the enzymes can, for example, be antibodies, antibody fragments or molecules having similar binding properties. For example, a cytoplasmic scFv antibody has been used to modulate the activity of the phytochrome A protein in recombinantly altered tobacco plants (Owen, 1992, Bio/Technology 10, 790-794; Review: Franken et al., 1997, Current Opinion in Biotechnology 8, 411-416; Whitelam, 1996, Trends Plant Sci. 1, 268-272).

In a general manner, any promoter which is active in plant cells is suitable for expressing the foreign nucleic acid molecule/polynucleotide (the foreign nucleic acid molecules/polynucleotides). In this connection, the promoter can be selected such that the expression takes place constitutively in the plants according to the invention or only in one particular tissue, at a particular timepoint in the development of the plant or at a timepoint which is determined by external influences. The promoter can be homologous or heterologous in relation to the plant.

Examples of appropriate promoters for expressing nucleic acids/polynucleotides which reduce the activity of a target gene are the promoter of the cauliflower mosaic virus 35S RNA and the corn ubiquitin promoter for constitutive expression, the patatin gene promoter B33 (Rocha-Sosa et al., 1989, EMBO J. 8, 23-29), the MCPI promoter of the potato metallocarboxypeptidase inhibitor gene (HU 9801674) or the potato GBSSI promoter (WO 92/11376) for tuber-specific expression in potatoes or a promoter which allows expression only in photosynthetically active tissues, e.g. the ST-LS1 promoter (Stockhaus et al., 1987, Proc. Natl. Acad. Sci. USA 84, 7943-7947; Stockhaus et al., 1989, EMBO J. 8, 2445-2451), the Ca/b promoter (see, for example, U.S. Pat. No. 5,656,496; U.S. Pat. No. 5,639,952; Bansal et al., 1992, Proc. Natl. Acad. Sci. USA 89, 3654-3658) and the Rubisco SSU promoter (see, for example, U.S. Pat. No. 5,034,322; U.S. Pat. No. 4,962,028) or, for endosperm-specific expression, the glutelin promoter (Leisy et al., 1990, Plant Mol. Biol. 14, 41-50; Zheng et al., 1993, Plant J. 4, 357-366; Yoshihara et al., 1996, FEBS Lett. 383, 213-218), the shrunken-1 promoter (Werr et al., 1985, EMBO J. 4, 1373-1380), the wheat HMG promoter, the USP promoter, the phaseolin promoter or corn zein gene promoters (Pedersen et al., 1982, Cell 29, 1015-1026; Quatroccio et al., 1990, Plant Mol. Biol. 15, 81-93).

The potato patatin gene, MCPI and GBSSI promoters are promoters which are preferred for expressing the foreign nucleic acid molecule/polynucleotide (the foreign nucleic acid molecules/polynucleotides).

It is particularly advantageous to express the foreign nucleic acid molecule/polynucleotide (the foreign nucleic acid molecules/polynucleotides) in those organs in the plant which store starch. The examples of these organs are the tuber of the potato plant or the grains or endosperm of corn, wheat or rice plants. Preference is therefore given to using promoters which mediate expression in these organs.

However, it is also possible to use promoters which are only activated at a timepoint which is determined by external influences (see, for example, WO 93/07279). Promoters of heat shock proteins, which permit simple induction, may be of particular interest in this connection. It is furthermore possible to use seed-specific promoters, such as the Vicia faba USP promoter, which ensures seed-specific expression in Vicia faba and other plants (Fiedler et al., 1993, Plant Mol. Biol. 22, 669-679; Bäumlein et al., 1991, Mol. Gen. Genet. 225, 459-467), and also fruit-specific promoters, as described, for example, in WO 91/01373.

It is furthermore possible for a termination sequence, which serves the purpose of correctly terminating the transcription and of adding a poly A tail to the transcript, with the tail being attributed a function in stabilizing the transcripts, to be present. These elements are described in the literature (see, for example, Gielen et al., 1989, EMBO J. 8, 23-29) and can be substituted as desired.

A large number of techniques are available for introducing DNA into a host plant cell. These techniques include transforming plant cells with T-DNA using *Agrobacterium tumefaciens* or *Agrobacterium rhizogenes* as transforming agent, fusing protoplasts, injecting, electroporating the DNA, introducing the DNA by means of a biolistic approach, and also other possibilities.

The use of the *agrobacterium*-mediated transformation of plant cells has been investigated intensively and described adequately in EP-A 0120516 and by Hoekema (1985, The Binary Plant Vector System Offsetdrukkerij Kanters B. V., Alblasserdam, Chapter V), Fraley et al. (Crit. Rev. Plant Sci. 4, 1-46) and An et al. (1985, EMBO J. 4, 277-287). For information regarding potato transformation, see, for example, Rocha-Sosa et al., 1989, EMBO J. 8, 29-33.

The use of *agrobacterium* transformation-based vectors for transforming monocotyledonous plants has also been described (Chan et al., 1993, Plant. Mol. Biol. 22, 491-506; Hiei et al., 1994, Plant J. 6, 271-282; Deng et al., 1990, Science in China 33, 28-34; Wilmink et al., 1992, Plant Cell Reports 11, 76-80; May et al., 1995, Bio/Technology 13, 486-492; Conner and Domisse, 1992, Int. J. Plant Sci. 153, 550-555; Ritchie et al, 1993, Transgenic Res. 2, 252-265). Transformation using the biolistic approach (Wan and Lemaux, 1994, Plant Physiol. 104, 37-48; Vasil et al., 1993, Bio/Technology 11, 1553-1558; Ritala et al., 1994, Plant Mol. Biol. 24, 317-325; Spencer et al., 1990, Theor. Appl. Genet. 79, 625-631), protoplast transformation, electroporation of partially permeabilized cells, and the use of glass fibers to introduce DNA, represent alternative systems for transforming monocotyledonous plants. The transformation of corn, in particular, has been described repeatedly in the literature (see, for example, WO 95/06128, EP-A 0513849, EP-A 0465875, EP-A 0292435; Fromm et al., 1990, Biotechnology 8, 833-844; Gordon-Kamm et al., 1990, Plant Cell 2, 603-618; Koziel et al., 1993, Biotechnology 11, 194-200; Moroc et al., 1990, Theor. Appl. Genet. 80, 721-726).

The successful transformation of other cereal types has also been described, for example in the case of barley (Wan and Lemaux, see above; Ritala et al., see above; Krens et al., 1982, Nature 296, 72-74) and in the case of wheat (Nehra et al., 1994, Plant J. 5, 285-297).

The present invention also relates to a plant cell which is genetically modified, with the genetic modification leading to reduction of the GBSSI, SSIII and BEI activities and to inhibition of the expression of the gene specified under SEQ ID NO 11 or SEQ NO 13 as compared with those of corresponding wild-type plant cells or wild-type plants, and which contains at least one foreign nucleic acid which is selected from the group consisting of a) polynucleotides which encode at least one antisense RNA which leads to a reduction in the expression of at least one endogenous GBSSI gene and/or to a reduction in the expression of at least one endogenous SSIII gene and/or to a reduction in the expression of at least one endogenous BEI gene and/or to a reduction in the expression of at least one gene having the nucleotide sequence specified under SEQ ID NO 11 or SEQ ID NO 13;

b) polynucleotides which lead, by way of a cosuppression effect, to a reduction in the expression of at least one endogenous GBSSI gene and/or to a reduction in the expression of at least one endogenous SSIII gene and/or to a reduction in the expression of at least one endogenous BEI gene and/or to a reduction in the expression of at least one gene having the nucleotide sequence specified under SEQ ID NO 11 or SEQ ID NO 13;

c) polynucleotides which encode at least one ribozyme which specifically cleaves transcripts of at least one endogenous GBSSI gene and/or of at least one SSIII gene and/or of at least one BEI gene and/or of at least one gene having the nucleotide sequence specified under SEQ ID NO 11 or SEQ ID NO 13;

d) polynucleotides which are introduced by means of in-vivo mutagenesis and which lead to a mutation or an insertion in at least one endogenous GBSSI gene and/or to a mutation or an insertion in at least one endogenous SSIII gene and/or to a mutation or an insertion in at least one endogenous BEI gene and/or to a mutation or an insertion in at least one gene having the nucleotide sequence specified under SEQ ID NO 11 or SEQ ID NO 13, with the mutation or insertion leading to a reduction in the expression of said gene or to the synthesis of inactive GBSSI and/or of inactive SSIII and/or of inactive BEI and/or of an inactive protein having the amino acid sequence specified under SEQ ID NO 12 or SEQ ID NO 14;

e) polynucleotides which encode at least one antisense RNA and at least one sense RNA, with said antisense RNA and said sense RNA being able to form a double-stranded RNA molecule which leads to a reduction in the expression of at least one endogenous GBSSI gene and/or to a reduction in the expression of at least one endogenous SSIII gene and/or to a reduction in the expression of at least one endogenous BEI gene and/or to a reduction in the expression of at least one gene having the nucleotide sequence specified under SEQ ID NO 11 or SEQ ID NO 13;

f) polynucleotides which contain transposons, with the integration of the transposon sequences leading to a mutation or an insertion in at least one endogenous GBSSI gene and/or to a mutation or an insertion in at least one endogenous SSIII gene and/or to a mutation or an insertion in at least one endogenous BEI gene, and/or to a mutation or an insertion in at least one gene having the nucleotide sequence specified under SEQ ID NO 11 or SEQ ID NO 13, with the mutation or insertion leading to a reduction in the expression of said gene or to the synthesis of inactive GBSSI and/or of inactive SSIII and/or of inactive BEI and/or of an inactive protein having the amino acid sequence specified under SEQ ID NO 12 or SEQ ID NO 14; and g) T-DNA molecules which, by insertion in at least one endogenous GBSSI gene and/or by insertion in at least one endogenous SSIII gene and/or by insertion in at least one endogenous BEI gene and/or by insertion in at least one gene having the nucleotide sequence specified under SEQ ID NO 11 or SEQ ID NO 13, lead to a reduction in the expression of said gene or to the synthesis of inactive GBSSI and/or of inactive SSIII and/or of inactive BEI and/or of an inactive protein having the amino acid sequence specified under SEQ ID NO 12 or SEQ ID NO 14.

The present invention also relates to any type of material for propagating plants according to the invention.

The plant cells according to the invention can be used for regenerating whole plants.

The present invention likewise relates to the plants which can be obtained by regenerating the plant cells according to the invention.

The plants according to the invention or the plant cells according to the invention can belong to any arbitrary plant species, that is either to monocotyledonous or to dicotyledonous plants. The plants according to the invention are preferably agriculturally useful plants, i.e. plants which are cultivated by man for purposes of nutrition or for technical, in particular, industrial purposes, and their cells. The invention preferably relates to fiber-forming (e.g. flax, hemp and cotton), oil-storing (e.g. rape, sunflower and soybean), sugar-storing (e.g. sugar beet, sugar cane and sweet sorghum) and protein-storing plants (e.g. leguminosae) and their cells.

In another preferred embodiment, the invention relates to forage plants, in particular forage grasses and pasture grasses (alfalfa, clover, etc.) and vegetable plants (e.g. tomato, salad and chicory) and their cells.

In another preferred embodiment, the invention relates to starch-storing plants (e.g. wheat, barley, oats, rye, potato, corn, rice, pea and tapioca), particularly preferably potatoes, and their cells.

In connection with the present invention, the term "potato plant" or "potato" means plant species of the genus *Solanum*, particularly tuber-producing species of the genus *Solanum* and, in particular, *Solanum tuberosum*.

The present invention furthermore relates to a method for producing a plant according to the invention, in which a) a plant cell is genetically modified, with the genetic modification being the introduction of one or more foreign nucleic acid molecule(s) whose presence and/or expression leads to a reduction in the GBSSI and/or SSIII and/or BEI activities(-ies) and to a reduction in the expression of the gene specified under SEQ ID NO 11 or SEQ ID NO 13, as compared with those in corresponding wild-type plant cells, b) a plant is regenerated from step a) plant cells; and c) where appropriate, further plants are produced using the plants in accordance with step b).

The genetic modification which is introduced into the plant cell in accordance with step a) can in principle be any type of modification which leads to a reduction in the activity of one or more SSIII proteins which occur(s) endogenously in the plant and of one or more BEI proteins which occur(s) endogenously in the plant and of one or more GBSSI proteins which occur(s) endogenously in the plant and of one or more proteins which occur(s) endogenously in the plant and which exhibit(s) at least 80%, preferably 90%, particularly preferably 95%, identity with the nucleic acid molecule specified under SEQ ID NO 12 or SEQ ID NO 14.

The plants according to step (b) can be regenerated using methods which are known to the skilled person (e.g. described in "Plant Cell Culture Protocols", 1999, edtd. by R. D. Hall, Humana Press, ISBN 0-89603-549-2).

Further plants can be regenerated in accordance with step (c) of the method according to the invention by means, for example, of vegetative propagation (for example using cuttings or tubers or using a callus culture and regenerating whole plants) or by means of sexual propagation. In this connection, the sexual propagation preferably takes place in a controlled manner, i.e. selected plants possessing particular properties are crossed with each other and propagated. In this connection, the selection is preferably made such that the further plants which are obtained in accordance with step c) exhibit the genetic modification which was introduced in step a).

The disclosure content of all the documents cited in the patent application is to be included in the disclosure content of the present description of the invention.

General Methods

The following methods were used in the examples. These methods are also intended to be employed in connection with the present invention:

1 Method for Extracting Starch from Potatoes

All the tubers belonging to a line (from 4 to 5 kg) are worked up jointly in a commercially available juice extractor (Multipress automatic MP80, Braun). The starch-containing juice is collected in a 10 l bucket (ratio of the height of the bucket/diameter of the bucket=approx. 1.1) in which 200 ml of mains water containing a spoon tip (approx. 3-4 g) of sodium disulfite have been initially introduced. The bucket is then completely filled with mains water. After the starch has settled for 2 hours the supernatant is decanted off and the starch is once again suspended in 10 l of mains water and passed through a sieve having a mesh width of 125 µm. After 2 hours (the starch has once again settled at the bottom of the bucket), the aqueous supernatant is decanted once again. This washing procedure is repeated a further 3 times such that the starch is resuspended in fresh mains water a total of five times. The starches are then dried at 37° C. down to a water content of 12-17% and homogenized in a mortar. The starches are now available for analyses.

2. Starch Analysis a) Determining the Amylose/Amylopectin Ratio

Starch was isolated from potato plants, as described above, and the amylose to amylopectin ratio was determined using the method described by Hovenkamp-Hermelink et al. (1988, Potato Research 31, 241-246). The amylose content is calculated by applying the formula cited on page 243 of this article.

b) Determining the Phosphate Content in the C6 Position

In the starch, the C2, C3 and C6 positions of the glucose units can be phosphorylated. In order to determine the C6-P content of the starch, 50 mg of starch were hydrolyzed, at 95° C. for 4 h, in 500 µl of 0.7 M HCl. The mixtures were then centrifuged at 15500 g for 10 min and the supernatants were taken off. 7 µl volumes of the supernatants were mixed with 193 µl of imidazole buffer (100 mM imidazole, pH 6.9; 5 mM $MgCl_2$, 1 mM EDTA and 0.4 mM NAD). The measurement was carried out at 340 nm in a photometer. After a basal absorption had been established, the enzyme reaction was started by adding 2 U of glucose-6-phosphate dehydrogenase (from *Leuconostoc mesenteroides*, Boehringer Mannheim). The change in absorption is directly proportional to the concentration of the G-6-P content in the starch.

c) Using a Rapid Visco Analyzer (RVA) to Determine the Viscosity Properties:

The viscosity properties were determined following the method which is described in WO 01/19975.

2 g of starch (dry matter) were taken up in 25 ml of $H_2O$ (deionized water, conductivity of at least 15 megaohm) and analyzed in a Rapid Visco Analyser (Newport Scientific Pty Ltd., Investmet Support Group, Warriewod NSW 2102, Australia) for the purpose of determining the viscosity properties. The appliance was operated in accordance with the manufacturer's instructions. In order to determine the viscosity of the aqueous solution of the starch, the starch suspension was first of all stirred at 960 rpm (revolutions per minute) for 10 seconds after which it was heated at 50° C. for 1 min at a stirring rate of 160 rpm (step 1). After that, the temperature was increased from 50° C. to 95° C. at a heating rate of 12° C. per min while the stirring rate remained the same (step 2). The temperature was then kept at 95° C. for 2.5 min while the stirring rate remained the same (step 3). After that, the solution was cooled down from 95° C. to 50° C. at a cooling rate of 12° C. per min while the stirring rate remained the same (step 4). The last step (step 5) maintains the temperature of 50° C. for 2 min while the stirring rate remains the same. The viscosity was determined during the entire period.

After the program had come to an end, the stirrer was removed and the beaker was covered. The pasted starch was now available for the texture analysis after 24 h (method d) below).

In the RVA analysis profile, there are characteristic values which are presented for comparing different measurements and substances. In connection with the present invention, the following terms are to be understood as follows:

Maximum Viscosity (RVA Max):

The maximum viscosity is understood as meaning the highest viscosity value, as measured in cP (centipoise), which is achieved in step 2 or 3 of the temperature profile.

Minimum Viscosity (RVA Min):

The minimum viscosity is understood as meaning the lowest viscosity value, as measured in cP, which occurs in the temperature profile after the maximum viscosity. This normally occurs in step 3 of the temperature profile.

Final Viscosity (RVA Fin):

The final viscosity is understood as meaning the viscosity value, as measured in cP, which occurs at the end of the measurement.

Setback (RVA Set):

What is termed the "setback" is calculated by subtracting the minimum viscosity value from the final viscosity.

Pasting Temperature (RVA PT):

The pasting temperature is understood as being the temperature in the temperature profile at which the viscosity for the first time increases by 55 cP over a period of 20 sec.

d) Determining the Gel Strength (Texture Analyzer)

2 g of starch (dry matter) were pasted in 25 ml of an aqueous suspension in the RVA appliance (temperature program: see under c) "using a Rapid Visco Analyzer (RVA) to determine the viscosity properties") and then stored, for 24 h at room temperature, in a closed vessel.

The samples were fixed under the probe (cylindrical plunger having a planar surface) of a TA-XT2 texture analyzer supplied by Stable Micro Systems (Surrey, UK), and the gel strength was determined using the following parameters:

| | |
|---|---|
| Test speed | 0.5 mm/sec |
| Penetration depth | 7 mm |
| Contact area | 113 mm² |
| Pressure | 2 g | e) Using Ion Exchange Chromatography to Analyze the Side Chain Distribution of the Amylopectin In order to separate amylose and amylopectin, 200 mg of starch were dissolved in 50 ml reaction vessels containing 12 ml of 90% (v/v) DMSO in $H_2O$. After 3 volumes of ethanol had been added, the precipitate was separated off by centrifuging for 10 minutes at about 1800 g and at room temperature (RT). The pellet was then washed with 30 ml of ethanol, dried and dissolved at 75° C. in 40 ml of 1% (w/v) NaCl solution. After the solution had been cooled down to 30° C., about 90 mg of thymol were added slowly and this solution was incubated at 30° C. for at least 60 h. The solution was then centrifuged at 2000 g (RT) for 30 min. The supernatant was treated with 3 volumes of ethanol and the amylopectin which precipitated out was separated off by centrifuging at 2000 g (RT) for 5 minutes. The pellet (amylopectin) was then washed with ethanol and dried using acetone. A 1% solution of amylopectin was then prepared in 10 mM sodium acetate, pH 3.5, with the amylopectin being dissolved at 65-95° C. for 1-2 h. In each case 100 µl of this solution were treated, for the digestion, with 180 µl of 10 mM sodium acetate, pH 3.5, and 1 µl of isoamylase (Megazyme) and the mixture was incubated at 37° C. for about 16 h. A 1:5 aqueous dilution of this digestion was then filtered using an 0.2 µm filter and 100 µl of the filtrate were analyzed by ion chromatography (HPAEC-PAD, Dionex). The separation was effected using a PA-100 column (with appropriate precolumn), and the detection was effected amperometrically.

The elution conditions were as follows:

| t (min) | Solution A (%) | Solution B (%) |
|---|---|---|
| 5 | 0 | 100 |
| 35 | 30 | 70 |
| 45 | 32 | 68 |
| 60 | 100 | 0 |
| 70 | 100 | 0 |
| 72 | 0 | 100 |
| 80 | 0 | 100 |
| stop | | |

Solution A - 0.15 M NaOH
Solution B - 1 M sodium acetate in 0.15 M NaOH

The relative proportion of short side chains in the total content of all the side chains was determined by determining the content of a particular side chain as a percentage of the total content of all the side chains. The total content of all the detectable side chains was elucidated by determining the total area under the peaks which represent the DP6 to 34 degrees of polymerization in the HPLC chromatogram.

The content of a particular side chain expressed as a percentage of the total content of all the side chains was elucidated by determining the ratio of the area of the peak which represents this side chain in the HPLC chromatogram to the total area. Version 6.20 of the Chromelion 6.20 program supplied by Dionex, USA, was used for determining the peak areas.

f) Using Gel Permeation Chromatography to Analyze the Side Chain Distribution in Total Starch In order to use gel permeation chromatography to determine the side chain distribution in total starch, 10 mg of starch were dissolved, at 60° C. for approx. 3 h, in 250 µl of 90% (v/v) DMSO. After 375 µl of H$_2$O (dist.) had been added, the solution was heated at 95° C. for approx. 1 h.

For the enzymic digestion of the starch, 200 µl of starch solution were added to 300 µl of 16.6 mM sodium acetate, pH 3.5, and incubated at 37° C. for about 16 h by adding 2 µl of isoamylase (Megazyme). An aqueous 1:4 dilution of this digestion was then filtered using an 0.2 µm filter and 25 µl of the filtrate were analyzed by means of gel permeation chromatography.

The separation was effected using two columns which were connected in series; that is firstly a Gram 3000 column (Polymer Standards Service with appropriate precolumn), with this then being followed by a Gram 100 column. A refraction index detector (RI 71, Shodex) was used for the detection. The column was equilibrated with 90% (v/v) DMSO, 90 mM sodium acetate. The column was eluted with 90% (v/v) DMSO, 90 mM sodium acetate at a flow rate of 0.7 ml/min and over a period of 1 h.

In order to correlate the elution volume with the molar mass, the columns which were used were calibrated with dextran standards (Fluka, product #31430). The dextrans which were used, their appurtenant molar masses, and the elution volumes, are shown in Table 1. The resulting calibration straight lines were used to depict the elution plot as a molecular weight distribution (FIG. 1):

TABLE 1

Dextran standard calibration table

| Elution volume (ml) | Molar mass [D] | Sample name |
|---|---|---|
| 19.22 | 401300 | dextran T670P |
| 20.05 | 276500 | dextran T410P |
| 21.03 | 196300 | dextran T270P |
| 21.93 | 123600 | dextran T150P |
| 22.98 | 66700 | dextran T80 |
| 24.00 | 43500 | dextran T50 |
| 25.43 | 21400 | dextran T25 |
| 27.22 | 9890 | dextran T12 |
| 28.55 | 4440 | dextran T5 |
| 30.92 | 1080 | dextran T1 |

In this connection, the total area of the GPC chromatogram was divided into individual sections which represented respective groups of side chains of differing lengths. The sections which were chosen contain side chains having the following degrees of polymerization (dp=number of glucose monomers within a side chain): dp<12, dp12-19, dp20-25, dp26-31, dp32-37, dp38-43, dp44-49, dp50-56, dp57-62, dp63-123 and >dp123. The dextrans which were used, their appurtenant molar masses, and the elution volumes, are shown in Tab. 1. The resulting calibration straight lines are used to depict the elution plot as a molecular weight distribution (FIG. 1). In order to determine the molecular weights of the individual side chains, glucose was specified to have a molecular weight of 162. The total area in the GPC chromatogram is stipulated to be 100% and the amounts represented by the area of the individual sections are calculated based on the amount represented by the total area:

g) Determining the Freeze/Thaw Stability

In order to determine the freeze/thaw stability, in each case 3.5 g of starch (dry weight) were made up to 70 ml with distilled water and pasted for 15 min at 90° C. (128 rpm, inclined blade stirrer) in a rotary viscometer (Rotovisko, Haake). The starch paste was then autoclaved, at 121° C. for 15 min, in a glass vessel having a screw closure. After that, in each case 5 g of this paste were subjected 3 times, likewise in a glass vessel having a screw closure, to a freeze/thaw cycle (from room temperature down to −20° C.). This quantity of paste was then treated with 25 ml of distilled water, homogenized at 8000 rpm for 1 min in an Ultra-Turrax, and then extracted on a magnetic stirrer for 1 h at 37° C. in a drying oven. The sample was then transferred to a 50 ml volumetric flask and made up to 50 ml with distilled water; this mixture was then centrifuged at 2800 g for 5 min and filtered. An aliquot of this filtrate was inspissated overnight at 105° C. and the residue was weighed. The freeze/thaw stability was then calculated as follows:

$$\text{Freeze/thaw stability}(\%) = \frac{50 \times 100 \times TS \text{ in the weighing pan}(g)}{\text{aliquot}(g) \times \text{starch } TS \text{ in the sample}(g)}$$

h) Determining the Heat Stability

In order to determine the heat stability, in each case 3.5 g of starch (dry weight) were made up to 70 ml with distilled water and pasted for 15 min at 90° C. (128 rpm, inclined blade stirrer) in a rotary viscometer (Rotovisko, Haake). The starch paste was then autoclaved, at 121° C. for 15 min, in a glass vessel having a screw closure and subsequently transferred back to the rotary viscometer beaker.

After 6 min at 90° C., and with the blade stirrer rotating at 128 rpm, the scale graduation was read and compared with the value which was measured after 21 min at 128 rpm and 90° C. without any autoclaving.

$$\text{Heat stability }(\%) = \frac{\text{Scale graduation(after autoclaving)} \times 100}{\text{Scale graduation(21 min, 128 rpm, 90° C.)}}$$

i) Differential Scanning Calorimetry (DSC) Measurement

For a DSC measurement, 10 mg of starch were weighed into a stainless steel cup (volume 50 µl) containing 30 µl of distilled water. An empty stainless steel cup was used as reference. The sample was heated from 20° C. to 120° C. at a heating rate of 10° C./min in a Diamond DSC appliance (Perkin Elmer). The data were analyzed using a Pyres software program. This involved determining T(onset), T(peak) and the free enthalpy.

j) The Total Phosphate Content was Determined Using the Ames Method (Methods in Enzymology VIII, (1966), 115-118)

30 µl of ethanolic magnesium nitrate solution are added to approx. 50 mg of starch and the mixture is incinerated at 660° C. for three hours in a muffle furnace. 500 µl of 0.5 M hydrochloric acid are added to the residue and the mixture is incubated at 60° C. for 30 min. An aliquot of 10 or 20 µl (depending on the expected phosphate content) is then made up to 300 µl with 0.5 M hydrochloric acid and this mixture is added to a mixture of 100 µl of 10% ascorbic acid and 600 µl of 0.42% ammonium molybdate in 0.5 M sulfuric acid and the whole is incubated at 45° C. for 20 min.

This is then followed by a photometric determination at 820 nm using a phosphate calibration series as standard.

k) Determination of the Shear Stability of Starches

Shear stability was determined using a "Viskotester VT 550" (Type 002-7026), Gebrüder Haake, Dieselstraße 4, D 76227 Karlsruhe.

70 g of a starch suspension (5% w/v) were transferred to the container that is used for the measurements. This container was transferred to the heating device which had been adjusted to 90° C. prior to that. Upon starting the measurement the slurry was stirred by a paddle agitator at 128 rpm (revolutions per minute) while the viscosity was recorded (software version 2.30.P). After 15 minutes the speed of the stirrer was increased to 512 rpm. After 5 minutes stirrer speed again was reduced to 128 rpm. Total time for the measurement was 21 minutes.

To determine the stability against shear forces, a suspension of the same starch having the same concentration was examined under identical conditions. However, in this second experiment the stirrer speed was kept at 128 rpm for the entire period of 21 min.

Viscosity is expressed as a relative viscosity having the unit "Skalenteile" (SKT).

Shear stability is expressed as the ratio of the viscosities after 21 min of the starch slurry that was stirred at 512 rpm to the slurry that was stirred at 128 rpm only.

$$\text{Shear stability}(\%) = \frac{\text{Viscosity}_{(21\,min)} \text{ stirred at 512 rpm} \times 100}{\text{Viscosity}_{(21\,min)} \text{ stirred at 128 rpm}}$$

l) Determination of the Peak Viscosity by the Rotovisko Method

Peak viscosity was determined using a "Viskotester VT 550" (Type 002-7026) Gebrüder Haake, Dieselstraβe 4, D 76227 Karlsruhe.

70 g of a starch suspension (5% w/v) were transferred to the container that is used for the measurements. This container was transferred to the heating device which had been adjusted to 90° C. prior to that. Upon starting the measurement the slurry was stirred by a paddle agitator at 128 rpm (revolutions per minute) while the viscosity was recorded (software version 2.30.P). The measurement was terminated after 15 minutes.

Viscosity is expressed as a relative viscosity having the unit "Skalenteile" (SKT).

Peak viscosity is the maximum viscosity as recorded during the period of measurement.

DESCRIPTION OF THE SEQUENCES

Seq ID 1: Nucleic acid sequence of the potato (*Solanum tuberosum*) starch synthase SSIII, with the sequences which encode the corresponding SSIII protein being indicated.

Seq ID 2: Amino acid sequence of a potato SSIII protein.

Seq ID 3: Amino acid sequence of the Pfam cbm25 binding domain of the potato (*Solanum tuberosum*) SSIII protein.

Seq ID 4: Nucleic acid sequence encoding the potato (*Solanum tuberosum*) branching enzyme BEI.

Seq ID 5: Amino acid sequence of the potato (*Solanum tuberosum*) branching enzyme BEI.

Seq ID 6: Coding nucleic acid sequence of the potato (*Solanum tuberosum*) GBSSI gene.

Seq ID 7: Amino acid sequence of potato (*Solanum tuberosum*) GBSSI.

Seq ID 8: Primer B1_Asp

SEQ ID NO 9: Nucleic acid sequence containing the region encoding the 3' region of a *Solanum tuberosum* (cv Désirée) protein involved in starch biosynthesis. This sequence is inserted in plasmid AN 46-196.

SEQ ID NO 10: Nucleic acid sequence containing the region encoding the 5' region of a *Solanum tuberosum* (cv Désirée) protein involved in starch biosynthesis. This sequence is inserted in plasmid AN 47-196.

SEQ ID NO 11: Nucleic acid sequence containing the complete region encoding a *Solanum tuberosum* (cv Désirée) protein involved in starch biosynthesis. This sequence is inserted in plasmid AN 49. This plasmid was deposited, in accordance with the Budapest Treaty, on Sep. 15, 2003 in the Deutsche Sammiung von Mikroorganismen und Zellkulturen [German Collection of Microorganisms and Cell Cultures] GmbH, Mascheroder Weg 1b, 38124 Braunschweig, Germany, under the number DSM 15926.

SEQ ID NO 12: Amino acid sequence encoding a *Solanum tuberosum* (cv Désirée) protein involved in starch biosynthesis. This sequence can be deduced from the nucleic acid sequence inserted in plasmid AN 49 or from the nucleic acid sequence described under SEQ ID NO 11.

SEQ ID NO 13: Nucleic acid sequence containing the complete region encoding a *Solanum tuberosum* (cv Désirée) protein involved in starch biosynthesis. This sequence was obtained by joining together the nucleic acid sequences which are described under SEQ ID NO 9 and SEQ ID NO 10. This nucleic acid sequence constitutes an allelic variant of the nucleic acid sequence described under SEQ ID NO 11 encoding a protein involved in starch biosynthesis.

SEQ ID NO 14: Amino acid sequence encoding a *Solanum tuberosum* (cv Désirée) protein involved in starch biosynthesis. This sequence can be deduced from the nucleic acid sequence described under SEQ ID NO 13 and constitutes the amino acid sequence of an allelic variant of the amino acid sequence described under SEQ ID NO 12 encoding a protein involved in starch biosynthesis.

```
SEQ ID NO 15:
Primer B2_Sal
(TCA AGT CGA CCA CAA CCA GTC CAT TTC TGG)

SEQ ID NO 16
Primer KM2_Spe
(5'-TCAAACTAGTCACAACCAGTCCATTTCTGG-3')

SEQ ID NO 17
Primer SoputE
(5'-CACTTTAGAAGGTATCAGAGC-3')

SEQ ID NO 18
Primer So_put5'
(5'-GTATTTCTGCGAAGGAACGACC-3')

SEQ ID NO 19
Primer So_putA
(5'-AACAATGCTCTCTCTGTCGG-3')

SEQ ID NO 20
Primer B3_Sal
(GCT TGT CGA CGG GAG AAT TTT GTC CAG AGG)

SEQ ID NO 21
Primer B4_Sal
(GAT CGT CGA CAG CAC TTC TAC TTG GCA GAG G)
```

DESCRIPTION OF THE FIGURES

FIG. 1: Calibration curve for GPC

EXAMPLE 1

Producing Transgenic Potato Plants which Exhibit a Reduced Expression of the BEI, SSIII and GBSSI Genes In order to generate transgenic plants which exhibit reduced BEI, SSIII and GBSSI activities, transgenic plants which exhibited reduced BEI and SSIII activities were first of all generated. For this purpose, agrobacteria were used, as described in Rocha-Sosa et al. (1989, EMBO J. 8, 23-29), to transfer the T-DNA of the plasmid pB33-aBEI-aSSIII-Kan into potato plants.

In order to construct the plasmid pB33-aBEI-aSSIII-Kan, the expression vector pBin33-Kan was first of all constructed. For this, the promoter of the *Solanum tuberosum* patatin gene B33 (Rocha-Sosa et al., 1989, see above) was ligated, as a DraI fragment (nucleotides-1512-+14), into the vector pUC19 (Genbank Acc. No. M77789), which had been cut with SstI and whose ends had been smoothed using T4 DNA polymerase. This resulted in the plasmid pUC19-B33. The B33 promoter was excised from this plasmid using EcoRI and SmaI and ligated into the vector pBinAR, which had been cut correspondingly. This resulted in the plant expression vector pBin33-Kan. The plasmid pBinAR is a derivative of the vector plasmid pBin19 (Bevan, 1984, Nucl. Acid Research 12, 8711-8721) and was constructed by Höfgen and Willmitzer (Plant Sci. 66 (1990), 221-230). A HindIII fragment of 1631 bp in length, which contains a partial cDNA encoding the potato BEI enzyme (Kossmann et al., 1991, Mol. Gen. Genet. 230(1-2):39-44), was then smoothed and introduced into vector pBinB33, which had been previously cut with SmaI, in the antisense orientation in regard to the B33 promoter (promoter of the *Solanum tuberosum* patatin gene B33; Rocha-Sosa et al., 1989, loc. cit.). The resulting plasmid was cut with BamHI. A BamHI fragment of 1363 bp in length, containing a partial cDNA encoding the potato SSIII protein (Abel et al., 1996, loc. cit.), was introduced into the cleavage site, likewise in the antisense orientation with regard to the B33 promoter.

In order to detect the activity of soluble starch synthases by means of nondenaturing gel electrophoresis, tissue samples of potato tubers were disrupted in 50 mM Tris-HCl, pH 7.6, 2 mM DTT, 2.5 mM EDTA, 10% glycerol and 0.4 mM PMSF. The electrophoresis was carried out in a MiniProtean II chamber (BioRAD). The monomer concentration of the gels, which were 1.5 mm thick, was 7.5% (w/v), while 25 mM Tris-glycine, pH 8.4, served as the gel buffer and running buffer. Equal quantities of protein extract were loaded on and fractionated for 2 h at 10 mA per gel.

The activity gels were then incubated in 50 mM Tricine-NaOH, pH 8.5, 25 mM potassium acetate, 2 mM EDTA, 2 mM DTT, 1 mM ADP-glucose, 0.1% (w/v) amylopectin and 0.5 M sodium citrate. Glucans which were formed were stained with Lugol's solution.

BEI activity was likewise detected using nondenaturing gel electrophoresis: in order to isolate proteins from plants, the sample material was triturated in liquid nitrogen, taken up in extraction buffer (50 mM Na citrate, pH 6.5; 1 mM EDTA, 4 mM DTT) and, after centrifugation (10 min, 14 000 g, 4° C.), used directly for measuring the protein concentration as described by Bradford. From 5 to 20 μg, as required, of total protein extract were then treated with 4-fold loading buffer (20% glycerol, 125 mM Tris HCl, pH 6.8) and loaded onto a "BE activity gel". The composition of the running buffer (RB) was as follows: RB=30.2 g of Tris base, pH 8.0, 144 g of glycine made up to 1 l with $H_2O$.

After the gel run had come to an end, the gels were in each case incubated overnight at 37° C. in 25 ml of "phosphorylase buffer" (25 ml of 1 M Na citrate, pH 7.0, 0.47 g of glucose-1-phosphate, 12.5 mg of AMP, 2.5 mg of rabbit phosphorylase a/b). The gels were stained with Lugol's solution.

It was possible to identify different lines of transgenic potato plants whose tubers exhibited markedly reduced BEI and SSIII activities. The line (asBEI-asSSII), whose isolated starches exhibited the highest phosphate content of all the independent transformants which were investigated, was then transformed with the plasmid p35SaGBSSI-Met as described in Rocha-Sosa et al. (1989, EMBO J. 8, 23-29).

Plasmid p35SaGBSSI-Met was prepared by inserting an Asp718/XbaI fragment of 1921 bp in length, containing a partial cDNA encoding potato GBSSI (Hergersberg, 1988, see above) into the vector pBinAR-Met, which had also been opened, in the antisense orientation with regard to the 35S promoter.

Vector pBinAR-Met is derived from the plasmid pGPTV-DHFR, which is a derivative of the vector pBin19 (Becker et al., 1992, Plant Mol. Biol. 20, 1195-1197). pBinAR-Met contains the dhfr gene, which mediates resistance to methotrexate, instead of the nptII gene and the 3' end of gene 7 of the T-DNA of the Ti plasmid pTiACH5 (nucleotides 2106-2316; Gielen et al., 1984, EMBO J. 3, 835-846) instead of the 3' end of the nopaline synthase gene. Taking plasmid pA7 (compare description of vector pBinAR above) as the starting point, the EcoRI/HindIII fragment, comprising the 35S promoter, the ocs terminator and the intercollated part of the polylinker, was ligated into plasmid PGPTV-DHFR, which was cut correspondingly. The resulting vector was designated pBinAR-Met.

Tissue samples were taken from tubers derived from the independent transformants among the plants which were obtained by transformation with the plasmid p35SaGBSSI-Met, and which were designated asBEI-asSSIII-asGBSSI plants, and the samples were stained with iodine solution and examined under the microscope. The starches of the independent lines whose granules stained brown were used for further analysis of the starch properties.

EXAMPLE 2

Cloning a Full-Length Sequence of a *Solanum tuberosum* Gene having the Sequence Specified Under SEQ ID NO 11 or 13

The nucleotide sequence (SEQ ID No. 11 or SEQ ID No. 13) encoding a *Solanum tuberosum* protein having the amino acid sequence specified under SEQ ID No. 12 or SEQ ID No.14 has not been previously described. By making sequence comparisons using different branching enzymes, it was possible to identify a domain which was used to screen EST databases. The potato EST TC73137 (TIGR database; http://www.tigr.org/tigr-scripts/tgi/tc_report.pl?tc=TC73137&species=potato) was identified in this connection.

The primers B1_Asp (GAT GGG TAC CAG CAC TTC TAC TTG GCA GAG G=SEQ ID No. 8) and B2_Sal (TCA AGT CGA CCA CAA CCA GTC CAT TTC TGG=SEQ ID No. 15) were used to amplify a sequence, which corresponded to this EST sequence, from a tuber-specific *Solanum tuberosum* (cv Désirée) cDNA library. Attempts to use leaf-specific, sink or source tissue-specific cDNA libraries as templates for the PCR reaction did not give rise to any amplificate.

Primers which were complementary to the ends of the previously known sequence and vector sequences of the relevant cDNA libraries were prepared for the purpose of amplifying the entire sequence encoding the protein concerned, which sequence also comprised previously unknown sequences. None of the primer combinations for amplifying a full-length sequence which were used when taking this approach led to any further region being amplified. Tomato EST databases were consequently screened once again.

In this connection, it was possible to identify two tomato ESTs (TIGR database; BG127920 and TC130382) which either exhibited a high degree of homology with the above-described amplificate of the potato protein (TC130382) or (BG127920) or with a putative branching enzyme derived from *Arabidopsis* (Genbank: GP|9294564|dbj|BAB02827.1).

Primers were now prepared once again in order to also amplify previously unknown sequences of the protein having the amino acid sequence depicted under SEQ ID NO 12 or SEQ ID NO 14. The 3' region of the protein concerned was amplified by means of PCR, using the primers KM2_Spe (5'-TCAAACTAGTCACAACCAGTCCATTTCTGG-3'=SEQ ID No. 16) and SoputE (5'-CACTTTAGAAGGTAT-CAGAGC-3'=SEQ ID No. 17), from a cDNA library which was prepared from *Solanum tuberosum* (cv Désirée) tubers. The resulting fragment, of approx. 1 kb in size, was cloned in an undirected manner into the pCR4-TOPO vector supplied by Invitrogen (product number: 45-0030). The resulting plasmid was designated AN 46-196. The sequence of the fragment inserted in plasmid AN 46-196 is depicted under SEQ ID NO 9.

The 5' region was likewise amplified by means of the PCR technique from the same cDNA library using the primers So_put5' (5'-GTATTTCTGCGAAGGAACGACC-3'=SEQ ID No. 18) and So_putA (5'-AACAATGCTCTCTCT-GTCGG-3'=SEQ ID No. 19). The resulting fragment, of approx. 2 kb in size, was cloned in an undirected manner into the pCR4-TOPO Invitrogen vector (product number: 45-0030). The resulting plasmid was designated AN 47-196. The sequence of the fragment inserted in plasmid AN 47-196 is depicted under SEQ ID NO 10.

Primers were now prepared once again in order to amplify a full-length sequence.

The following primers were used: SOputA (AACAATGCTCTCTCTGTCGG=SEQ ID No. 19) and SO_putE (CACTTTAGAAGGTATCAGAGC=SEQ ID No. 17). A PCR product of approximately 3.2 kb in size was obtained and cloned into the Invitrogen vector pCR2.1 (product number: 45-0030). The resulting plasmid (deposited under DSM 15926) was designated AN 49. The sequence of the fragment inserted in plasmid AN 49 is depicted under SEQ ID NO 11.

The sequence information in the nucleic acid sequence depicted under SEQ ID No. 13 was obtained by joining the nucleic acid sequences described under SEQ ID NO 9 and SEQ ID NO 10. This nucleic acid sequence is an allelic variant of the nucleic acid sequence described under SEQ ID No 11 encoding a protein (SEQ ID No. 14) which is involved in starch biosynthesis.

EXAMPLE 3

Producing Transgenic Potato Plants which Exhibit a Reduced Expression of the BEI, SSIII and GBSSI Genes and a Reduced Expression of the Gene which is Specified Under SEQ ID NO. 11 or SEQ ID No. 13

Agrobacteria were used, as described in Rocha-Sosa et al. (EMBO J. 8, (1989), 23-29), to the T-DNA of the plasmid AN 54-196 (see below) into the potato plants having a reduced expression of the BEI, SSIII and GBSSI genes, which plants were described in example 1 and designated, in that example, as asBEI-asSSIII-asGBSSI plants. The plants which were obtained by transformation with plasmid AN 54-196 were designated asBEI-asSSIII-asGBSSI-iBE3 and, in addition to exhibiting reduced expression of the BEI, SSIII and GBSSI genes, also exhibited a reduction in the expression of the gene described under SEQ ID No. 11 or SEQ ID No. 13. Tissue samples were taken from tubers derived from independent transformants, stained with iodine and examined under the microscope. The phosphate content in the C6 position was also determined. The starches from the independent lines whose granules stained brown and which exhibited a phosphate content which was greater than that of the starting lines (see example 1) were used for further analysis of the starch properties.

Information Concerning Vector AN 54-196

AN 54-196 is a derivative of plasmid pBinB33-Hyg, into which a constituent sequence of the coding nucleic acid sequence specified under SEQ ID NO 11 or SEQ ID NO 13 was inserted as an inverted repeat (RNAi technology) under the control of the promoter of the *Solanum tuberosum* patatin gene B33 (Rocha-Sosa et al., 1989). For this, a PCR product was first of all amplified from a tuber-specific *Solanum tuberosum* (cv Désirée) cDNA library using the primers B1_Asp (GAT GGG TAC CAG CAC TTC TAC TTG GCA GAG G) and B2_Sal (TCA AGT CGA CCA CAA CCA GTC CAT TTC TGG) resulting in the cleavage sites Asp718 and SalI being added. The PCR product (625 bp) which was obtained was cloned, in the antisense orientation with regard to the B33 promoter, by way of these two cleavage sites. A second PCR fragment, which was amplified from a tuber-specific *Solanum tuberosum* (cv Désirée) cDNA library using the primers B3_Sal (GCT TGT CGA CGG GAG AAT TTT GTC CAG AGG=SEQ ID No. 20) and B4_Sal (GAT CGT CGA CAG CAC TTC TAC TTG GCA GAG G=SEQ ID No. 21), and which was identical to 301 bp of the first fragment, was cloned, by way of the SalI cleavage site, downstream of the first fragment but in the sense orientation with regard to the B33 promoter. This arrangement is designated an inverted repeat (RNAi technology).

Information Concerning Vector pBinB33-Hyg

The EcoRI-HindIII fragment comprising the B33 promoter, a part of the polylinker and the ocs terminator, was excised from plasmid pBinB33 and ligated into the vector pBIB-Hyg (Becker, 1990), which had been cut correspondingly.

The plasmid pBinB33 was obtained by ligating the promoter of the *Solanum tuberosum* patatin gene B33 (Rocha-Sosa et al., 1989), as a DraI fragment (nucleotides-1512-+14), into the SstI-cut vector pUC19, whose ends had been smoothed using T4 DNA polymerase. This resulted in the plasmid pUC19-B33. The B33 promoter was excised from this plasmid using EcoRI and SmaI and ligated into vector pBinAR, which had been cut correspondingly. This resulted in the plant expression vector pBinB33.

The plasmid pBinAR is a derivative of the vector plasmid pBin19 (Bevan, 1984) and was constructed as follows:

A fragment of 529 bp in length, which comprises nucleotides 6909-7437 of the cauliflower mosaic virus 35S RNA promoter (Pietrzak et al., 1986, Nucleic Acids Research 14, 5857-5868), was isolated, as an EcoRI/KpnI fragment, from the plasmid pDH51 (Pietrzak et al., 1986) and ligated between the EcoRI and KpnI cleavage sites of the pUC18 polylinker. This resulted in the plasmid pUC18-35S.

A fragment of 192 bp in length, which comprises the polyadenylation signal (3' end) of the *octopine synthase* gene (gene 3) of the T-DNA of the Ti-plasmid pTiACH5 (Gielen et al., 1984) (nucleotides 11749-11939), was isolated from the plasmid pAGV40 (Herrera-Estrella et al., 1983) using the restriction endonucleases HindIII and PvuII. After SspI linkers had been added to the PvuII cleavage site, the fragment was ligated between the SphI and HindIII cleavage sites of pUC18-35S. This resulted in the plasmid pA7.

The entire polylinker, containing the 35S promoter and the ocs terminator, was excised from pA7 using EcoRI and HindIII and ligated into pBin19, which had been cut correspondingly. This resulted in the plant expression vector pBinAR (Höfgen and Willmitzer, 1990).

EXAMPLE 4

Analyzing the Starch of Transgenic Potato Plants which Exhibit Reduced Expression of the BEI, SSIII and GBSSI Genes and Reduced Expression of the Gene Which is Specified Under SEQ ID No. 11 or SEQ ID No. 13

The starches were isolated from the tubers obtained from different independent lines of the asBEI-asSSIII-asGBSSI-iBE3 potato transformants described in example 3. The physicochemical properties of these starches were then analyzed. The results which were obtained on the basis of the starches which were prepared from the plant cells or plants according to the invention are given below either as absolute values or as percentage values based on starch from corresponding wild-type plant cells or wild-type plants (designated WT starch in that which follows) (table 2). In addition, the table contains starch data from "single" or "double" combinations disclosed in WO 00/08184 and WO 01/12782:

TABLE 2

| | % based on WT starch | | |
|---|---|---|---|
| | Phosphate in C6 | Amylose | Gel strength |
| asSSIII | 197 | 123 | 84 |
| cosSSIII | 210 | — | 83 |
| asBEI | 170 | 91 | 91 |
| asGBSSI | 110 | <18 | — |
| asBEI-asSSIII | 292 | 89 | 100 |
| asGBSSI-asBEI | 181 | <18 | 21 |
| asBEI-asSSIII-asGBSSI | 360 | <18 | 16 |
| asBEI-asSSIII-asGBSSI-iBE3 | 462 | <18 | — |

In addition, the absolute values for the amylose content (determined using the methods of Hovenkamp-Hermelink) and for the phosphate content in the C6 position (method description, see "General methods" above) were determined in the case of the starches from the corresponding wild-type plants (Desiree variety), from the starting line (asBEI-asSSIII-asGBSSI) and from the asBEI-asSSIII-asGBSSI-iBE3 potato plants (table 3):

TABLE 3

Amylose content and phosphate content in the C6 position

| Genotype | C6 phosphate [nmol/mg] | Amylose [% of the total starch] |
|---|---|---|
| Desiree (wild type) | 12.1 | 24.1 |
| asBEI-asSSIII-asGBSSI | 43.5 | <3 |
| asBEI-asSSIII-asGBSSI-iBE3 | 56.3 | <3 |

The side-chain profile of the potato starch was analyzed by determining the content of a particular group of side chains expressed as a percentage of the total content of all the side chains in the GPC chromatogram (table 4) (see General methods "Using gel permeation chromatography to analyze the side-chain distribution of total starch"):

TABLE 4

Distribution of the side-chain profile of total starch in the lines asBEI-asSSIII, asBEI-asSSIII-asGBSSI asBEI-asSSIII-asGBSSI-iBE3 and the corresponding wild type, divided into groups having different degrees of polymerization

| Degree of polymerization (dp) | % based on WT starch | | |
|---|---|---|---|
| | asBEI-asSSIII | asBEI-asSSIII-asGBSSI | asBEI-asSSIII-asGBSSIiBE3 |
| dp <12 | 119.71 | 156.57 | 153.27 |
| dp 12-19 | 103.83 | 119.00 | 147.90 |
| dp 20-25 | 120.36 | 131.79 | 142.80 |
| dp 26-31 | 127.31 | 142.19 | 130.42 |
| dp 32-37 | 122.60 | 144.16 | 120.97 |
| dp 38-43 | 103.14 | 130.00 | 110.77 |
| dp 44-49 | 83.42 | 114.95 | 92.40 |
| dp 50-56 | 72.51 | 106.85 | 93.47 |
| dp 57-62 | 68.85 | 105.21 | 90.28 |
| dp 63-123 | 56.44 | 91.78 | 77.70 |
| dp >123 | 104.21 | 3.97 | 0.96 |

The ratio of the total phosphate content to the phosphate content in the C6 position was also determined:

| Genotype | Total phosphate content/ C6 phosphate content |
|---|---|
| Desiree (wild type) | 1.88 |
| asBEI-asSSIII-asGBSSI | 1.62 |
| asBEI-asSSIII-asGBSSI-iBE3 | 1.37 |

The gel strength of the potato starches according to the invention was analyzed by the method described above (see General Methods, Method d) "Determining the gel strength (texture analyzer)"):

| Genotype | Gel strength (g) |
|---|---|
| Desiree (wild type) | 26.0 |
| asBEI-asSSIII-asGBSSI | 3.3 |
| asBEI-asSSIII-asGBSSI-iBE3 | 4.5 |

The shear stability of the potato starches according to the invention was analyzed by the method described above (see General Methods, Method k):

| Genotype | Shear stability (%) |
|---|---|
| Desiree (wild type) | 56 |
| asBEI-asSSIII-asGBSSI-iBE3 | 70 |

The peak viscosity of the potato starches according to the invention was analyzed by the Rotovisko method described above (see General Methods, Method l):

| Genotype | Peak Viscosity (SKT) |
|---|---|
| Desiree (wild type) | 269 |
| asBEI-asSSIII-asGBSSI | 330 |
| asBEI-asSSIII-asGBSSI-iBE3 | 385 |

The freeze/thaw stability of the potato starches according to the invention was analyzed by the method described above (see General Methods, Method g) "Determining the freeze/thaw stability"):

| Genotype | freeze/thaw stability (%) |
|---|---|
| Desiree (wild type) | 10.5 |
| asBEI-asSSIII-asGBSSI-iBE3 | 95.0 |

What is claimed:

1. A potato starch comprising an amylose content as measured by the method of Hovenkamp-Hermelink et al., of less than 10% by weight, a phosphate content in the C6 position of between 35 and 100 nmol of phosphate per milligram of starch (dry weight), and a proportion of side chains having a degree of polymerization (DP) of from 12 to 19 which is increased to 125%-200% as compared with potato starch from corresponding wild-type potato plants.

2. The potato of claim 1, wherein said phosphate content in the C6 position is between 40 and 85 nmol of phosphate per milligram of starch (dry weight).

3. The potato starch of claim 1, wherein said phosphate content in the C6 position is between 45 and 70 nmol of phosphate per milligram of starch (dry weight).

4. The potato starch of claim 1, wherein said phosphate content in the C6 position is between 50 and 65 nmol of phosphate per milligram of starch (dry weight).

5. The potato starch of claim 1, wherein said amylose content, as measured by the method of Hovenkamp-Hermelink et al. is less than 5% by weight.

6. The potato starch of claim 1, wherein said amylose content, as measured by the method of Hovenkamp-Hermelink et al., is less than 3% by weight.

7. The potato starch of claim 1, wherein the proportion of side chains having a DP of from 12 to 19 is increased to 130%-480% as compared with potato starch from corresponding wild-type potato plants.

8. The potato starch of claim 1, wherein the proportion of side chains having a DP of from 63 to 123 is reduced as compared with potato starch from corresponding wild-type potato plants.

9. The potato starch of claim 8, wherein the proportion of side chains having a DP of from 63 to 123 is reduced to 50%-95% as compared with potato starch from corresponding wild-type potato plants.

10. The potato starch of claim 1, wherein said phosphate content in the C6 position is elevated by 415%-520% as compared with that in potato starch from corresponding wild-type plants.

11. A derivatized potato starch comprising the potato starch of claim 1, wherein the derivatized potato starch is obtainable by subjecting the potato starch to a temperature treatment of 120° C.-140° C. in a dry system.

12. A derivatized potato starch comprising the potato starch of claim 1, wherein the derivatized potato starch is obtainable by treating the potato starch with acid in an aqueous system at temperatures up to 50° C.

13. A derivatized potato starch comprising the potato starch of claim 1, wherein the derivatized potato starch is a starch ether, crosslinked starch, oxidized starch, or starch ester.

14. A potato starch comprising an amylose content, as measured by the method of Hovenkamp-Hermelink et al., of less than 10% by weight, a phosphate content in the C6 position is between 35 and 100 nmol of phosphate per milligram of starch (dry weight), a total phosphate content to phosphate content in the C6 position ratio of 1.20-1.50, and a proportion of side chains having a DP of from 12 to 19 which is increased to 125%-200% as compared with that in potato starch from corresponding wild-type potato plants.

15. The potato starch of claim 14, wherein said phosphate content in the C6 position is between 40 and 85 nmol of phosphate per milligram of starch (dry weight).

16. The potato starch of claim 14, wherein said phosphate content in the C6 position is between 45 and 70 nmol of phosphate per milligram of starch (dry weight).

17. The potato starch of claim 14, wherein said amylose content, as measured by the method of Hovenkamp-Hermelink et al., is less than 5% by weight.

18. The potato starch of claim 14, wherein said amylose content, as measured by the method of Hovenkamp-Hermelink et al. is less than 3% by weight.

19. The potato starch of claim 14, wherein the proportion of side chains having a DP of from 12 to 19 is increased to 130%-180% as compared with potato starch from corresponding wild-type potato plants.

20. The potato starch of claim 14, wherein said phosphate content in the C6 position is between 50 and 65 nmol of phosphate per milligram of starch (dry weight).

21. A potato starch isolated from a potato plant cell which exhibits an activity
  (a) of one or more SSIII proteins which occur endogenously in the plant cell;
  (b) of one or more BEI proteins which occur endogenously in the plant cell;
  (c) of one or more GBSSI proteins which occur endogenously in the plant cell; and
  (d) of one or more proteins which occur endogenously in the plant cell and which exhibit an at least 90% identity with the amino acid sequence of SEQ ID NO: 12 or SEQ ID NO: 14,
  which is reduced as compared with that of corresponding wild-type potato plant cells, and
  wherein said starch has a proportion of side chains having a degree of polymerization (DP) of from 12 to 19 which is increased to 125%-200% as compared with potato starch from corresponding wild-type potato plants.

22. The starch of claim 21, wherein said starch is isolated from a potato plant cell comprising
  (a) a first foreign nucleic acid molecule that reduces the expression of at least one endogenous gene encoding a SSIII protein;

(b) a second foreign nucleic acid molecule that reduces the expression of at least one endogenous gene encoding a BEI protein; and
(c) a third foreign nucleic acid molecule that reduces the expression of at least one endogenous gene encoding a GBSSI protein; and
(d) a fourth foreign nucleic acid molecule that reduces the expression of at least one nucleic acid molecule that has an identity of at least 90% with SEQ ID NO: 11 or SEQ ID NO: 13.

23. The starch of claim 22, wherein
(a) said first foreign nucleic acid molecule is
   (i) a nucleic acid molecule, which comprises the nucleotide sequence of SEQ ID NO: 1 or a complementary sequence thereof; or
   (ii) a nucleic acid molecule, which has an identity of at least 95% with nucleic acid sequence with SEQ ID NO: 1
(b) said second foreign nucleic acid molecule is
   (i) a nucleic acid molecule, which comprises the nucleotide sequence of SEQ ID NO: 4 or a complementary sequence thereof; or
   (ii) a nucleic acid molecule, which has an identity of at least 95% with nucleic acid sequence with SEQ ID NO: 4;
(c) said third foreign nucleic acid molecule is
   (i) a nucleic acid molecule, which comprises the nucleotide sequence of SEQ ID NO 6 or a complementary sequence thereof; or
   (ii) a nucleic acid molecule, which has an identity of at least 95% with nucleic acid sequence with SEQ ID NO: 6; and
(d) said fourth foreign nucleic acid molecule is
   (i) a nucleic acid molecule, which comprises the nucleotide sequence of SEQ ID NO: 11 or 13 or a complementary sequence thereof; or
   (ii) a nucleic acid molecule, which has an identity of at least 95% with nucleic acid sequence with SEQ ID NO: 11 or 13.

24. The starch of claim 22, wherein
(a) said first foreign nucleic acid molecule is
   (i) a DNA molecule encoding at least one antisense RNA that reduces the expression of at least one endogenous gene encoding a SSIII protein;
   (ii) a DNA molecule which, via a co-suppression effect, reduces the expression of at least one endogenous gene encoding a SSIII protein; or
   (iii) a DNA molecule that simultaneously encodes at least one antisense RNA and at least one sense RNA, where said antisense RNA and said sense RNA form a double-stranded RNA molecule that reduces the expression of at least one endogenous gene encoding a SSIII protein;
(b) said second foreign nucleic acid molecule is
   (i) a DNA molecule encoding at least one antisense RNA that reduces the expression of at least one endogenous gene encoding a BEI protein;
   (ii) a DNA molecule which, via a co-suppression effect, reduces the expression of at least one endogenous gene encoding a BEI protein; or
   (iii) a DNA molecule that simultaneously encodes at least one antisense RNA and at least one sense RNA, where said antisense RNA and said sense RNA form a double-stranded RNA molecule that reduces the expression of at least one endogenous gene encoding a BEI protein;
(c) said third foreign nucleic acid molecule is
   (i) a DNA molecule encoding at least one antisense RNA that reduces the expression of at least one endogenous gene encoding a GBSSI protein;
   (ii) a DNA molecule which, via a co-suppression effect, reduces the expression of at least one endogenous gene encoding a GBSSI protein; or
   (iii) a DNA molecule that simultaneously encodes at least one antisense RNA and at least one sense RNA, where said antisense RNA and said sense RNA form a double-stranded RNA molecule that reduces the expression of at least one endogenous gene encoding a GBSSI protein; and
(d) said fourth foreign nucleic acid molecule is
   (i) a DNA molecule encoding at least one antisense RNA that reduces the expression of at least one endogenous gene encoding SEQ ID NO: 12 or 14;
   (ii) a DNA molecule which, via a co-suppression effect, reduces the expression of at least one endogenous gene encoding SEQ ID NO: 12 or 14; or
   (iii) a DNA molecule that simultaneously encodes at least one antisense RNA and at least one sense RNA, where said antisense RNA and said sense RNA form a double-stranded RNA molecule that reduces the expression of at least one endogenous gene encoding SEQ ID NO: 12 or 14.

25. The starch of claim 24, wherein
(a) said first foreign nucleic acid molecule is a DNA molecule encoding at least one antisense RNA that reduces the expression of at least one endogenous gene encoding a SSIII protein;
(b) said second foreign nucleic acid molecule is a DNA molecule encoding at least one antisense RNA that reduces the expression of at least one endogenous gene encoding a BEI protein;
(c) said third foreign nucleic acid molecule is a DNA molecule encoding at least one antisense RNA that reduces the expression of at least one endogenous gene encoding a GBSSI protein; and
(d) said fourth foreign nucleic acid molecule is a DNA molecule that simultaneously encodes at least one antisense RNA and at least one sense RNA, where said antisense RNA and said sense RNA form a double-stranded RNA molecule that reduces the expression of at least one endogenous gene encoding SEQ ID NO: 12 or 14.

26. A method of manufacturing a potato starch comprising extracting starch from a potato plant cell, wherein said plant cell exhibits an activity
(a) of one or more SSIII proteins which occur endogenously in the plant;
(b) of one or more BEI proteins which occur endogenously in the plant;
(c) of one or more GBSSI proteins which occur endogenously in the plant; and
(d) of one or more proteins which occur endogenously in the plant and which exhibit an at least 90% identity with the amino acid sequence of SEQ ID NO: 12 or SEQ ID NO: 14,
which is reduced as compared with that of corresponding wild-type potato plant cells, and
wherein said starch has a proportion of side chains having a degree of polymerization (DP) of from 12 to 19 which is increased to 125%-200% as compared with potato starch from corresponding wild-type potato plants.

27. The method of claim 26, wherein said plant cell comprises
- (a) a first foreign nucleic acid molecule that reduces the expression of at least one endogenous gene encoding a SSIII protein;
- (b) a second foreign nucleic acid molecule that reduces the expression of at least one endogenous gene encoding a BEI protein; and
- (c) a third foreign nucleic acid molecule that reduces the expression of at least one endogenous gene encoding a GBSSI protein; and
- (d) a fourth foreign nucleic acid molecule that reduces the expression of at least one nucleic acid molecule that has an identity of at least 90% with SEQ ID NO: 11 or SEQ ID NO: 13.

28. The method of claim 27, wherein
- (a) said first foreign nucleic acid molecule is
  - (i) a nucleic acid molecule, which comprises the nucleotide sequence of SEQ ID NO: 1 or a complementary sequence thereof; or
  - (ii) a nucleic acid molecule, which has an identity of at least 95% with nucleic acid sequence with SEQ ID NO: 1
- (b) said second foreign nucleic acid molecule is
  - (i) a nucleic acid molecule, which comprises the nucleotide sequence of SEQ ID NO: 4 or a complementary sequence thereof; or
  - (ii) a nucleic acid molecule, which has an identity of at least 95% with nucleic acid sequence with SEQ ID NO: 4;
- (c) said third foreign nucleic acid molecule is
  - (i) a nucleic acid molecule, which comprises the nucleotide sequence of SEQ ID NO 6 or a complementary sequence thereof; or
  - (ii) a nucleic acid molecule, which has an identity of at least 95% with nucleic acid sequence with SEQ ID NO: 6; and
- (d) said fourth foreign nucleic acid molecule is
  - (i) a nucleic acid molecule, which comprises the nucleotide sequence of SEQ ID NO: 11 or 13 or a complementary sequence thereof; or
  - (ii) a nucleic acid molecule, which has an identity of at least 95% with nucleic acid sequence with SEQ ID NO: 11 or 13.

29. The method of claim 27, wherein
- (a) said first foreign nucleic acid molecule is
  - (i) a DNA molecule encoding at least one antisense RNA that reduces the expression of at least one endogenous gene encoding a SSIII protein;
  - (ii) a DNA molecule which, via a co-suppression effect, reduces the expression of at least one endogenous gene encoding a SSIII protein; or
  - (iii) a DNA molecule that simultaneously encodes at least one antisense RNA and at least one sense RNA, where said antisense RNA and said sense RNA form a double-stranded RNA molecule that reduces the expression of at least one endogenous gene encoding a SSIII protein;
- (b) said second foreign nucleic acid molecule is
  - (i) a DNA molecule encoding at least one antisense RNA that reduces the expression of at least one endogenous gene encoding a BEI protein;
  - (ii) a DNA molecule which, via a co-suppression effect, reduces the expression of at least one endogenous gene encoding a BEI protein; or
  - (iii) a DNA molecule that simultaneously encodes at least one antisense RNA and at least one sense RNA, where said antisense RNA and said sense RNA form a double-stranded RNA molecule that reduces the expression of at least one endogenous gene encoding a BEI protein;
- (c) said third foreign nucleic acid molecule is
  - (i) a DNA molecule encoding at least one antisense RNA that reduces the expression of at least one endogenous gene encoding a GBSSI protein;
  - (ii) a DNA molecule which, via a co-suppression effect, reduces the expression of at least one endogenous gene encoding a GBSSI protein; or
  - (iii) a DNA molecule that simultaneously encodes at least one antisense RNA and at least one sense RNA, where said antisense RNA and said sense RNA form a double-stranded RNA molecule that reduces the expression of at least one endogenous gene encoding a GBSSI protein; and
- (d) said fourth foreign nucleic acid molecule is
  - (i) a DNA molecule encoding at least one antisense RNA that reduces the expression of at least one endogenous gene encoding SEQ ID NO: 12 or 14;
  - (ii) a DNA molecule which, via a co-suppression effect, reduces the expression of at least one endogenous gene encoding SEQ ID NO: 12 or 14; or
  - (iii) a DNA molecule that simultaneously encodes at least one antisense RNA and at least one sense RNA, where said antisense RNA and said sense RNA form a double-stranded RNA molecule that reduces the expression of at least one endogenous gene encoding SEQ ID NO: 12 or 14.

30. The method of claim 29, wherein
- (a) said first foreign nucleic acid molecule is a DNA molecule encoding at least one antisense RNA that reduces the expression of at least one endogenous gene encoding a SSIII protein;
- (b) said second foreign nucleic acid molecule is a DNA molecule encoding at least one antisense RNA that reduces the expression of at least one endogenous gene encoding a BEI protein;
- (c) said third foreign nucleic acid molecule is a DNA molecule encoding at least one antisense RNA that reduces the expression of at least one endogenous gene encoding a GBSSI protein; and
- (d) said fourth foreign nucleic acid molecule is a DNA molecule that simultaneously encodes at least one antisense RNA and at least one sense RNA, where said antisense RNA and said sense RNA form a double-stranded RNA molecule that reduces the expression of at least one endogenous gene encoding SEQ ID NO: 12 or 14.

* * * * *